US012630640B2

(12) United States Patent
Morsey et al.

(10) Patent No.: US 12,630,640 B2
(45) Date of Patent: May 19, 2026

(54) BISPECIFIC CANINIZED ANTIBODIES FOR TREATING ATOPIC DERMATITIS

(71) Applicant: Intervet Inc., Madison, NJ (US)

(72) Inventors: Mohamad Morsey, Omaha, NE (US); Yuanzheng Zhang, Somerset, NJ (US); Anasuya Saha, Fremont, CA (US)

(73) Assignee: INTERVET INC., Rahway, NJ (US)

( * ) Notice: Subject to any disclaimer, the term of this patent is extended or adjusted under 35 U.S.C. 154(b) by 934 days.

(21) Appl. No.: 17/785,232

(22) PCT Filed: Dec. 18, 2020

(86) PCT No.: PCT/EP2020/086922

§ 371 (c)(1),
(2) Date: Jun. 14, 2022

(87) PCT Pub. No.: WO2021/123092

PCT Pub. Date: Jun. 24, 2021

(65) Prior Publication Data

US 2023/0250177 A1 Aug. 10, 2023

Related U.S. Application Data

(60) Provisional application No. 63/092,294, filed on Oct. 15, 2020, provisional application No. 63/092,296, filed on Oct. 15, 2020, provisional application No. 63/015,220, filed on Apr. 24, 2020, provisional application No. 63/015,209, filed on Apr. 24, 2020, provisional application No. 62/951,778, filed on Dec. 20, 2019, provisional application No. 62/951,793, filed on Dec. 20, 2019.

(51) Int. Cl.
*C07K 16/28* (2006.01)
*A61P 37/00* (2006.01)
*C07K 16/24* (2006.01)

(52) U.S. Cl.
CPC .......... *C07K 16/2866* (2013.01); *A61P 37/00* (2018.01); *C07K 16/244* (2013.01); *C07K 16/247* (2013.01); *C07K 2317/20* (2013.01); *C07K 2317/31* (2013.01); *C07K 2317/52* (2013.01); *C07K 2317/522* (2013.01); *C07K 2317/64* (2013.01)

(58) Field of Classification Search
CPC . C07K 16/2866; C07K 16/244; C07K 16/247
See application file for complete search history.

(56) References Cited

U.S. PATENT DOCUMENTS

| | | | |
|---|---|---|---|
| 4,816,567 | A | 3/1989 | Cabilly et al. |
| 6,946,292 | B2 | 9/2005 | Kanda et al. |
| 7,214,775 | B2 | 5/2007 | Hanai et al. |
| 7,696,222 | B2 | 4/2010 | Wang |
| 8,133,899 | B2 | 3/2012 | Mitton-Fry et al. |
| 8,546,422 | B2 | 10/2013 | Leblanc et al. |
| 8,637,541 | B2 | 1/2014 | Wang |
| 8,759,366 | B2 | 6/2014 | Childers et al. |
| 8,790,651 | B2 | 7/2014 | Bammert et al. |
| 8,987,283 | B2 | 3/2015 | Mitton-Fry et al. |
| 9,206,253 | B2 | 12/2015 | Bammert et al. |
| 10,093,731 | B2 | 10/2018 | Li et al. |
| 10,106,607 | B2 | 10/2018 | Morsey et al. |
| 11,897,960 | B2 | 2/2024 | Liu et al. |
| 2008/0160035 | A1 | 7/2008 | Stevens et al. |
| 2015/0017176 | A1 | 1/2015 | Kostic et al. |
| 2017/0275369 | A1 | 9/2017 | Bilsborough |
| 2018/0244766 | A1 | 8/2018 | Li et al. |
| 2018/0244767 | A1 | 8/2018 | Li et al. |
| 2018/0346580 | A1 | 12/2018 | Morsey et al. |

FOREIGN PATENT DOCUMENTS

| | | | |
|---|---|---|---|
| CN | 107683291 | A | 2/2018 |
| EA | 009026 | B1 | 10/2007 |
| RU | 2445318 | C2 | 3/2012 |
| RU | 2503460 | C2 | 1/2014 |
| RU | 2588462 | C2 | 6/2016 |
| RU | 2698907 | C2 | 9/2019 |
| WO | WO 2004085475 | A2 | 10/2004 |
| WO | WO 2004085476 | A2 | 10/2004 |
| WO | WO 2008054606 | A2 | 5/2008 |
| WO | WO 2009062102 | A2 | 5/2009 |
| WO | WO2010/031183 | A1 | 3/2010 |
| WO | 2010099039 | A1 | 9/2010 |
| WO | WO 2013011407 | A1 | 1/2013 |

(Continued)

OTHER PUBLICATIONS

Finkelshtein et al., 2012, "F59 Protein Physics: A Lecture Course with Color and Stereoscopic Illustrations and Problems," 4th ed., rev. and enl.—Moscow: KDU, 2012, p. 23, in Russian with machine English translation (4 pages).
Hlavacek et al., 1999, "Steric effects on multivalent ligand-receptor binding: exclusion of ligand sites by bound cell surface receptors," Biophys. J., 76(6):3031-3043.
Pluckthun et al., 1997, "New protein engineering approaches to multivalent and bispecific antibody fragments," Immunotechnology, 3(2):83-105.
Roitt et al., 1997, Chapter 9—Antigen Recognition from Immunology, Fifth Edition, Mosby International Ltd, p. 150 in Russian with English translation (8 pages).
World Health Organization (WHO), 2010, International Nonproprietary Names for Pharmaceutical Substances (INN), Recommended International Nonproprietary Names: List 63, WHO Drug Information, vol. 24, No. 1, pp. 41-80.

(Continued)

*Primary Examiner* — Prema M Mertz
(74) *Attorney, Agent, or Firm* — JONES DAY

(57) ABSTRACT

The present invention provides compositions for treating canine atopic dermatitis that comprise a caninized anti-proliferative antibody, a caninized anti-pruritic antibody, and a caninized anti-inflammatory antibody. The present invention further relates to compositions that comprise a bispecific antibody that comprises a caninized anti-pruritic antibody and a caninized anti-proliferative antibody or alternatively a bispecific antibody comprising a caninized anti-pruritic antibody and a caninized anti-inflammatory antibody.

6 Claims, 3 Drawing Sheets

Specification includes a Sequence Listing.

(56) References Cited

FOREIGN PATENT DOCUMENTS

| | | | |
|---|---|---|---|
| WO | WO 2014039461 | A1 | 3/2014 |
| WO | 2016156588 | A1 | 10/2016 |
| WO | 2017102920 | A1 | 6/2017 |
| WO | WO 2017186928 | A1 | 11/2017 |
| WO | 2018108969 | A1 | 6/2018 |
| WO | 2018156367 | A1 | 8/2018 |
| WO | WO 2018156180 | A1 | 8/2018 |
| WO | WO 2019200787 | A1 | 10/2019 |

OTHER PUBLICATIONS

Deev et al., 2009, "Modern technologies for creating non-natural antibodies for clinical use," J. of Nat., pp. 32-50, in Russian with machine English translation (38 pages).

Gorshkova et al., 2016, "Evolutionary Plasticity of IL-6 Cytokine Family," Molecular Biology, 50(6):1039-1048, in Russian with machine English translation (20 pages).

Singer et al., 1998, "Genes and Genomes," Moscow, Mir, translation from English, 1:63-64, in Russian with machine English translation (8 pages).

Baert et al., Influence of Immunogenicity on the long term efficacy of Infliximab in Crohns disease, New England Journal Med., 2003, pp. 601-608, 348.

Beniaminovitz et al., Prevention of rejection in cardiac transplantation by blockade of the interleukin 2 receptor with a monoclonal antibody, New England Journal of Medicine, 2000, pp. 613-619, 342.

Bergeron et al., Comparative functional characterization of canine IgG subclasses, Veterinary Immunology and Immunopathology, 2014, pp. 31-41, 157.

Chothia and Lesk et al., Canonical Structures for the Hypervariable Regions of Immunoglobins, J. Mol. Biol., 1987, 901-917, 196.

Chothia et al., Conformations of immunoglobin hypervariable regions, Nature, 1989, 877-883, 342.

Gelebart, Pascal and Lai, Raymond, IL22RA1 (interleukin 22 receptor, alpha 1), Atlas of Genetics and Cytogenetics in Oncology and Haematology, 2010, 1106-1110, 14(12).

Ghosh et al., Natalizumab for active Crohns disease, New England J. Med., 2003, pp. 24-32, 348.

Guttman-Yassky, Emma et al., Efficacy and safety of fezakinumab (an IL-22 monoclonal antibody) in adults with moderate-to-severe atopic dermatitis inadequately controlled by conventional treatments: A randomized, double-blind, phase 2a trial, Journal of the American Academy of Dermatology, 2018, 872-881, 78(5).

Harskamp et al., Immunology of Atopic Dermatitis: Novel Insights into Mechanisms and Immunomodulatory Therapies, Seminars in Cutaneous Medicine and Surgery, 2013, 132-139, 32.

Huber, Samuel et al., IL-22BP is regulated by the inflammasome and modulates tumorigenesis in the intestine, Nature, 2012, 259-263, 491.

Kabat, the Structural Basis of Antibody Complementarity, Adv. Prot. Chem., 1978, 1-75, 32.

Kabat, Unusual Distributions of Amino Acids in Complementarity-determining (Hypervriable) Segment of Heavy and Light Chains of Immunoglobulins and Their Possible Roles in Specificity of Antibody-combining Sites, J. Biol. Chem., 1977, 6609-6616, 252.

Klein, Christian et al., Engineering therapeutic bispecific antibodies using CrossMab technology, Methods, 2019, 21-23, 154.

Klein, Christian et al., The use of CrossMAb technology for the generation of bi- and multispecific antibodies, MABS, 2016, 1010-1020, 8.

Lee, Donna W. et al., Nonclinical safety assessment of a human interleukin-22FC IG fusion protein demonstrates in vitro to in vivo and cross-species translatability, Pharmacol Res Perspect., 2018, 1-13, e00434.

Lipsky et al., Infliximab and methotrexate in the treatment of rheumatoid arthritis, New England Journal of Medicine, 2000, pp. 1594-1602, 343.

Milgrom et al., Treatment of allergic asthma with monoclonal anti IgE antibody, New England Journal Med., 1999, pp. 1966-1973, 341.

Morrison, Sherie L. et al., Chimeric human antibody molecules: Mouse antigen-binding domains with human constant region domains, Proc. Natl. Acad. Sci. USA, 1984, 6851-6855, 81.

Nuttall et al., Canine Atopic Dermatitis—what have we learned?, Veterinary Record, 2013, 201-207, 172(8).

Rahman et al., The Pathology and Immunology of Atopic Dermatitis, Inflammation & Allergy—Drug Targets, 2011, 486-496, 10.

Ruzicka, Thomas et al., Anti-Interleukin-31 Receptor A Antibody for Atopic Dermatitis, The New England Journal of Medicine, 2017, 826-835, 376(9).

Schaefer, Wolfgang et al., Immunoglobulin domain crossover as a generic approach for the production of bispecific IgG antibodies, PNAS, 2011, 11187-11192, 108.

Shinkawa et al., The absence of fucose but not the presence of galactose or bisecting N acetylglucosamine of human IgG1 complex type oligosaccharide shows the critical role of enhancing antibody dependent cellular cytotoxicity, J. Biol. Chem., 2003, pp. 3466-3473, 278.

Slamon et al., Use of chemotherapy plus a monoclonal antibody against HER2 for metastatic breast cancer that overexpresses HER2, New England J. Med., 2001, pp. 783-792, 344.

Tang et al., Cloning and characterization of cDNAs encoding four different canine immunoglobulin Y chains, Veterinary Immunology and Immunopathology, 2001, pp. 259-270, 80.

Xu, Wenfeng et al., A soluble class II cytokine receptor, IL-22RA2, is a naturally occurring IL-22 antagonist, PNAS, 2001, 9511-9516, vol. 98 | No. 17.

Marsella et al., 2012, "Current understanding of the pathophysiologic mechanisms of canine atopic dermatitis," J. Am. Vet. Med. Assoc., 241(2):194-207.

Figure 1. Binding of canine IL-22 to anti-canine IL-22 antibody
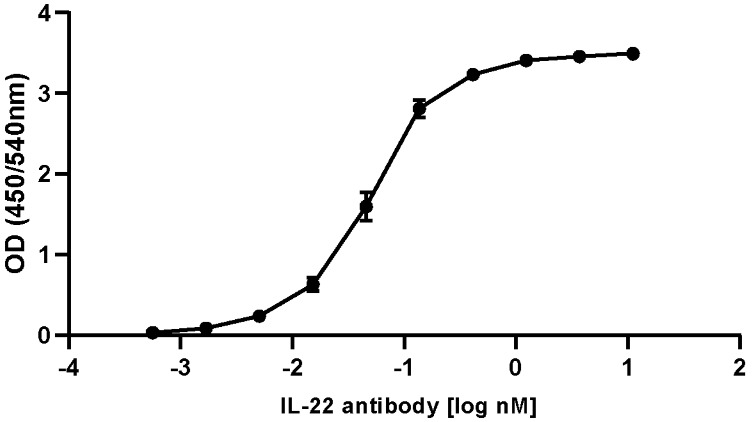
Figure 2. Inhibition of IL-4 mediated STAT-6 phosphorylation by antibodies to canine IL-4 receptor alpha
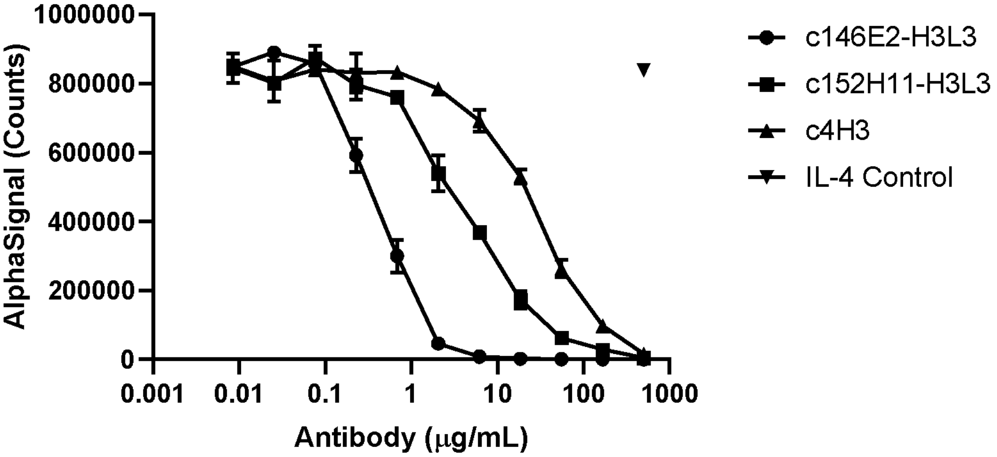

Figure 3. Inhibition of IL-13-mediated STAT-6 phosphorylation by antibodies to canine IL-4 receptor alpha
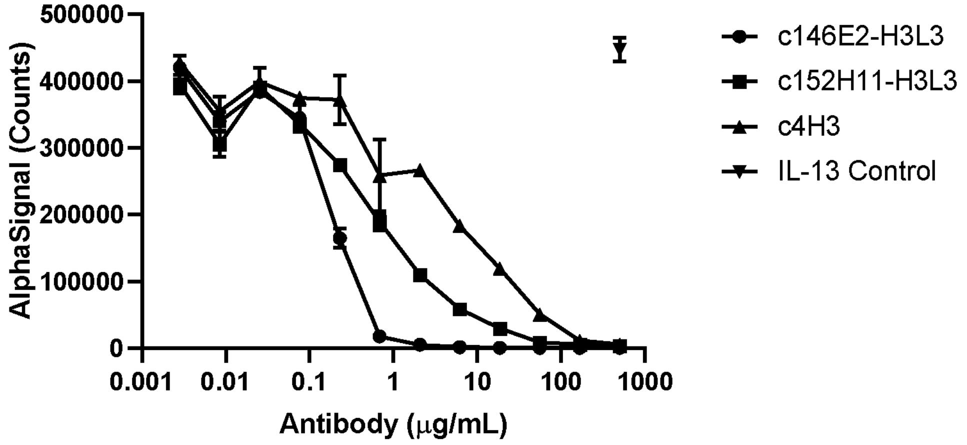

Figure 4. Binding of biotinylated canine IL-31 to extracellular domain of canine IL-31R
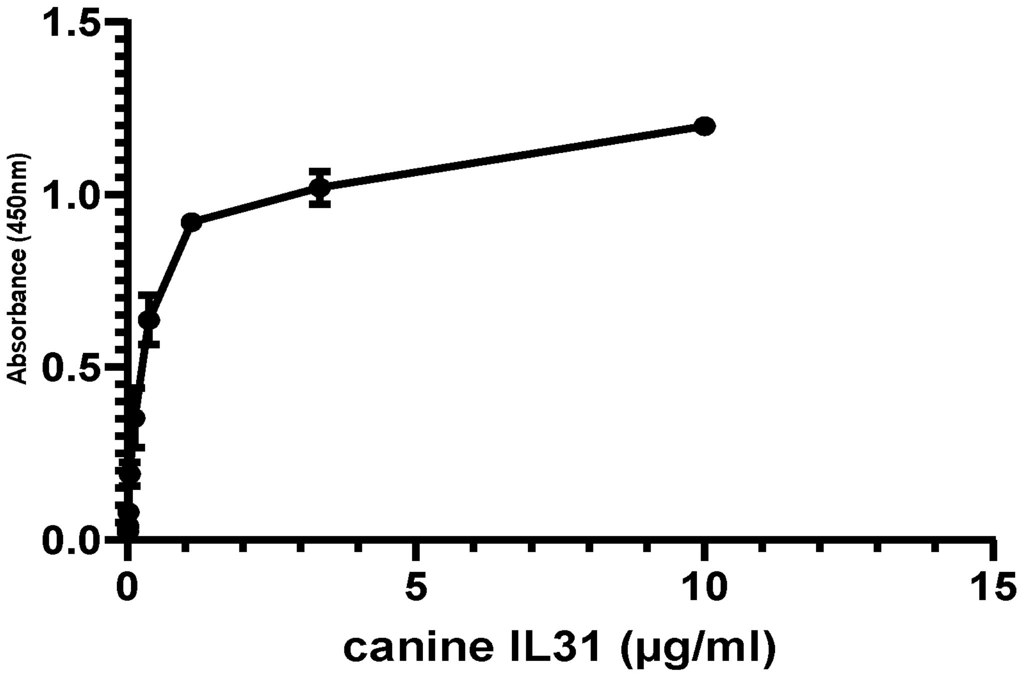

SEQUENCE LISTING

<160> NUMBER OF SEQ ID NOS: 50

<210> SEQ ID NO 1
<211> LENGTH: 152
<212> TYPE: PRT
<213> ORGANISM: Artificial Sequence
<220> FEATURE:
<223> OTHER INFORMATION: canine and HIS Tag

<400> SEQUENCE: 1

Leu Pro Ile Ser Ser His Cys Arg Leu Asp Lys Ser Asn Phe Gln Gln
1 5 10 15

Pro Tyr Ile Thr Asn Arg Thr Phe Met Leu Ala Lys Glu Ala Ser Leu
20 25 30

Ala Asp Asn Asn Thr Asp Val Arg Leu Ile Gly Glu Lys Leu Phe His
35 40 45

Gly Val Asn Met Gly Glu Arg Cys Tyr Leu Met Lys Glu Val Leu Asn
50 55 60

Phe Thr Leu Glu Glu Val Leu Leu Pro Gln Ser Asp Arg Phe Gln Pro
65 70 75 80

Tyr Met Gln Glu Val Val Pro Phe Leu Ala Arg Leu Ser Asn Lys Leu
85 90 95

Ser Gln Cys His Ile Glu Asn Asp Asp Gln His Ile Gln Arg Asn Val
100 105 110

Gln Lys Leu Lys Asp Thr Val Gln Lys Leu Gly Glu Asn Gly Glu Ile
115 120 125

Lys Ala Ile Gly Glu Leu Asp Leu Leu Phe Met Ala Leu Arg Asn Ala
130 135 140

Cys Val His His His His His His
145 150

<210> SEQ ID NO 2
<211> LENGTH: 449
<212> TYPE: PRT
<213> ORGANISM: Homo sapiens

<400> SEQUENCE: 2

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Tyr Met His Trp Val Arg Gln Ala Pro Gly Gln Gly Leu Glu Trp Val
35 40 45

Gly Trp Ile Asn Pro Tyr Thr Gly Ser Ala Phe Tyr Ala Gln Lys Phe
50 55 60

Arg Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Glu Pro Glu Lys Phe Asp Ser Asp Asp Ser Asp Val Trp Gly
100 105 110

Arg Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Lys Val Glu Pro Lys Ser Cys
210 215 220

Asp Lys Thr His Thr Cys Pro Pro Cys Pro Ala Pro Glu Leu Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Pro Ala Pro Ile
325 330 335

Glu Lys Thr Ile Ser Lys Ala Lys Gly Gln Pro Arg Glu Pro Gln Val
340 345 350

Tyr Thr Leu Pro Pro Ser Arg Glu Glu Met Thr Lys Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 3
<211> LENGTH: 217
<212> TYPE: PRT
<213> ORGANISM: Homo sapiens

<400> SEQUENCE: 3

Gln Ala Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Gly Val His Trp Tyr Gln Gln Leu Pro Gly Thr Ala Pro Lys Leu
        35                  40                  45

Leu Ile Tyr Gly Asp Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Asn Ser
                85                  90                  95

Leu Ser Gly Tyr Val Phe Gly Gly Gly Thr Gln Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 4
<211> LENGTH: 217
<212> TYPE: PRT
<213> ORGANISM: Artificial Sequence
<220> FEATURE:
<223> OTHER INFORMATION: canine and mouse

<400> SEQUENCE: 4

Glu Ile Val Met Thr Gln Ser Pro Ala Ser Leu Ser Leu Ser Gln Glu
1               5                   10                  15

Glu Lys Val Thr Ile Thr Cys Lys Ala Ser Gln Asn Val Gly Thr Asn
            20                  25                  30

Val Ala Trp Tyr Gln Gln Lys Pro Gly Gln Ala Pro Lys Leu Leu Ile
        35                  40                  45

Tyr Ser Ala Ser Tyr Arg Tyr Ser Gly Leu Pro Asp Arg Phe Ser Gly
    50                  55                  60

Ser Gly Ser Gly Thr Asp Phe Ser Phe Thr Ile Ser Ser Leu Glu Pro
65                  70                  75                  80

Glu Asp Val Ala Glu Phe Phe Cys Gln Gln Tyr Asn Ser Tyr Pro Tyr
                85                  90                  95

Thr Phe Gly Gln Gly Thr Lys Leu Glu Ile Lys Arg Asn Asp Ala Gln
            100                 105                 110

Pro Ala Val Tyr Leu Phe Gln Pro Ser Pro Asp Gln Leu His Thr Gly
        115                 120                 125

```
Ser Ala Ser Val Val Cys Leu Leu Asn Ser Phe Tyr Pro Lys Asp Ile
    130                 135                 140

Asn Val Lys Trp Lys Val Asp Gly Val Ile Gln Asp Thr Gly Ile Gln
145                 150                 155                 160

Glu Ser Val Thr Glu Gln Asp Lys Asp Ser Thr Tyr Ser Leu Ser Ser
                165                 170                 175

Thr Leu Thr Met Ser Ser Thr Glu Tyr Leu Ser His Glu Leu Tyr Ser
            180                 185                 190

Cys Glu Ile Thr His Lys Ser Leu Pro Ser Thr Leu Ile Lys Ser Phe
        195                 200                 205

Gln Arg Ser Glu Cys Gln Arg Val Asp
    210                 215


<210> SEQ ID NO 5
<211> LENGTH: 453
<212> TYPE: PRT
<213> ORGANISM: Artificial Sequence
<220> FEATURE:
<223> OTHER INFORMATION: modified canine and mouse

<400> SEQUENCE: 5

Glu Val Gln Leu Val Glu Ser Gly Gly Asp Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Asp Lys Arg Leu Gln Trp Val
        35                  40                  45

Ala Thr Ile Ser Arg Gly Gly Asp Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Gly Thr Leu Asn Asn Arg Gly Phe Ala Ser Trp Gly Gln Gly
            100                 105                 110

Thr Leu Val Thr Val Ser Ser Ala Ser Thr Thr Ala Pro Ser Val Phe
        115                 120                 125

Pro Leu Ala Pro Ser Cys Gly Ser Thr Ser Gly Ser Thr Val Ala Leu
    130                 135                 140

Ala Cys Leu Val Ser Gly Tyr Phe Pro Glu Pro Val Thr Val Ser Trp
145                 150                 155                 160

Asn Ser Gly Ser Leu Thr Ser Gly Val His Thr Phe Pro Ser Val Leu
                165                 170                 175

Gln Ser Ser Gly Leu Tyr Ser Leu Ser Ser Met Val Thr Val Pro Ser
            180                 185                 190

Ser Arg Trp Pro Ser Glu Thr Phe Thr Cys Asn Val Ala His Pro Ala
        195                 200                 205

Ser Lys Thr Lys Val Asp Lys Pro Val Pro Lys Arg Glu Asn Gly Arg
    210                 215                 220

Val Pro Arg Pro Pro Asp Cys Pro Lys Cys Pro Ala Pro Glu Met Leu
225                 230                 235                 240

Gly Gly Pro Ser Val Phe Ile Phe Pro Pro Lys Pro Lys Asp Thr Leu
                245                 250                 255

Leu Ile Ala Arg Thr Pro Glu Val Thr Cys Val Val Val Ala Leu Asp
            260                 265                 270
```

-continued

Pro Glu Asp Pro Glu Val Gln Ile Ser Trp Phe Val Asp Gly Lys Gln
275 280 285

Met Gln Thr Ala Lys Thr Gln Pro Arg Glu Glu Gln Phe Ala Gly Thr
290 295 300

Tyr Arg Val Val Ser Val Leu Pro Ile Gly His Gln Asp Trp Leu Lys
305 310 315 320

Gly Lys Gln Phe Thr Cys Lys Val Asn Asn Lys Ala Leu Pro Ser Pro
325 330 335

Ile Glu Arg Thr Ile Ser Lys Ala Arg Gly Gln Ala His Gln Pro Ser
340 345 350

Val Tyr Val Leu Pro Pro Ser Arg Glu Glu Leu Ser Lys Asn Thr Val
355 360 365

Ser Leu Thr Cys Leu Ile Lys Asp Phe Phe Pro Pro Asp Ile Asp Val
370 375 380

Glu Trp Gln Ser Asn Gly Gln Gln Glu Pro Glu Ser Lys Tyr Arg Thr
385 390 395 400

Thr Pro Pro Gln Leu Asp Glu Asp Gly Ser Tyr Phe Leu Tyr Ser Lys
405 410 415

Leu Ser Val Asp Lys Ser Arg Trp Gln Arg Gly Asp Thr Phe Ile Cys
420 425 430

Ala Val Met His Glu Ala Leu His Asn His Tyr Thr Gln Glu Ser Leu
435 440 445

Ser His Ser Pro Gly
450

<210> SEQ ID NO 6
<211> LENGTH: 221
<212> TYPE: PRT
<213> ORGANISM: Artificial Sequence
<220> FEATURE:
<223> OTHER INFORMATION: canine and mouse

<400> SEQUENCE: 6

Asp Ile Val Leu Thr Gln Thr Pro Leu Ser Leu Ser Val Ser Pro Gly
1 5 10 15

Glu Thr Ala Ser Ile Tyr Cys Arg Ala Ser Glu Ser Val Asp Ser Tyr
20 25 30

Gly Asn Ser Phe Leu Asn Trp Tyr Gln Gln Lys Pro Gly Gln Pro Pro
35 40 45

Lys Leu Leu Ile Tyr Arg Ala Ser Asn Leu Ala Ser Glu Ile Pro Asp
50 55 60

Arg Phe Ser Gly Ser Gly Ser Arg Thr Glu Phe Thr Leu Lys Ile Ser
65 70 75 80

Arg Val Glu Ala Asp Asp Ala Gly Val Tyr Tyr Cys Gln Gln Asn Tyr
85 90 95

Glu Asn Pro Arg Thr Phe Gly Gln Gly Thr Lys Leu Glu Ile Lys Arg
100 105 110

Asn Asp Ala Gln Pro Ala Val Tyr Leu Phe Gln Pro Ser Pro Asp Gln
115 120 125

Leu His Thr Gly Ser Ala Ser Val Val Cys Leu Leu Asn Ser Phe Tyr
130 135 140

Pro Lys Asp Ile Asn Val Lys Trp Lys Val Asp Gly Val Ile Gln Asp
145 150 155 160

Thr Gly Ile Gln Glu Ser Val Thr Glu Gln Asp Lys Asp Ser Thr Tyr
165 170 175

-continued

```
Ser Leu Ser Ser Thr Leu Thr Met Ser Ser Thr Glu Tyr Leu Ser His
            180                 185                 190

Glu Leu Tyr Ser Cys Glu Ile Thr His Lys Ser Leu Pro Ser Thr Leu
        195                 200                 205

Ile Lys Ser Phe Gln Arg Ser Glu Cys Gln Arg Val Asp
    210                 215                 220


<210> SEQ ID NO 7
<211> LENGTH: 451
<212> TYPE: PRT
<213> ORGANISM: Artificial Sequence
<220> FEATURE:
<223> OTHER INFORMATION: modified canine and mouse

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Arg Tyr
            20                  25                  30

Trp Met His Trp Met Lys Gln Ala Pro Gly Ala Gly Leu Asp Trp Ile
        35                  40                  45

Gly Met Ile His Pro Asp Ser Gly Asn Ile Asn Tyr Asn Glu Arg Phe
    50                  55                  60

Lys Thr Lys Ala Thr Leu Thr Val Asp Lys Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gln Leu Arg Asn Ala Met Asp Tyr Trp Gly Gln Gly Thr Leu
            100                 105                 110

Val Thr Val Ser Ser Ala Ser Thr Thr Ala Pro Ser Val Phe Pro Leu
        115                 120                 125

Ala Pro Ser Cys Gly Ser Thr Ser Gly Ser Thr Val Ala Leu Ala Cys
    130                 135                 140

Leu Val Ser Gly Tyr Phe Pro Glu Pro Val Thr Val Ser Trp Asn Ser
145                 150                 155                 160

Gly Ser Leu Thr Ser Gly Val His Thr Phe Pro Ser Val Leu Gln Ser
                165                 170                 175

Ser Gly Leu Tyr Ser Leu Ser Ser Met Val Thr Val Pro Ser Ser Arg
            180                 185                 190

Trp Pro Ser Glu Thr Phe Thr Cys Asn Val Ala His Pro Ala Ser Lys
        195                 200                 205

Thr Lys Val Asp Lys Pro Val Pro Lys Arg Glu Asn Gly Arg Val Pro
    210                 215                 220

Arg Pro Pro Asp Cys Pro Lys Cys Pro Ala Pro Glu Met Leu Gly Gly
225                 230                 235                 240

Pro Ser Val Phe Ile Phe Pro Pro Lys Pro Lys Asp Thr Leu Leu Ile
                245                 250                 255

Ala Arg Thr Pro Glu Val Thr Cys Val Val Val Ala Leu Asp Pro Glu
            260                 265                 270

Asp Pro Glu Val Gln Ile Ser Trp Phe Val Asp Gly Lys Gln Met Gln
        275                 280                 285

Thr Ala Lys Thr Gln Pro Arg Glu Glu Gln Phe Ala Gly Thr Tyr Arg
    290                 295                 300

Val Val Ser Val Leu Pro Ile Gly His Gln Asp Trp Leu Lys Gly Lys
305                 310                 315                 320
```

-continued

```
Gln Phe Thr Cys Lys Val Asn Asn Lys Ala Leu Pro Ser Pro Ile Glu
                325                 330                 335

Arg Thr Ile Ser Lys Ala Arg Gly Gln Ala His Gln Pro Ser Val Tyr
            340                 345                 350

Val Leu Pro Pro Ser Arg Glu Glu Leu Ser Lys Asn Thr Val Ser Leu
        355                 360                 365

Thr Cys Leu Ile Lys Asp Phe Phe Pro Pro Asp Ile Asp Val Glu Trp
    370                 375                 380

Gln Ser Asn Gly Gln Gln Glu Pro Glu Ser Lys Tyr Arg Thr Thr Pro
385                 390                 395                 400

Pro Gln Leu Asp Glu Asp Gly Ser Tyr Phe Leu Tyr Ser Lys Leu Ser
                405                 410                 415

Val Asp Lys Ser Arg Trp Gln Arg Gly Asp Thr Phe Ile Cys Ala Val
            420                 425                 430

Met His Glu Ala Leu His Asn His Tyr Thr Gln Glu Ser Leu Ser His
        435                 440                 445

Ser Pro Gly
    450


<210> SEQ ID NO 8
<211> LENGTH: 1521
<212> TYPE: DNA
<213> ORGANISM: Artificial Sequence
<220> FEATURE:
<223> OTHER INFORMATION: canine and HIS Tag

<400> SEQUENCE: 8

gtgctgcccg ccaagcccga gaacatcagc tgcatcttct actacgagga gaacttcacc     60

tgcacctgga gccccgagaa ggaggccagc tacacctggt acaaggtgaa gagaacctac    120

agctacggct acaagagcga catctgcagc accgacaaca gcaccagagg caaccacgcc    180

agctgcagct tcctgccccc caccatcacc aaccccgaca actacaccat ccaggtggag    240

gcccagaacg ccgacggcat catgaagagc gacatcacct actggaacct ggacgccatc    300

atgaagatcg agcccccga gatcttcagc gtgaagagcg tgctgggcat caagagaatg    360

ctgcagatca agtggatcag acccgtgctg gcccccaca gcagcaccct gaagtacacc    420

ctgagattca gaaccatcaa cagcgcctac tggatggagg tgaacttcac caaggaggac    480

atcgacagag acgagaccta caacctgacc gagctgcagg ccttcaccga gtacgtgatg    540

accctgagat gcgcccccgc cgagagcatg ttctggagcg gctggagcca ggagaaggtg    600

ggcaccaccg aggaggaggc cccctacggc ctggacctgt ggagagtgct gaagcccgcc    660

atggtggacg gcagaagacc cgtgcagctg atgtggaaga aggccaccgg cgcccccgtg    720

ctggagaagg ccctgggcta caacatctgg tacttccccg agaacaacac caacctgacc    780

gagaccgtga acaccaccaa ccagacccac gagctgtacc tgggcggcaa gacctactgg    840

gtgtacgtgg tgagctacaa cagcctgggc gagagccccg tggccaccct gagaatcccc    900

gccctgaacg agaagacctt ccagtgcatc gaggccatgc aggcctgcct gacccaggac    960

cagctggtgg tggagtggca gagcagcgcc cccgaggtgg acacctggat ggtggagtgg   1020

ttccccgacg tggacagcga gcccagcagc ttcagctggg agagcgtgag ccaggccaga   1080

aactggacca tccagaagga cgagctgaag cccctgtggt gctacaacat cagcgtgtac   1140

cccgtgctga gagacagagt gggccagccc tacagcaccc aggcctacgt gcaggagggc   1200

atccccagcg ccggccccgt gacccaggcc gacagcatcg gcgtgaagac cgtgaccatc   1260
```

```
acctggaagg agatccccaa gagcaagaga aacggcttca tcaagaacta caccatcttc   1320

taccaggccg aggacggcaa ggagttcagc aagaccgtga acagcaacat cctgcagtac   1380

agactggaga gcctgaccag aagaaccagc tacagcctgc aggtgatggc cagcaccaac   1440

gccggcggca ccaacggcac caagatcaac ttcaagaccc tgagcatcag ccaccaccac   1500

caccaccacc accaccacca c                                             1521


<210> SEQ ID NO 9
<211> LENGTH: 507
<212> TYPE: PRT
<213> ORGANISM: Artificial Sequence
<220> FEATURE:
<223> OTHER INFORMATION: canine and HIS Tag

<400> SEQUENCE: 9

Val Leu Pro Ala Lys Pro Glu Asn Ile Ser Cys Ile Phe Tyr Tyr Glu
1               5                   10                  15

Glu Asn Phe Thr Cys Thr Trp Ser Pro Glu Lys Glu Ala Ser Tyr Thr
            20                  25                  30

Trp Tyr Lys Val Lys Arg Thr Tyr Ser Tyr Gly Tyr Lys Ser Asp Ile
        35                  40                  45

Cys Ser Thr Asp Asn Ser Thr Arg Gly Asn His Ala Ser Cys Ser Phe
    50                  55                  60

Leu Pro Pro Thr Ile Thr Asn Pro Asp Asn Tyr Thr Ile Gln Val Glu
65                  70                  75                  80

Ala Gln Asn Ala Asp Gly Ile Met Lys Ser Asp Ile Thr Tyr Trp Asn
                85                  90                  95

Leu Asp Ala Ile Met Lys Ile Glu Pro Pro Glu Ile Phe Ser Val Lys
            100                 105                 110

Ser Val Leu Gly Ile Lys Arg Met Leu Gln Ile Lys Trp Ile Arg Pro
        115                 120                 125

Val Leu Ala Pro His Ser Ser Thr Leu Lys Tyr Thr Leu Arg Phe Arg
    130                 135                 140

Thr Ile Asn Ser Ala Tyr Trp Met Glu Val Asn Phe Thr Lys Glu Asp
145                 150                 155                 160

Ile Asp Arg Asp Glu Thr Tyr Asn Leu Thr Glu Leu Gln Ala Phe Thr
                165                 170                 175

Glu Tyr Val Met Thr Leu Arg Cys Ala Pro Ala Glu Ser Met Phe Trp
            180                 185                 190

Ser Gly Trp Ser Gln Glu Lys Val Gly Thr Thr Glu Glu Glu Ala Pro
        195                 200                 205

Tyr Gly Leu Asp Leu Trp Arg Val Leu Lys Pro Ala Met Val Asp Gly
    210                 215                 220

Arg Arg Pro Val Gln Leu Met Trp Lys Lys Ala Thr Gly Ala Pro Val
225                 230                 235                 240

Leu Glu Lys Ala Leu Gly Tyr Asn Ile Trp Tyr Phe Pro Glu Asn Asn
                245                 250                 255

Thr Asn Leu Thr Glu Thr Val Asn Thr Thr Asn Gln Thr His Glu Leu
            260                 265                 270

Tyr Leu Gly Gly Lys Thr Tyr Trp Val Tyr Val Val Ser Tyr Asn Ser
        275                 280                 285

Leu Gly Glu Ser Pro Val Ala Thr Leu Arg Ile Pro Ala Leu Asn Glu
    290                 295                 300

Lys Thr Phe Gln Cys Ile Glu Ala Met Gln Ala Cys Leu Thr Gln Asp
305                 310                 315                 320
```

Gln Leu Val Val Glu Trp Gln Ser Ser Ala Pro Glu Val Asp Thr Trp
325 330 335

Met Val Glu Trp Phe Pro Asp Val Asp Ser Glu Pro Ser Ser Phe Ser
340 345 350

Trp Glu Ser Val Ser Gln Ala Arg Asn Trp Thr Ile Gln Lys Asp Glu
355 360 365

Leu Lys Pro Leu Trp Cys Tyr Asn Ile Ser Val Tyr Pro Val Leu Arg
370 375 380

Asp Arg Val Gly Gln Pro Tyr Ser Thr Gln Ala Tyr Val Gln Glu Gly
385 390 395 400

Ile Pro Ser Ala Gly Pro Val Thr Gln Ala Asp Ser Ile Gly Val Lys
405 410 415

Thr Val Thr Ile Thr Trp Lys Glu Ile Pro Lys Ser Lys Arg Asn Gly
420 425 430

Phe Ile Lys Asn Tyr Thr Ile Phe Tyr Gln Ala Glu Asp Gly Lys Glu
435 440 445

Phe Ser Lys Thr Val Asn Ser Asn Ile Leu Gln Tyr Arg Leu Glu Ser
450 455 460

Leu Thr Arg Arg Thr Ser Tyr Ser Leu Gln Val Met Ala Ser Thr Asn
465 470 475 480

Ala Gly Gly Thr Asn Gly Thr Lys Ile Asn Phe Lys Thr Leu Ser Ile
485 490 495

Ser His His His His His His His His His His
500 505

<210> SEQ ID NO 10
<211> LENGTH: 451
<212> TYPE: PRT
<213> ORGANISM: Artificial Sequence
<220> FEATURE:
<223> OTHER INFORMATION: canine and mouse

<400> SEQUENCE: 10

Glu Val Gln Leu Val Glu Ser Gly Pro Ser Leu Val Lys Pro Gly Gly
1 5 10 15

Ser Leu Arg Leu Thr Cys Ser Val Thr Gly Asp Ser Ile Thr Ser Gly
20 25 30

Tyr Trp Asn Trp Ile Arg Lys Phe Pro Gly Asn Lys Leu Glu Tyr Met
35 40 45

Gly Tyr Ile Ser Tyr Ser Gly Ile Thr Asp Tyr Asn Pro Ser Leu Lys
50 55 60

Ser Arg Ile Thr Ile Ser Arg Asp Thr Ser Lys Asn Gln Tyr Tyr Leu
65 70 75 80

Gln Leu Asn Ser Val Thr Thr Glu Asp Thr Ala Thr Tyr Tyr Cys Ala
85 90 95

Arg Tyr Gly Asn Tyr Gly Tyr Ala Met Asp Tyr Trp Gly Gln Gly Thr
100 105 110

Leu Val Thr Val Ser Ser Ala Ser Thr Thr Ala Pro Ser Val Phe Pro
115 120 125

Leu Ala Pro Ser Cys Gly Ser Thr Ser Gly Ser Thr Val Ala Leu Ala
130 135 140

Cys Leu Val Ser Gly Tyr Phe Pro Glu Pro Val Thr Val Ser Trp Asn
145 150 155 160

Ser Gly Ser Leu Thr Ser Gly Val His Thr Phe Pro Ser Val Leu Gln
165 170 175

Ser Ser Gly Leu Tyr Ser Leu Ser Ser Met Val Thr Val Pro Ser Ser
180 185 190

Arg Trp Pro Ser Glu Thr Phe Thr Cys Asn Val Ala His Pro Ala Ser
195 200 205

Lys Thr Lys Val Asp Lys Pro Val Pro Lys Arg Glu Asn Gly Arg Val
210 215 220

Pro Arg Pro Pro Asp Cys Pro Lys Cys Pro Ala Pro Glu Met Leu Gly
225 230 235 240

Gly Pro Ser Val Phe Ile Phe Pro Pro Lys Pro Lys Asp Thr Leu Leu
245 250 255

Ile Ala Arg Thr Pro Glu Val Thr Cys Val Trp Asp Leu Asp Pro Glu
260 265 270

Asp Pro Glu Val Gln Ile Ser Trp Phe Val Asp Gly Lys Gln Met Gln
275 280 285

Thr Ala Lys Thr Gln Pro Arg Glu Glu Gln Phe Ala Gly Thr Tyr Arg
290 295 300

Trp Ser Val Leu Pro Ile Gly His Gln Asp Trp Leu Lys Gly Lys Gln
305 310 315 320

Phe Thr Cys Lys Val Asn Asn Lys Ala Leu Pro Ser Pro Ile Glu Arg
325 330 335

Thr Ile Ser Lys Ala Arg Gly Gln Ala His Gln Pro Ser Val Tyr Val
340 345 350

Leu Pro Pro Ser Arg Glu Glu Leu Ser Lys Asn Thr Val Ser Leu Thr
355 360 365

Cys Leu Ile Lys Asp Phe Phe Pro Pro Asp Ile Asp Val Glu Trp Gln
370 375 380

Ser Asn Gly Gln Gln Glu Pro Glu Ser Lys Tyr Arg Thr Thr Pro Pro
385 390 395 400

Gln Leu Asp Glu Asp Gly Ser Tyr Phe Leu Tyr Ser Lys Leu Ser Val
405 410 415

Asp Lys Ser Arg Trp Gln Arg Gly Asp Thr Phe Ile Cys Ala Val Met
420 425 430

His Glu Ala Leu His Asn His Tyr Thr Gln Glu Ser Leu Ser His Ser
435 440 445

Pro Gly Lys
450

<210> SEQ ID NO 11
<211> LENGTH: 220
<212> TYPE: PRT
<213> ORGANISM: Artificial Sequence
<220> FEATURE:
<223> OTHER INFORMATION: canine and mouse

<400> SEQUENCE: 11

Asp Ile Val Met Thr Gln Ser Pro Ala Ser Leu Ser Val Ser Leu Gly
1 5 10 15

Gln Arg Ala Thr Ile Ser Cys Arg Ala Ser Glu Ser Val Asp Thr Tyr
20 25 30

Gly Asn Ser Phe Met His Trp Tyr Gln Gln Lys Pro Gly Gln Ser Pro
35 40 45

Lys Leu Leu Ile Tyr Arg Ala Ser Asn Leu Glu Ser Gly Ile Pro Ala
50 55 60

Arg Phe Gly Gly Ser Gly Ser Gly Thr Asp Phe Thr Leu Thr Ile Asp
65 70 75 80

```
Pro Val Gln Ala Asp Asp Val Ala Thr Tyr Tyr Cys Gln Gln Ser Tyr
                85                  90                  95

Glu Asp Pro Trp Thr Phe Gly Gly Gly Thr Lys Leu Glu Ile Lys Arg
            100                 105                 110

Asn Asp Ala Gln Pro Ala Val Tyr Leu Phe Gln Pro Ser Pro Asp Gln
        115                 120                 125

Leu His Thr Gly Ser Ala Ser Trp Cys Leu Leu Asn Ser Phe Tyr Pro
    130                 135                 140

Lys Asp Ile Asn Val Lys Trp Lys Val Asp Gly Val Ile Gln Asp Thr
145                 150                 155                 160

Gly Ile Gln Glu Ser Val Thr Glu Gln Asp Lys Asp Ser Thr Tyr Ser
                165                 170                 175

Leu Ser Ser Thr Leu Thr Met Ser Ser Thr Glu Tyr Leu Ser His Glu
            180                 185                 190

Leu Tyr Ser Cys Glu Ile Thr His Lys Ser Leu Pro Ser Thr Leu Ile
        195                 200                 205

Lys Ser Phe Gln Arg Ser Glu Cys Gln Arg Val Asp
    210                 215                 220


<210> SEQ ID NO 12
<211> LENGTH: 217
<212> TYPE: PRT
<213> ORGANISM: Artificial Sequence
<220> FEATURE:
<223> OTHER INFORMATION: canine and mouse

<400> SEQUENCE: 12

Glu Ile Val Met Thr Gln Ser Pro Ala Ser Leu Ser Leu Ser Gln Glu
1               5                   10                  15

Glu Lys Val Thr Ile Thr Cys Lys Ala Ser Gln Ser Val Ser Phe Ala
            20                  25                  30

Gly Thr Gly Leu Met His Trp Tyr Gln Gln Lys Pro Gly Gln Ala Pro
        35                  40                  45

Lys Leu Leu Ile Tyr Arg Ala Ser Asn Leu Glu Ala Gly Val Pro Ser
    50                  55                  60

Arg Phe Ser Gly Ser Gly Ser Gly Thr Asp Phe Ser Phe Thr Ile Ser
65                  70                  75                  80

Ser Leu Glu Pro Glu Asp Val Ala Val Tyr Tyr Cys Gln Gln Ser Arg
                85                  90                  95

Glu Tyr Pro Trp Thr Phe Gly Gln Gly Thr Lys Leu Glu Ile Lys Arg
            100                 105                 110

Asn Asp Ala Gln Pro Ala Val Tyr Leu Phe Gln Pro Ser Pro Asp Gln
        115                 120                 125

Leu His Thr Gly Ser Ala Ser Val Val Cys Leu Leu Asn Ser Phe Tyr
    130                 135                 140

Pro Lys Asp Ile Asn Val Lys Trp Lys Val Asp Gly Val Ile Gln Asp
145                 150                 155                 160

Thr Gly Ile Gln Glu Ser Val Thr Glu Gln Asp Lys Asp Ser Thr Tyr
                165                 170                 175

Ser Leu Ser Ser Thr Leu Thr Met Ser Ser Thr Glu Tyr Leu Ser His
            180                 185                 190

Glu Leu Tyr Ser Cys Glu Ile Thr His Lys Ser Leu Pro Ser Thr Leu
        195                 200                 205

Ile Lys Ser Phe Gln Arg Ser Glu Cys
    210                 215
```

-continued

<210> SEQ ID NO 13
<211> LENGTH: 452
<212> TYPE: PRT
<213> ORGANISM: Artificial Sequence
<220> FEATURE:
<223> OTHER INFORMATION: canine and mouse

<400> SEQUENCE: 13

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asn Tyr
            20                  25                  30

Gly Met Ser Trp Val Arg Gln Ala Pro Gly Lys Gly Leu Gln Trp Val
        35                  40                  45

Ala Thr Ile Ser Tyr Gly Gly Ser Tyr Thr Tyr Tyr Pro Asp Asn Ile
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Val Arg Gly Tyr Gly Tyr Asp Thr Met Asp Tyr Trp Gly Gln Gly Thr
            100                 105                 110

Leu Val Thr Val Ser Ser Ala Ser Thr Thr Ala Pro Ser Val Phe Pro
        115                 120                 125

Leu Ala Pro Ser Cys Gly Ser Thr Ser Gly Ser Thr Val Ala Leu Ala
    130                 135                 140

Cys Leu Val Ser Gly Tyr Phe Pro Glu Pro Val Thr Val Ser Trp Asn
145                 150                 155                 160

Ser Gly Ser Leu Thr Ser Gly Val His Thr Phe Pro Ser Val Leu Gln
                165                 170                 175

Ser Ser Gly Leu Tyr Ser Leu Ser Ser Met Val Thr Val Pro Ser Ser
            180                 185                 190

Arg Trp Pro Ser Glu Thr Phe Thr Cys Asn Val Ala His Pro Ala Ser
        195                 200                 205

Lys Thr Lys Val Asp Lys Pro Val Pro Lys Arg Glu Asn Gly Arg Val
    210                 215                 220

Pro Arg Pro Pro Asp Cys Pro Lys Cys Pro Ala Pro Glu Met Leu Gly
225                 230                 235                 240

Gly Pro Ser Val Phe Ile Phe Pro Pro Lys Pro Lys Asp Thr Leu Leu
                245                 250                 255

Ile Ala Arg Thr Pro Glu Val Thr Cys Val Val Val Asp Leu Asp Pro
            260                 265                 270

Glu Asp Pro Glu Val Gln Ile Ser Trp Phe Val Asp Gly Lys Gln Met
        275                 280                 285

Gln Thr Ala Lys Thr Gln Pro Arg Glu Glu Gln Phe Asn Gly Thr Tyr
    290                 295                 300

Arg Val Val Ser Val Leu Pro Ile Gly His Gln Asp Trp Leu Lys Gly
305                 310                 315                 320

Lys Gln Phe Thr Cys Lys Val Asn Asn Lys Ala Leu Pro Ser Pro Ile
                325                 330                 335

Glu Arg Thr Ile Ser Lys Ala Arg Gly Gln Ala His Gln Pro Ser Val
            340                 345                 350

Tyr Val Leu Pro Pro Ser Arg Glu Glu Leu Ser Lys Asn Thr Val Ser
        355                 360                 365
```

-continued

```
Leu Thr Cys Leu Ile Lys Asp Phe Phe Pro Pro Asp Ile Asp Val Glu
    370                 375                 380

Trp Gln Ser Asn Gly Gln Gln Glu Pro Glu Ser Lys Tyr Arg Thr Thr
385                 390                 395                 400

Pro Pro Gln Leu Asp Glu Asp Gly Ser Tyr Phe Leu Tyr Ser Lys Leu
                405                 410                 415

Ser Val Asp Lys Ser Arg Trp Gln Arg Gly Asp Thr Phe Ile Cys Ala
            420                 425                 430

Val Met His Glu Ala Leu His Asn His Tyr Thr Gln Glu Ser Leu Ser
        435                 440                 445

His Ser Pro Gly
    450


<210> SEQ ID NO 14
<211> LENGTH: 215
<212> TYPE: PRT
<213> ORGANISM: Canis familiaris

<400> SEQUENCE: 14

Leu Gly Gly Pro Ser Val Phe Ile Phe Pro Pro Lys Pro Lys Asp Thr
1               5                   10                  15

Leu Leu Ile Ala Arg Thr Pro Glu Val Thr Cys Val Val Val Asp Leu
            20                  25                  30

Asp Pro Glu Asp Pro Glu Val Gln Ile Ser Trp Phe Val Asp Gly Lys
        35                  40                  45

Gln Met Gln Thr Ala Lys Thr Gln Pro Arg Glu Glu Gln Phe Asn Gly
    50                  55                  60

Thr Tyr Arg Val Val Ser Val Leu Pro Ile Gly His Gln Asp Trp Leu
65                  70                  75                  80

Lys Gly Lys Gln Phe Thr Cys Lys Val Asn Asn Lys Ala Leu Pro Ser
                85                  90                  95

Pro Ile Glu Arg Thr Ile Ser Lys Ala Arg Gly Gln Ala His Gln Pro
            100                 105                 110

Ser Val Tyr Val Leu Pro Pro Ser Arg Glu Glu Leu Ser Lys Asn Thr
        115                 120                 125

Val Ser Leu Thr Cys Leu Ile Lys Asp Phe Phe Pro Pro Asp Ile Asp
    130                 135                 140

Val Glu Trp Gln Ser Asn Gly Gln Gln Glu Pro Glu Ser Lys Tyr Arg
145                 150                 155                 160

Thr Thr Pro Pro Gln Leu Asp Glu Asp Gly Ser Tyr Phe Leu Tyr Ser
                165                 170                 175

Lys Leu Ser Val Asp Lys Ser Arg Trp Gln Arg Gly Asp Thr Phe Ile
            180                 185                 190

Cys Ala Val Met His Glu Ala Leu His Asn His Tyr Thr Gln Lys Ser
        195                 200                 205

Leu Ser His Ser Pro Gly Lys
    210                 215


<210> SEQ ID NO 15
<211> LENGTH: 451
<212> TYPE: PRT
<213> ORGANISM: Artificial Sequence
<220> FEATURE:
<223> OTHER INFORMATION: modified canine and mouse

<400> SEQUENCE: 15
```

-continued

```
Glu Val Gln Leu Val Glu Ser Gly Pro Ser Leu Val Lys Pro Gly Gly
1               5                   10                  15

Ser Leu Arg Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Ile Thr Asp Tyr Asn Pro Ser Leu Lys
    50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Gly Asn Tyr Gly Tyr Ala Met Asp Tyr Trp Gly Gln Gly Thr
            100                 105                 110

Leu Val Thr Val Ser Ser Ala Ser Thr Thr Ala Pro Ser Val Phe Pro
        115                 120                 125

Leu Ala Pro Ser Cys Gly Ser Thr Ser Gly Ser Thr Val Ala Leu Ala
    130                 135                 140

Cys Leu Val Ser Gly Tyr Phe Pro Glu Pro Val Thr Val Ser Trp Asn
145                 150                 155                 160

Ser Gly Ser Leu Thr Ser Gly Val His Thr Phe Pro Ser Val Leu Gln
                165                 170                 175

Ser Ser Gly Leu Tyr Ser Leu Ser Ser Met Val Thr Val Pro Ser Ser
            180                 185                 190

Arg Trp Pro Ser Glu Thr Phe Thr Cys Asn Val Ala His Pro Ala Ser
        195                 200                 205

Lys Thr Lys Val Asp Lys Pro Val Pro Lys Arg Glu Asn Gly Arg Val
    210                 215                 220

Pro Arg Pro Pro Asp Cys Pro Lys Cys Pro Ala Pro Glu Met Leu Gly
225                 230                 235                 240

Gly Pro Ser Val Phe Ile Phe Pro Pro Lys Pro Lys Asp Thr Leu Leu
                245                 250                 255

Ile Ala Arg Thr Pro Glu Val Thr Cys Val Trp Asp Leu Asp Pro Glu
            260                 265                 270

Asp Pro Glu Val Gln Ile Ser Trp Phe Val Asp Gly Lys Gln Met Gln
        275                 280                 285

Thr Ala Lys Thr Gln Pro Arg Glu Glu Gln Phe Ala Gly Thr Tyr Arg
    290                 295                 300

Trp Ser Val Leu Pro Ile Gly His Gln Asp Trp Leu Lys Gly Lys Gln
305                 310                 315                 320

Phe Thr Cys Lys Val Asn Asn Lys Ala Leu Pro Ser Pro Ile Glu Arg
                325                 330                 335

Thr Ile Ser Lys Ala Arg Gly Gln Ala His Gln Pro Ser Val Tyr Val
            340                 345                 350

Leu Pro Pro Cys Arg Glu Glu Leu Ser Lys Asn Thr Val Ser Leu Trp
        355                 360                 365

Cys Leu Ile Lys Asp Phe Phe Pro Pro Asp Ile Asp Val Glu Trp Gln
    370                 375                 380

Ser Asn Gly Gln Gln Glu Pro Glu Ser Lys Tyr Arg Thr Thr Pro Pro
385                 390                 395                 400

Gln Leu Asp Glu Asp Gly Ser Tyr Phe Leu Tyr Ser Lys Leu Ser Val
                405                 410                 415

Asp Lys Ser Arg Trp Gln Arg Gly Asp Thr Phe Ile Cys Ala Val Met
```

```
            420                 425                 430

His Glu Ala Leu His Asn His Tyr Thr Gln Glu Ser Leu Ser His Ser
        435                 440                 445

Pro Gly Lys
    450


<210> SEQ ID NO 16
<211> LENGTH: 452
<212> TYPE: PRT
<213> ORGANISM: Artificial Sequence
<220> FEATURE:
<223> OTHER INFORMATION: modified canine and mouse

<400> SEQUENCE: 16

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asn Tyr
            20                  25                  30

Gly Met Ser Trp Val Arg Gln Ala Pro Gly Lys Gly Leu Gln Trp Val
        35                  40                  45

Ala Thr Ile Ser Tyr Gly Gly Ser Tyr Thr Tyr Tyr Pro Asp Asn Ile
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Val Arg Gly Tyr Gly Tyr Asp Thr Met Asp Tyr Trp Gly Gln Gly Thr
            100                 105                 110

Leu Val Thr Val Ser Ser Ala Ser Thr Thr Ala Pro Ser Val Phe Pro
        115                 120                 125

Leu Ala Pro Ser Cys Gly Ser Thr Ser Gly Ser Thr Val Ala Leu Ala
    130                 135                 140

Cys Leu Val Ser Gly Tyr Phe Pro Glu Pro Val Thr Val Ser Trp Asn
145                 150                 155                 160

Ser Gly Ser Leu Thr Ser Gly Val His Thr Phe Pro Ser Val Leu Gln
                165                 170                 175

Ser Ser Gly Leu Tyr Ser Leu Ser Ser Met Val Thr Val Pro Ser Ser
            180                 185                 190

Arg Trp Pro Ser Glu Thr Phe Thr Cys Asn Val Ala His Pro Ala Ser
        195                 200                 205

Lys Thr Lys Val Asp Lys Pro Val Pro Lys Arg Glu Asn Gly Arg Val
    210                 215                 220

Pro Arg Pro Pro Asp Cys Pro Lys Cys Pro Ala Pro Glu Met Leu Gly
225                 230                 235                 240

Gly Pro Ser Val Phe Ile Phe Pro Pro Lys Pro Lys Asp Thr Leu Leu
                245                 250                 255

Ile Ala Arg Thr Pro Glu Val Thr Cys Val Val Val Asp Leu Asp Pro
            260                 265                 270

Glu Asp Pro Glu Val Gln Ile Ser Trp Phe Val Asp Gly Lys Gln Met
        275                 280                 285

Gln Thr Ala Lys Thr Gln Pro Arg Glu Glu Gln Phe Asn Gly Thr Tyr
    290                 295                 300

Arg Val Val Ser Val Leu Pro Ile Gly His Gln Asp Trp Leu Lys Gly
305                 310                 315                 320

Lys Gln Phe Thr Cys Lys Val Asn Asn Lys Ala Leu Pro Ser Pro Ile
```

```
                325                 330                 335

Glu Arg Thr Ile Ser Lys Ala Arg Gly Gln Ala His Gln Pro Ser Val
            340                 345                 350

Tyr Val Leu Pro Pro Cys Arg Glu Glu Leu Ser Lys Asn Thr Val Ser
        355                 360                 365

Leu Trp Cys Leu Ile Lys Asp Phe Phe Pro Pro Asp Ile Asp Val Glu
    370                 375                 380

Trp Gln Ser Asn Gly Gln Gln Glu Pro Glu Ser Lys Tyr Arg Thr Thr
385                 390                 395                 400

Pro Pro Gln Leu Asp Glu Asp Gly Ser Tyr Phe Leu Tyr Ser Lys Leu
                405                 410                 415

Ser Val Asp Lys Ser Arg Trp Gln Arg Gly Asp Thr Phe Ile Cys Ala
            420                 425                 430

Val Met His Glu Ala Leu His Asn His Tyr Thr Gln Glu Ser Leu Ser
        435                 440                 445

His Ser Pro Gly
    450


<210> SEQ ID NO 17
<211> LENGTH: 455
<212> TYPE: PRT
<213> ORGANISM: Artificial Sequence
<220> FEATURE:
<223> OTHER INFORMATION: modified canine and human

<400> SEQUENCE: 17

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Ala Gly Leu Asp Trp Val
        35                  40                  45

Gly Trp Ile Asn Pro Tyr Thr Gly Ser Ala Phe Tyr Ala Gln Lys Phe
    50                  55                  60

Arg Gly Arg Val Thr Met Thr Arg Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Glu Pro Glu Lys Phe Asp Ser Asp Asp Ser Asp Val Trp Gly
            100                 105                 110

Gln Gly Thr Leu Val Thr Val Ser Ser Ala Ser Thr Thr Ala Pro Ser
        115                 120                 125

Val Phe Pro Leu Ala Pro Ser Cys Gly Ser Thr Ser Gly Ser Thr Val
    130                 135                 140

Ala Leu Ala Cys Leu Val Ser Gly Tyr Phe Pro Glu Pro Val Thr Val
145                 150                 155                 160

Ser Trp Asn Ser Gly Ser Leu Thr Ser Gly Val His Thr Phe Pro Ser
                165                 170                 175

Val Leu Gln Ser Ser Gly Leu Tyr Ser Leu Ser Ser Met Val Thr Val
            180                 185                 190

Pro Ser Ser Arg Trp Pro Ser Glu Thr Phe Thr Cys Asn Val Ala His
        195                 200                 205

Pro Ala Ser Lys Thr Lys Val Asp Lys Pro Val Pro Lys Arg Glu Asn
    210                 215                 220

Gly Arg Val Pro Arg Pro Pro Asp Cys Pro Lys Cys Pro Ala Pro Glu
```

```
225                 230                 235                 240

Met Leu Gly Gly Pro Ser Val Phe Ile Phe Pro Pro Lys Pro Lys Asp
                245                 250                 255

Thr Leu Leu Ile Ala Arg Thr Pro Glu Val Thr Cys Val Val Val Ala
            260                 265                 270

Leu Asp Pro Glu Asp Pro Glu Val Gln Ile Ser Trp Phe Val Asp Gly
        275                 280                 285

Lys Gln Met Gln Thr Ala Lys Thr Gln Pro Arg Glu Glu Gln Phe Ala
    290                 295                 300

Gly Thr Tyr Arg Val Val Ser Val Leu Pro Ile Gly His Gln Asp Trp
305                 310                 315                 320

Leu Lys Gly Lys Gln Phe Thr Cys Lys Val Asn Asn Lys Ala Leu Pro
                325                 330                 335

Ser Pro Ile Glu Arg Thr Ile Ser Lys Ala Arg Gly Gln Ala His Gln
            340                 345                 350

Pro Ser Val Tyr Val Leu Pro Pro Cys Arg Glu Glu Leu Ser Lys Asn
        355                 360                 365

Thr Val Ser Leu Trp Cys Leu Ile Lys Asp Phe Phe Pro Pro Asp Ile
    370                 375                 380

Asp Val Glu Trp Gln Ser Asn Gly Gln Gln Glu Pro Glu Ser Lys Tyr
385                 390                 395                 400

Arg Thr Thr Pro Pro Gln Leu Asp Glu Asp Gly Ser Tyr Phe Leu Tyr
                405                 410                 415

Ser Lys Leu Ser Val Asp Lys Ser Arg Trp Gln Arg Gly Asp Thr Phe
            420                 425                 430

Ile Cys Ala Val Met His Glu Ala Leu His Asn His Tyr Thr Gln Glu
        435                 440                 445

Ser Leu Ser His Ser Pro Gly
    450                 455


<210> SEQ ID NO 18
<211> LENGTH: 453
<212> TYPE: PRT
<213> ORGANISM: Artificial Sequence
<220> FEATURE:
<223> OTHER INFORMATION: modified canine and mouse

<400> SEQUENCE: 18

Glu Val Gln Leu Val Glu Ser Gly Gly Asp Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Asp Lys Arg Leu Gln Trp Val
        35                  40                  45

Ala Thr Ile Ser Arg Gly Gly Asp Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Gly Thr Leu Asn Asn Arg Gly Phe Ala Ser Trp Gly Gln Gly
            100                 105                 110

Thr Leu Val Thr Val Ser Ser Ala Ser Thr Thr Ala Pro Ser Val Phe
        115                 120                 125

Pro Leu Ala Pro Ser Cys Gly Ser Thr Ser Gly Ser Thr Val Ala Leu
```

```
    130                 135                 140

Ala Cys Leu Val Ser Gly Tyr Phe Pro Glu Pro Val Thr Val Ser Trp
145                 150                 155                 160

Asn Ser Gly Ser Leu Thr Ser Gly Val His Thr Phe Pro Ser Val Leu
                165                 170                 175

Gln Ser Ser Gly Leu Tyr Ser Leu Ser Ser Met Val Thr Val Pro Ser
            180                 185                 190

Ser Arg Trp Pro Ser Glu Thr Phe Thr Cys Asn Val Ala His Pro Ala
        195                 200                 205

Ser Lys Thr Lys Val Asp Lys Pro Val Pro Lys Arg Glu Asn Gly Arg
    210                 215                 220

Val Pro Arg Pro Pro Asp Cys Pro Lys Cys Pro Ala Pro Glu Met Leu
225                 230                 235                 240

Gly Gly Pro Ser Val Phe Ile Phe Pro Pro Lys Pro Lys Asp Thr Leu
                245                 250                 255

Leu Ile Ala Arg Thr Pro Glu Val Thr Cys Val Val Val Ala Leu Asp
            260                 265                 270

Pro Glu Asp Pro Glu Val Gln Ile Ser Trp Phe Val Asp Gly Lys Gln
        275                 280                 285

Met Gln Thr Ala Lys Thr Gln Pro Arg Glu Glu Gln Phe Ala Gly Thr
    290                 295                 300

Tyr Arg Val Val Ser Val Leu Pro Ile Gly His Gln Asp Trp Leu Lys
305                 310                 315                 320

Gly Lys Gln Phe Thr Cys Lys Val Asn Asn Lys Ala Leu Pro Ser Pro
                325                 330                 335

Ile Glu Arg Thr Ile Ser Lys Ala Arg Gly Gln Ala His Gln Pro Ser
            340                 345                 350

Val Cys Val Leu Pro Pro Ser Arg Glu Glu Leu Ser Lys Asn Thr Val
        355                 360                 365

Ser Leu Ser Cys Ala Ile Lys Asp Phe Phe Pro Pro Asp Ile Asp Val
    370                 375                 380

Glu Trp Gln Ser Asn Gly Gln Gln Glu Pro Glu Ser Lys Tyr Arg Thr
385                 390                 395                 400

Thr Pro Pro Gln Leu Asp Glu Asp Gly Ser Tyr Phe Leu Val Ser Lys
                405                 410                 415

Leu Ser Val Asp Lys Ser Arg Trp Gln Arg Gly Asp Thr Phe Ile Cys
            420                 425                 430

Ala Val Met His Glu Ala Leu His Asn His Tyr Thr Gln Glu Ser Leu
        435                 440                 445

Ser His Ser Pro Gly
    450


<210> SEQ ID NO 19
<211> LENGTH: 451
<212> TYPE: PRT
<213> ORGANISM: Artificial Sequence
<220> FEATURE:
<223> OTHER INFORMATION: modified canine and mouse

<400> SEQUENCE: 19

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Arg Tyr
            20                  25                  30

Trp Met His Trp Met Lys Gln Ala Pro Gly Ala Gly Leu Asp Trp Ile
```

```
        35                  40                  45

Gly Met Ile His Pro Asp Ser Gly Asn Ile Asn Tyr Asn Glu Arg Phe
    50                  55                  60

Lys Thr Lys Ala Thr Leu Thr Val Asp Lys Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gln Leu Arg Asn Ala Met Asp Tyr Trp Gly Gln Gly Thr Leu
            100                 105                 110

Val Thr Val Ser Ser Ala Ser Thr Thr Ala Pro Ser Val Phe Pro Leu
        115                 120                 125

Ala Pro Ser Cys Gly Ser Thr Ser Gly Ser Thr Val Ala Leu Ala Cys
    130                 135                 140

Leu Val Ser Gly Tyr Phe Pro Glu Pro Val Thr Val Ser Trp Asn Ser
145                 150                 155                 160

Gly Ser Leu Thr Ser Gly Val His Thr Phe Pro Ser Val Leu Gln Ser
                165                 170                 175

Ser Gly Leu Tyr Ser Leu Ser Ser Met Val Thr Val Pro Ser Ser Arg
            180                 185                 190

Trp Pro Ser Glu Thr Phe Thr Cys Asn Val Ala His Pro Ala Ser Lys
        195                 200                 205

Thr Lys Val Asp Lys Pro Val Pro Lys Arg Glu Asn Gly Arg Val Pro
    210                 215                 220

Arg Pro Pro Asp Cys Pro Lys Cys Pro Ala Pro Glu Met Leu Gly Gly
225                 230                 235                 240

Pro Ser Val Phe Ile Phe Pro Pro Lys Pro Lys Asp Thr Leu Leu Ile
                245                 250                 255

Ala Arg Thr Pro Glu Val Thr Cys Val Val Val Ala Leu Asp Pro Glu
            260                 265                 270

Asp Pro Glu Val Gln Ile Ser Trp Phe Val Asp Gly Lys Gln Met Gln
        275                 280                 285

Thr Ala Lys Thr Gln Pro Arg Glu Glu Gln Phe Ala Gly Thr Tyr Arg
    290                 295                 300

Val Val Ser Val Leu Pro Ile Gly His Gln Asp Trp Leu Lys Gly Lys
305                 310                 315                 320

Gln Phe Thr Cys Lys Val Asn Asn Lys Ala Leu Pro Ser Pro Ile Glu
                325                 330                 335

Arg Thr Ile Ser Lys Ala Arg Gly Gln Ala His Gln Pro Ser Val Cys
            340                 345                 350

Val Leu Pro Pro Ser Arg Glu Glu Leu Ser Lys Asn Thr Val Ser Leu
        355                 360                 365

Ser Cys Ala Ile Lys Asp Phe Phe Pro Pro Asp Ile Asp Val Glu Trp
    370                 375                 380

Gln Ser Asn Gly Gln Gln Glu Pro Glu Ser Lys Tyr Arg Thr Thr Pro
385                 390                 395                 400

Pro Gln Leu Asp Glu Asp Gly Ser Tyr Phe Leu Val Ser Lys Leu Ser
                405                 410                 415

Val Asp Lys Ser Arg Trp Gln Arg Gly Asp Thr Phe Ile Cys Ala Val
            420                 425                 430

Met His Glu Ala Leu His Asn His Tyr Thr Gln Glu Ser Leu Ser His
        435                 440                 445

Ser Pro Gly
    450
```

<210> SEQ ID NO 20
<211> LENGTH: 217
<212> TYPE: PRT
<213> ORGANISM: Artificial Sequence
<220> FEATURE:
<223> OTHER INFORMATION: canine and human

<400> SEQUENCE: 20

Gln Ala Val Leu Thr Gln Pro Pro Ser Val Ser Ala Val Leu Gly Gln
1               5                   10                  15

Arg Val Thr Ile Ser Cys Thr Gly Ser Ser Ser Asn Ile Gly Ala Gly
            20                  25                  30

Tyr Gly Val His Trp Tyr Gln Gln Leu Pro Gly Lys Ser Pro Lys Thr
        35                  40                  45

Ile Ile Tyr Gly Asp Ser Asn Arg Pro Ser Gly Val Pro Asp Arg Phe
    50                  55                  60

Ser Gly Ser Lys Ser Gly Ser Thr Ala Ser Leu Thr Ile Thr Gly Leu
65                  70                  75                  80

Gln Ala Glu Asp Glu Ala Asp Tyr Tyr Cys Gln Ser Tyr Asp Asn Ser
                85                  90                  95

Leu Ser Gly Tyr Val Phe Gly Ser Gly Thr Gln Leu Thr Val Leu Gly
            100                 105                 110

Gln Pro Lys Ala Ser Pro Ser Val Thr Leu Phe Pro Pro Ser Ser Glu
        115                 120                 125

Glu Leu Gly Ala Asn Lys Ala Thr Leu Val Cys Leu Ile Ser Asp Phe
    130                 135                 140

Tyr Pro Ser Gly Val Thr Val Ala Trp Lys Ala Asp Gly Ser Pro Val
145                 150                 155                 160

Thr Gln Gly Val Glu Thr Thr Lys Pro Ser Lys Gln Ser Asn Asn Lys
                165                 170                 175

Tyr Ala Ala Ser Ser Tyr Leu Ser Leu Thr Pro Asp Lys Trp Lys Ser
            180                 185                 190

His Ser Ser Phe Ser Cys Leu Val Thr His Glu Gly Ser Thr Val Glu
        195                 200                 205

Lys Lys Val Ala Pro Ala Glu Cys Ser
    210                 215

<210> SEQ ID NO 21
<211> LENGTH: 455
<212> TYPE: PRT
<213> ORGANISM: Artificial Sequence
<220> FEATURE:
<223> OTHER INFORMATION: modified canine and human

<400> SEQUENCE: 21

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Asn Tyr
            20                  25                  30

Tyr Met His Trp Val Arg Gln Ala Pro Gly Ala Gly Leu Asp Trp Met
        35                  40                  45

Gly Trp Ile Asn Pro Tyr Thr Gly Ser Ala Phe Tyr Ala Gln Lys Phe
    50                  55                  60

Arg Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys

-continued

```
                85                  90                  95

Ala Arg Glu Pro Glu Lys Phe Asp Ser Asp Asp Ser Asp Val Trp Gly
            100                 105                 110

Gln Gly Thr Leu Val Thr Val Ser Ser Ala Ser Thr Thr Ala Pro Ser
        115                 120                 125

Val Phe Pro Leu Ala Pro Ser Cys Gly Ser Thr Ser Gly Ser Thr Val
    130                 135                 140

Ala Leu Ala Cys Leu Val Ser Gly Tyr Phe Pro Glu Pro Val Thr Val
145                 150                 155                 160

Ser Trp Asn Ser Gly Ser Leu Thr Ser Gly Val His Thr Phe Pro Ser
                165                 170                 175

Val Leu Gln Ser Ser Gly Leu Tyr Ser Leu Ser Ser Met Val Thr Val
            180                 185                 190

Pro Ser Ser Arg Trp Pro Ser Glu Thr Phe Thr Cys Asn Val Ala His
        195                 200                 205

Pro Ala Ser Lys Thr Lys Val Asp Lys Pro Val Pro Lys Arg Glu Asn
    210                 215                 220

Gly Arg Val Pro Arg Pro Pro Asp Cys Pro Lys Cys Pro Ala Pro Glu
225                 230                 235                 240

Met Leu Gly Gly Pro Ser Val Phe Ile Phe Pro Pro Lys Pro Lys Asp
                245                 250                 255

Thr Leu Leu Ile Ala Arg Thr Pro Glu Val Thr Cys Val Val Val Ala
            260                 265                 270

Leu Asp Pro Glu Asp Pro Glu Val Gln Ile Ser Trp Phe Val Asp Gly
        275                 280                 285

Lys Gln Met Gln Thr Ala Lys Thr Gln Pro Arg Glu Glu Gln Phe Ala
    290                 295                 300

Gly Thr Tyr Arg Val Val Ser Val Leu Pro Ile Gly His Gln Asp Trp
305                 310                 315                 320

Leu Lys Gly Lys Gln Phe Thr Cys Lys Val Asn Asn Lys Ala Leu Pro
                325                 330                 335

Ser Pro Ile Glu Arg Thr Ile Ser Lys Ala Arg Gly Gln Ala His Gln
            340                 345                 350

Pro Ser Val Tyr Val Leu Pro Pro Ser Arg Glu Glu Leu Ser Lys Asn
        355                 360                 365

Thr Val Ser Leu Thr Cys Leu Ile Lys Asp Phe Phe Pro Pro Asp Ile
    370                 375                 380

Asp Val Glu Trp Gln Ser Asn Gly Gln Gln Glu Pro Glu Ser Lys Tyr
385                 390                 395                 400

Arg Thr Thr Pro Pro Gln Leu Asp Glu Asp Gly Ser Tyr Phe Leu Tyr
                405                 410                 415

Ser Lys Leu Ser Val Asp Lys Ser Arg Trp Gln Arg Gly Asp Thr Phe
            420                 425                 430

Ile Cys Ala Val Met His Glu Ala Leu His Asn His Tyr Thr Gln Glu
        435                 440                 445

Ser Leu Ser His Ser Pro Gly
    450                 455
```

<210> SEQ ID NO 22
<211> LENGTH: 217
<212> TYPE: PRT
<213> ORGANISM: Artificial Sequence
<220> FEATURE:
<223> OTHER INFORMATION: canine and human

<400> SEQUENCE: 22

Gln Ala Val Leu Thr Gln Pro Pro Ser Val Ser Ala Val Leu Gly Gln
1 5 10 15

Arg Val Thr Ile Ser Cys Thr Gly Ser Ser Ser Asn Ile Gly Ala Gly
20 25 30

Tyr Gly Val His Trp Tyr Gln Gln Leu Pro Gly Lys Ser Pro Lys Leu
35 40 45

Leu Ile Tyr Gly Asp Ser Asn Arg Pro Ser Gly Val Pro Asp Arg Phe
50 55 60

Ser Gly Ser Lys Ser Gly Ser Thr Ala Ser Leu Thr Ile Thr Gly Leu
65 70 75 80

Gln Ala Glu Asp Glu Ala Asp Tyr Tyr Cys Gln Ser Tyr Asp Asn Ser
85 90 95

Leu Ser Gly Tyr Val Phe Gly Gly Gly Thr His Leu Thr Val Leu Gly
100 105 110

Gln Pro Lys Ala Ser Pro Ser Val Thr Leu Phe Pro Pro Ser Ser Glu
115 120 125

Glu Leu Gly Ala Asn Lys Ala Thr Leu Val Cys Leu Ile Ser Asp Phe
130 135 140

Tyr Pro Ser Gly Val Thr Val Ala Trp Lys Ala Asp Gly Ser Pro Val
145 150 155 160

Thr Gln Gly Val Glu Thr Thr Lys Pro Ser Lys Gln Ser Asn Asn Lys
165 170 175

Tyr Ala Ala Ser Ser Tyr Leu Ser Leu Thr Pro Asp Lys Trp Lys Ser
180 185 190

His Ser Ser Phe Ser Cys Leu Val Thr His Glu Gly Ser Thr Val Glu
195 200 205

Lys Lys Val Ala Pro Ala Glu Cys Ser
210 215

<210> SEQ ID NO 23
<211> LENGTH: 455
<212> TYPE: PRT
<213> ORGANISM: Artificial Sequence
<220> FEATURE:
<223> OTHER INFORMATION: modified canine and human

<400> SEQUENCE: 23

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Tyr Met His Trp Val Arg Gln Ala Pro Gly Ala Gly Leu Asp Trp Val
35 40 45

Gly Trp Ile Asn Pro Tyr Thr Gly Ser Ala Phe Tyr Ala Gln Lys Phe
50 55 60

Arg Gly Arg Val Thr Leu Thr Arg Asp Thr Ser Thr Ser Thr Ala Tyr
65 70 75 80

Met Glu Leu Ser Ser Leu Arg Ala Gly Asp Ile Ala Val Tyr Tyr Cys
85 90 95

Ala Arg Glu Pro Glu Lys Phe Asp Ser Asp Asp Ser Asp Val Trp Gly
100 105 110

Gln Gly Thr Leu Val Thr Val Ser Ser Ala Ser Thr Thr Ala Pro Ser
115 120 125

Val Phe Pro Leu Ala Pro Ser Cys Gly Ser Thr Ser Gly Ser Thr Val

```
    130                 135                 140

Ala Leu Ala Cys Leu Val Ser Gly Tyr Phe Pro Glu Pro Val Thr Val
145                 150                 155                 160

Ser Trp Asn Ser Gly Ser Leu Thr Ser Gly Val His Thr Phe Pro Ser
                165                 170                 175

Val Leu Gln Ser Ser Gly Leu Tyr Ser Leu Ser Ser Met Val Thr Val
            180                 185                 190

Pro Ser Ser Arg Trp Pro Ser Glu Thr Phe Thr Cys Asn Val Ala His
        195                 200                 205

Pro Ala Ser Lys Thr Lys Val Asp Lys Pro Val Pro Lys Arg Glu Asn
    210                 215                 220

Gly Arg Val Pro Arg Pro Pro Asp Cys Pro Lys Cys Pro Ala Pro Glu
225                 230                 235                 240

Met Leu Gly Gly Pro Ser Val Phe Ile Phe Pro Pro Lys Pro Lys Asp
                245                 250                 255

Thr Leu Leu Ile Ala Arg Thr Pro Glu Val Thr Cys Val Val Val Ala
            260                 265                 270

Leu Asp Pro Glu Asp Pro Glu Val Gln Ile Ser Trp Phe Val Asp Gly
        275                 280                 285

Lys Gln Met Gln Thr Ala Lys Thr Gln Pro Arg Glu Glu Gln Phe Ala
    290                 295                 300

Gly Thr Tyr Arg Val Val Ser Val Leu Pro Ile Gly His Gln Asp Trp
305                 310                 315                 320

Leu Lys Gly Lys Gln Phe Thr Cys Lys Val Asn Asn Lys Ala Leu Pro
                325                 330                 335

Ser Pro Ile Glu Arg Thr Ile Ser Lys Ala Arg Gly Gln Ala His Gln
            340                 345                 350

Pro Ser Val Tyr Val Leu Pro Pro Ser Arg Glu Glu Leu Ser Lys Asn
        355                 360                 365

Thr Val Ser Leu Thr Cys Leu Ile Lys Asp Phe Phe Pro Pro Asp Ile
    370                 375                 380

Asp Val Glu Trp Gln Ser Asn Gly Gln Gln Glu Pro Glu Ser Lys Tyr
385                 390                 395                 400

Arg Thr Thr Pro Pro Gln Leu Asp Glu Asp Gly Ser Tyr Phe Leu Tyr
                405                 410                 415

Ser Lys Leu Ser Val Asp Lys Ser Arg Trp Gln Arg Gly Asp Thr Phe
            420                 425                 430

Ile Cys Ala Val Met His Glu Ala Leu His Asn His Tyr Thr Gln Glu
        435                 440                 445

Ser Leu Ser His Ser Pro Gly
    450                 455


<210> SEQ ID NO 24
<211> LENGTH: 217
<212> TYPE: PRT
<213> ORGANISM: Artificial Sequence
<220> FEATURE:
<223> OTHER INFORMATION: canine and human

<400> SEQUENCE: 24

Gln Ser Val Leu Thr Gln Pro Pro Ser Val Ser Gly Phe Leu Gly Gln
1               5                   10                  15

Arg Val Thr Ile Ser Cys Thr Gly Ser Ser Ser Asn Ile Gly Ala Gly
            20                  25                  30

Tyr Gly Val His Trp Tyr Gln Gln Leu Pro Gly Thr Gly Pro Arg Leu
```

```
        35                  40                  45

Leu Ile Tyr Gly Asp Ser Asn Arg Pro Ser Gly Val Pro Asp Arg Phe
    50                  55                  60

Ser Gly Ser Arg Ser Gly Ser Thr Ala Thr Leu Thr Ile Ser Gly Leu
65                  70                  75                  80

Gln Ala Glu Asp Glu Ala Asp Tyr Tyr Cys Gln Ser Tyr Asp Asn Ser
                85                  90                  95

Leu Ser Gly Tyr Val Phe Gly Gly Gly Thr His Leu Thr Val Leu Gly
            100                 105                 110

Gln Pro Lys Ala Ser Pro Ser Val Thr Leu Phe Pro Pro Ser Ser Glu
        115                 120                 125

Glu Leu Gly Ala Asn Lys Ala Thr Leu Val Cys Leu Ile Ser Asp Phe
    130                 135                 140

Tyr Pro Ser Gly Val Thr Val Ala Trp Lys Ala Asp Gly Ser Pro Val
145                 150                 155                 160

Thr Gln Gly Val Glu Thr Thr Lys Pro Ser Lys Gln Ser Asn Asn Lys
                165                 170                 175

Tyr Ala Ala Ser Ser Tyr Leu Ser Leu Thr Pro Asp Lys Trp Lys Ser
            180                 185                 190

His Ser Ser Phe Ser Cys Leu Val Thr His Glu Gly Ser Thr Val Glu
        195                 200                 205

Lys Lys Val Ala Pro Ala Glu Cys Ser
    210                 215


<210> SEQ ID NO 25
<211> LENGTH: 455
<212> TYPE: PRT
<213> ORGANISM: Artificial Sequence
<220> FEATURE:
<223> OTHER INFORMATION: modified canine and human

<400> SEQUENCE: 25

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Ala Gly Leu Asp Trp Val
        35                  40                  45

Gly Trp Ile Asn Pro Tyr Thr Gly Ser Ala Phe Tyr Ala Gln Lys Phe
    50                  55                  60

Arg Gly Arg Val Thr Met Thr Arg Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Glu Pro Glu Lys Phe Asp Ser Asp Asp Ser Asp Val Trp Gly
            100                 105                 110

Gln Gly Thr Leu Val Thr Val Ser Ser Ala Ser Thr Thr Ala Pro Ser
        115                 120                 125

Val Phe Pro Leu Ala Pro Ser Cys Gly Ser Thr Ser Gly Ser Thr Val
    130                 135                 140

Ala Leu Ala Cys Leu Val Ser Gly Tyr Phe Pro Glu Pro Val Thr Val
145                 150                 155                 160

Ser Trp Asn Ser Gly Ser Leu Thr Ser Gly Val His Thr Phe Pro Ser
                165                 170                 175

Val Leu Gln Ser Ser Gly Leu Tyr Ser Leu Ser Ser Met Val Thr Val
```

```
            180                 185                 190

Pro Ser Ser Arg Trp Pro Ser Glu Thr Phe Thr Cys Asn Val Ala His
        195                 200                 205

Pro Ala Ser Lys Thr Lys Val Asp Lys Pro Val Pro Lys Arg Glu Asn
    210                 215                 220

Gly Arg Val Pro Arg Pro Pro Asp Cys Pro Lys Cys Pro Ala Pro Glu
225                 230                 235                 240

Met Leu Gly Gly Pro Ser Val Phe Ile Phe Pro Pro Lys Pro Lys Asp
                245                 250                 255

Thr Leu Leu Ile Ala Arg Thr Pro Glu Val Thr Cys Val Val Val Ala
            260                 265                 270

Leu Asp Pro Glu Asp Pro Glu Val Gln Ile Ser Trp Phe Val Asp Gly
        275                 280                 285

Lys Gln Met Gln Thr Ala Lys Thr Gln Pro Arg Glu Glu Gln Phe Ala
    290                 295                 300

Gly Thr Tyr Arg Val Val Ser Val Leu Pro Ile Gly His Gln Asp Trp
305                 310                 315                 320

Leu Lys Gly Lys Gln Phe Thr Cys Lys Val Asn Asn Lys Ala Leu Pro
                325                 330                 335

Ser Pro Ile Glu Arg Thr Ile Ser Lys Ala Arg Gly Gln Ala His Gln
            340                 345                 350

Pro Ser Val Tyr Val Leu Pro Pro Ser Arg Glu Glu Leu Ser Lys Asn
        355                 360                 365

Thr Val Ser Leu Thr Cys Leu Ile Lys Asp Phe Phe Pro Pro Asp Ile
    370                 375                 380

Asp Val Glu Trp Gln Ser Asn Gly Gln Gln Glu Pro Glu Ser Lys Tyr
385                 390                 395                 400

Arg Thr Thr Pro Pro Gln Leu Asp Glu Asp Gly Ser Tyr Phe Leu Tyr
                405                 410                 415

Ser Lys Leu Ser Val Asp Lys Ser Arg Trp Gln Arg Gly Asp Thr Phe
            420                 425                 430

Ile Cys Ala Val Met His Glu Ala Leu His Asn His Tyr Thr Gln Glu
        435                 440                 445

Ser Leu Ser His Ser Pro Gly
    450                 455


<210> SEQ ID NO 26
<211> LENGTH: 17
<212> TYPE: PRT
<213> ORGANISM: Canis familiaris

<400> SEQUENCE: 26

Phe Asn Glu Cys Arg Cys Thr Asp Thr Pro Pro Cys Pro Val Pro Glu
1               5                   10                  15

Pro


<210> SEQ ID NO 27
<211> LENGTH: 22
<212> TYPE: PRT
<213> ORGANISM: Canis familiaris

<400> SEQUENCE: 27

Pro Lys Arg Glu Asn Gly Arg Val Pro Arg Pro Pro Asp Cys Pro Lys
1               5                   10                  15

Cys Pro Ala Pro Glu Met
            20
```

<210> SEQ ID NO 28
<211> LENGTH: 20
<212> TYPE: PRT
<213> ORGANISM: Canis familiaris

<400> SEQUENCE: 28

Ala Lys Glu Cys Glu Cys Lys Cys Asn Cys Asn Asn Cys Pro Cys Pro
1               5                   10                  15

Gly Cys Gly Leu
            20

<210> SEQ ID NO 29
<211> LENGTH: 17
<212> TYPE: PRT
<213> ORGANISM: Artificial Sequence
<220> FEATURE:
<223> OTHER INFORMATION: modified canine

<400> SEQUENCE: 29

Pro Lys Glu Ser Thr Cys Lys Cys Ile Pro Pro Cys Pro Val Pro Glu
1               5                   10                  15

Ser

<210> SEQ ID NO 30
<211> LENGTH: 5
<212> TYPE: PRT
<213> ORGANISM: Homo sapiens

<400> SEQUENCE: 30

Asn Tyr Tyr Met His
1               5

<210> SEQ ID NO 31
<211> LENGTH: 15
<212> TYPE: DNA
<213> ORGANISM: Homo sapiens

<400> SEQUENCE: 31
aactattata tgcat 15

<210> SEQ ID NO 32
<211> LENGTH: 14
<212> TYPE: PRT
<213> ORGANISM: Homo sapiens

<400> SEQUENCE: 32

Thr Gly Ser Ser Ser Asn Ile Gly Ala Gly Tyr Gly Val His
1               5                   10

<210> SEQ ID NO 33
<211> LENGTH: 42
<212> TYPE: DNA
<213> ORGANISM: Homo sapiens

<400> SEQUENCE: 33
accggcagca gcagcaacat tggcgcgggc tatggcgtgc at 42

<210> SEQ ID NO 34
<211> LENGTH: 17
<212> TYPE: PRT
<213> ORGANISM: Homo sapiens

<400> SEQUENCE: 34

Trp Ile Asn Pro Tyr Thr Gly Ser Ala Phe Tyr Ala Gln Lys Phe Arg
1 5 10 15

Gly

<210> SEQ ID NO 35
<211> LENGTH: 51
<212> TYPE: DNA
<213> ORGANISM: Homo sapiens

<400> SEQUENCE: 35
tggattaacc cgtataccgg cagcgcgttt tatgcgcaga aatttcgcgg c 51

<210> SEQ ID NO 36
<211> LENGTH: 7
<212> TYPE: PRT
<213> ORGANISM: Homo sapiens

<400> SEQUENCE: 36

Gly Asp Ser Asn Arg Pro Ser
1 5

<210> SEQ ID NO 37
<211> LENGTH: 21
<212> TYPE: DNA
<213> ORGANISM: Homo sapiens

<400> SEQUENCE: 37
ggcgatagca accgcccgag c 21

<210> SEQ ID NO 38
<211> LENGTH: 12
<212> TYPE: PRT
<213> ORGANISM: Homo sapiens

<400> SEQUENCE: 38

Glu Pro Glu Lys Phe Asp Ser Asp Asp Ser Asp Val
1 5 10

<210> SEQ ID NO 39
<211> LENGTH: 36
<212> TYPE: DNA
<213> ORGANISM: Homo sapiens

<400> SEQUENCE: 39
gaaccggaaa aatttgatag cgatgatagc gatgtg 36

<210> SEQ ID NO 40
<211> LENGTH: 11
<212> TYPE: PRT
<213> ORGANISM: Homo sapiens

<400> SEQUENCE: 40

Gln Ser Tyr Asp Asn Ser Leu Ser Gly Tyr Val
1 5 10

<210> SEQ ID NO 41
<211> LENGTH: 66
<212> TYPE: DNA
<213> ORGANISM: Homo sapiens

<400> SEQUENCE: 41
cagagctatg cagagctatg ataacagcct gagcggctat gtgataacag cctgagcggc 60

-continued tatgtg 66

<210> SEQ ID NO 42
<211> LENGTH: 452
<212> TYPE: PRT
<213> ORGANISM: Artificial Sequence
<220> FEATURE:
<223> OTHER INFORMATION: modified canine and rat

<400> SEQUENCE: 42

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asn Tyr
            20                  25                  30

Tyr Met Ala Trp Val Arg Gln Ala Pro Gly Lys Gly Leu Gln Trp Val
        35                  40                  45

Ala Ser Ile Ser Thr Gly Gly Gly Asn Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Lys His Gly Thr Leu Tyr Phe Asp Tyr Trp Gly Gln Gly Thr Leu
            100                 105                 110

Val Thr Val Ser Ser Ala Ser Thr Thr Ala Pro Ser Val Phe Pro Leu
        115                 120                 125

Ala Pro Ser Cys Gly Ser Thr Ser Gly Ser Thr Val Ala Leu Ala Cys
    130                 135                 140

Leu Val Ser Gly Tyr Phe Pro Glu Pro Val Thr Val Ser Trp Asn Ser
145                 150                 155                 160

Gly Ser Leu Thr Ser Gly Val His Thr Phe Pro Ser Val Leu Gln Ser
                165                 170                 175

Ser Gly Leu Tyr Ser Leu Ser Ser Met Val Thr Val Pro Ser Ser Arg
            180                 185                 190

Trp Pro Ser Glu Thr Phe Thr Cys Asn Val Ala His Pro Ala Ser Lys
        195                 200                 205

Thr Lys Val Asp Lys Pro Val Pro Lys Arg Glu Asn Gly Arg Val Pro
    210                 215                 220

Arg Pro Pro Asp Cys Pro Lys Cys Pro Ala Pro Glu Met Leu Gly Gly
225                 230                 235                 240

Pro Ser Val Phe Ile Phe Pro Pro Lys Pro Lys Asp Thr Leu Leu Ile
                245                 250                 255

Ala Arg Thr Pro Glu Val Thr Cys Val Val Val Ala Leu Asp Pro Glu
            260                 265                 270

Asp Pro Glu Val Gln Ile Ser Trp Phe Val Asp Gly Lys Gln Met Gln
        275                 280                 285

Thr Ala Lys Thr Gln Pro Arg Glu Glu Gln Phe Ala Gly Thr Tyr Arg
    290                 295                 300

Val Val Ser Val Leu Pro Ile Gly His Gln Asp Trp Leu Lys Gly Lys
305                 310                 315                 320

Gln Phe Thr Cys Lys Val Asn Asn Lys Ala Leu Pro Ser Pro Ile Glu
                325                 330                 335

Arg Thr Ile Ser Lys Ala Arg Gly Gln Ala His Gln Pro Ser Val Tyr
            340                 345                 350

Val Leu Pro Pro Ser Arg Glu Glu Leu Ser Lys Asn Thr Val Ser Leu
```

```
        355                 360                 365

Thr Cys Leu Ile Lys Asp Phe Phe Pro Pro Asp Ile Asp Val Glu Trp
    370                 375                 380

Gln Ser Asn Gly Gln Gln Glu Pro Glu Ser Lys Tyr Arg Thr Thr Pro
385                 390                 395                 400

Pro Gln Leu Asp Glu Asp Gly Ser Tyr Phe Leu Tyr Ser Lys Leu Ser
                405                 410                 415

Val Asp Lys Ser Arg Trp Gln Arg Gly Asp Thr Phe Ile Cys Ala Val
            420                 425                 430

Met His Glu Ala Leu His Asn His Tyr Thr Gln Glu Ser Leu Ser His
        435                 440                 445

Ser Pro Gly Lys
    450


<210> SEQ ID NO 43
<211> LENGTH: 218
<212> TYPE: PRT
<213> ORGANISM: Artificial Sequence
<220> FEATURE:
<223> OTHER INFORMATION: canine and rat

<400> SEQUENCE: 43

Gln Pro Val Leu Thr Gln Pro Pro Ser Leu Ser Ala Ser Leu Gly Thr
1               5                   10                  15

Thr Ala Arg Leu Thr Cys Glu Arg Ser Ser Gly Asp Ile Gly Asp Ser
            20                  25                  30

Tyr Val Ser Trp Tyr Gln Gln Lys Pro Gly Ser Pro Pro Arg Asp Leu
        35                  40                  45

Leu Tyr Val Asp Asp Gln Arg Pro Ser Gly Val Ser Lys Ser Phe Ser
    50                  55                  60

Gly Ser Lys Asp Thr Ser Ala Asn Ala Gly Leu Leu Leu Ile Ser Gly
65                  70                  75                  80

Leu Gln Pro Glu Asp Glu Ala Asp Tyr Tyr Cys Gln Ser Tyr Asp Ser
                85                  90                  95

Asn Ile Asp Gly Pro Val Phe Gly Gly Gly Thr His Leu Thr Val Leu
            100                 105                 110

Gly Gln Pro Lys Ala Ser Pro Ser Val Thr Leu Phe Pro Pro Ser Ser
        115                 120                 125

Glu Glu Leu Gly Ala Asn Lys Ala Thr Leu Val Cys Leu Ile Ser Asp
    130                 135                 140

Phe Tyr Pro Ser Gly Val Thr Val Ala Trp Lys Ala Asp Gly Ser Pro
145                 150                 155                 160

Val Thr Gln Gly Val Glu Thr Thr Lys Pro Ser Lys Gln Ser Asn Asn
                165                 170                 175

Lys Tyr Ala Ala Ser Ser Tyr Leu Ser Leu Thr Pro Asp Lys Trp Lys
            180                 185                 190

Ser His Ser Ser Phe Ser Cys Leu Val Thr His Glu Gly Ser Thr Val
        195                 200                 205

Glu Lys Lys Val Ala Pro Ala Glu Cys Ser
    210                 215


<210> SEQ ID NO 44
<211> LENGTH: 452
<212> TYPE: PRT
<213> ORGANISM: Artificial Sequence
<220> FEATURE:
<223> OTHER INFORMATION: modified canine and rat
```

<400> SEQUENCE: 44

Glu Val Gln Leu Val Glu Ser Gly Gly Asp Leu Val Lys Pro Gly Gly
1 5 10 15

Ser Leu Arg Leu Ser Cys Val Ala Ser Gly Phe Thr Phe Ser Asn Tyr
20 25 30

Tyr Met Ala Trp Val Arg Gln Ala Pro Gly Lys Gly Leu Gln Trp Val
35 40 45

Ala Ser Ile Ser Thr Gly Gly Gly Asn Thr Tyr Tyr Arg Asp Ser Val
50 55 60

Lys Gly Arg Phe Thr Ile Ser Arg Asp Asn Ala Lys Asn Thr Leu Tyr
65 70 75 80

Leu Gln Met Asn Ser Leu Arg Ala Glu Asp Thr Ala Met Tyr Tyr Cys
85 90 95

Ala Lys His Gly Thr Leu Tyr Phe Asp Tyr Trp Gly Gln Gly Thr Leu
100 105 110

Val Thr Val Ser Ser Ala Ser Thr Thr Ala Pro Ser Val Phe Pro Leu
115 120 125

Ala Pro Ser Cys Gly Ser Thr Ser Gly Ser Thr Val Ala Leu Ala Cys
130 135 140

Leu Val Ser Gly Tyr Phe Pro Glu Pro Val Thr Val Ser Trp Asn Ser
145 150 155 160

Gly Ser Leu Thr Ser Gly Val His Thr Phe Pro Ser Val Leu Gln Ser
165 170 175

Ser Gly Leu Tyr Ser Leu Ser Ser Met Val Thr Val Pro Ser Ser Arg
180 185 190

Trp Pro Ser Glu Thr Phe Thr Cys Asn Val Ala His Pro Ala Ser Lys
195 200 205

Thr Lys Val Asp Lys Pro Val Pro Lys Arg Glu Asn Gly Arg Val Pro
210 215 220

Arg Pro Pro Asp Cys Pro Lys Cys Pro Ala Pro Glu Met Leu Gly Gly
225 230 235 240

Pro Ser Val Phe Ile Phe Pro Pro Lys Pro Lys Asp Thr Leu Leu Ile
245 250 255

Ala Arg Thr Pro Glu Val Thr Cys Val Val Val Ala Leu Asp Pro Glu
260 265 270

Asp Pro Glu Val Gln Ile Ser Trp Phe Val Asp Gly Lys Gln Met Gln
275 280 285

Thr Ala Lys Thr Gln Pro Arg Glu Glu Gln Phe Ala Gly Thr Tyr Arg
290 295 300

Val Val Ser Val Leu Pro Ile Gly His Gln Asp Trp Leu Lys Gly Lys
305 310 315 320

Gln Phe Thr Cys Lys Val Asn Asn Lys Ala Leu Pro Ser Pro Ile Glu
325 330 335

Arg Thr Ile Ser Lys Ala Arg Gly Gln Ala His Gln Pro Ser Val Tyr
340 345 350

Val Leu Pro Pro Cys Arg Glu Glu Leu Ser Lys Asn Thr Val Ser Leu
355 360 365

Trp Cys Leu Ile Lys Asp Phe Phe Pro Pro Asp Ile Asp Val Glu Trp
370 375 380

Gln Ser Asn Gly Gln Gln Glu Pro Glu Ser Lys Tyr Arg Thr Thr Pro
385 390 395 400

Pro Gln Leu Asp Glu Asp Gly Ser Tyr Phe Leu Tyr Ser Lys Leu Ser

```
            405                 410                 415

Val Asp Lys Ser Arg Trp Gln Arg Gly Asp Thr Phe Ile Cys Ala Val
            420                 425                 430

Met His Glu Ala Leu His Asn His Tyr Thr Gln Glu Ser Leu Ser His
        435                 440                 445

Ser Pro Gly Lys
    450


<210> SEQ ID NO 45
<211> LENGTH: 20
<212> TYPE: PRT
<213> ORGANISM: Artificial Sequence
<220> FEATURE:
<223> OTHER INFORMATION: Modified canine

<400> SEQUENCE: 45

Phe Gly Gln Gly Thr Lys Val Glu Ile Lys Ser Ser Ala Ser Thr Thr
1               5                   10                  15

Ala Pro Ser Val
            20


<210> SEQ ID NO 46
<211> LENGTH: 19
<212> TYPE: PRT
<213> ORGANISM: Artificial Sequence
<220> FEATURE:
<223> OTHER INFORMATION: Modified canne

<400> SEQUENCE: 46

Trp Gly Gln Gly Thr Thr Leu Thr Val Ser Ser Ala Ser Asp Ala Gln
1               5                   10                  15

Pro Ala Val


<210> SEQ ID NO 47
<211> LENGTH: 20
<212> TYPE: PRT
<213> ORGANISM: Artificial Sequence
<220> FEATURE:
<223> OTHER INFORMATION: Modified canine

<400> SEQUENCE: 47

Phe Gly Gln Gly Thr Lys Val Glu Ser Lys Ser Ser Ala Ser Thr Thr
1               5                   10                  15

Ala Pro Ser Val
            20


<210> SEQ ID NO 48
<211> LENGTH: 19
<212> TYPE: PRT
<213> ORGANISM: Artificial Sequence
<220> FEATURE:
<223> OTHER INFORMATION: Modified canine

<400> SEQUENCE: 48

Trp Gly Gln Gly Thr Thr Leu Thr Val Ser Ser Arg Asn Asp Ala Gln
1               5                   10                  15

Pro Ala Val


<210> SEQ ID NO 49
<211> LENGTH: 20
<212> TYPE: PRT
<213> ORGANISM: Artificial Sequence
<220> FEATURE:
```

-continued

```
<223> OTHER INFORMATION: Modified canine

<400> SEQUENCE: 49

Phe Gly Gly Gly Thr His Leu Thr Val Leu Ser Ser Ala Ser Thr Thr
1               5                   10                  15

Ala Pro Ser Val
            20


<210> SEQ ID NO 50
<211> LENGTH: 18
<212> TYPE: PRT
<213> ORGANISM: Artificial Sequence
<220> FEATURE:
<223> OTHER INFORMATION: Modified canine

<400> SEQUENCE: 50

Trp Gly Gln Gly Thr Thr Leu Thr Val Ser Ser Gly Gln Pro Lys Ala
1               5                   10                  15

Ser Pro
```

BISPECIFIC CANINIZED ANTIBODIES FOR TREATING ATOPIC DERMATITIS

CROSS-REFERENCE TO RELATED APPLICATIONS

This application is a National Stage application of International Patent Application No. PCT/EP2020/086922 filed Dec. 18, 2020, which claims priority to U.S. Provisional Patent Application No. 63/092,296, filed Oct. 15, 2020, U.S. Provisional Patent Application No. 63/092,294, filed Oct. 15, 2020, U.S. Provisional Patent Application No. 63/015,209, filed Apr. 24, 2020, U.S. Provisional Patent Application No. 63/015,220, filed Apr. 24, 2020, U.S. Provisional Patent Application No. 62/951,793, filed Dec. 20, 2019 and U.S. Provisional Patent Application No. 62/951,778, filed Dec. 20, 2019, the contents of all of which are hereby incorporated by reference in their entireties.

SEQUENCE LISTING

This application incorporates by reference in its entirety the Computer Readable Form (CRF) of a Substitute Sequence Listing in ASCII text format submitted via Patent Center. The Substitute Sequence Listing text file submitted via Patent Center is entitled "14463-260-999_SUB_SL.txt", was created on Dec. 11, 2025, and is 92,266 bytes in size.

FIELD OF THE INVENTION

The present invention relates to compositions for treating atopic dermatitis in canines that comprise a caninized anti-proliferative antibody, a caninized anti-pruritic antibody, and a caninized anti-inflammatory antibody. The present invention further relates to compositions that comprise a bispecific antibody that comprises a caninized anti-pruritic antibody and a caninized anti-proliferative antibody or alternatively a bispecific antibody comprising a caninized anti-pruritic antibody and a caninized anti-inflammatory antibody.

BACKGROUND OF THE INVENTION

The immune system comprises a network of resident and recirculating specialized cells that function collaboratively to protect the host against infectious diseases and cancer. The ability of the immune system to perform this function depends to a large extent on the biological activities of a group of proteins secreted by leukocytes and collectively referred to as interleukins. Among the well-studied interleukins are three important molecules identified as interleukin-4 (IL-4), interleukin-31 (IL-31), and interleukin-22 (IL-22). Although IL-4, IL-31, and IL-22 are critical cytokines for the development of immune responses that are required for protection against extracellular pathogens (e.g., tissue or lumen dwelling parasites), these cytokines also have been implicated in the pathogenesis of allergic diseases in humans and animals, including atopic dermatitis.

Atopic dermatitis (AD) is a relapsing pruritic and chronic inflammatory skin disease, that is characterized by immune system dysregulation and epidermal barrier abnormalities in humans. The pathological and immunological attributes of atopic dermatitis have been the subject of extensive investigations [reviewed in Rahman et al. Inflammation & Allergy-drug target 10:486-496 (2011) and Harskamp et al., Seminar in Cutaneous Medicine and Surgery 32:132-139 (2013)]. Atopic dermatitis is also a common condition in companion animals, especially dogs, where its prevalence has been estimated to be approximately 10-15% of the canine population. The pathogenesis of atopic dermatitis in dogs and cats [reviewed in Nuttall et al., Veterinary Records 172 (8): 201-207 (2013)] shows significant similarities to that of atopic dermatitis in man including skin infiltration by a variety of immune cells and CD4+Th2 polarized cytokine milieu including the preponderance of IL-4, IL-13, and IL-31. In addition, IL-22 has been implicated in the exaggerated epithelial proliferation leading to epidermal hyperplasia that is characteristic of atopic dermatitis.

For example, antibodies against canine IL-31 have been shown to have a significant effect on pruritus associated with atopic dermatitis in dogs [U.S. Pat. No. 8,790,651 B2; U.S. Pat. No. 10,093,731 B2]. In addition, an antibody against human IL-31 receptor alpha (IL-31RA) has been tested and found to have a significant effect on pruritus associated with atopic dermatitis in humans [Ruzicka, et al., New England Journal of Medicine, 376 (9), 826-835 (2017)]. Accordingly, blocking IL-31 binding to its receptor IL-31RA, results in the relief of pruritus associated with atopic dermatitis.

Monoclonal antibodies raised against human interleukin-4 receptor alpha have been developed and some of these antibodies have been extensively tested for their therapeutic effects for treating atopic dermatitis in humans [see, e.g., US2015/0017176 A1]. More recently, caninized antibodies to canine interleukin-4 receptor alpha (canine IL-4R alpha, canine IL-4$R_\alpha$, CIL-4R alpha, or cIL-4$R_\alpha$) that block the binding of canine IL-4 to canine IL-4$R_\alpha$ also have been disclosed [US2018/0346580A1, hereby incorporated by reference in its entirety]. Because the Type II IL-4 receptor consists of the IL-4 receptor α chain and the IL-13 receptor α1 chain, antibodies to canine IL-4$R_\alpha$ have been obtained that can block both canine IL-4 and canine IL-13 from binding the Type II canine IL-4 receptor, thereby serving to help block the inflammation associated with atopic dermatitis [US2018/0346580A1].

Interleukin-22 (IL-22), also known as IL-10-related T cell-derived inducible factor (IL-TIF), belongs to the IL-10 cytokine family. IL-22 is produced by normal T cells upon anti-CD3 stimulation in humans. Mouse IL-22 expression is also induced in various organs upon lipopolysaccharide injection, suggesting that IL-22 may be involved in inflammatory responses. IL-22 binds specifically to, and signals through, a receptor complex consisting of a heterodimeric complex of IL-10R2 (also known as IL-10R beta) and the interleukin-22 receptor (IL-22R) [see, Lee et al., Pharmacology Research & Perspectives, *Pages* 1-13 (2018: e00434)]. The interleukin-22 receptor is also known as interleukin-22R, alpha 1; IL-22RA1; IL-22R1; zcytor11; and CRF2-9 [Xu et al., *Proc. Nat. Acad. Sci.* 98 (17) 9511-9516 (2001); Gelebart and Lai, *Atlas of Genetics and Cytogenetics* 14 (12): 1106-1110 (2010)]. IL-22 induces epithelial cell proliferation during wound healing, and its deficiency might enhance tumor development [Huber et al., *Nature* 491:259-263 (2012]. IL-22 has been shown to activate STAT-1 and STAT-3 in several hepatoma cell lines and upregulate the production of acute phase proteins. Antibodies to interleukin-22 and IL-22R act as anti-proliferative agents by blocking the interaction of IL-22 with IL-22R and thereby the related signaling pathway that leads to the epithelial proliferation.

Pharmaceuticals that have either proven to be aid in the treatment of atopic dermatitis and/or have shown promise to do so include: Janus kinase (JAK) inhibitors [see e.g., U.S. Pat. Nos. 8,133,899; 8,987,283; WO 2018/108969], spleen tyrosine kinase (SYK) inhibitors [see e.g., U.S. Pat. No.

8,759,366], and antagonists to a chemoattractant receptor-homologous molecule expressed on TH2 cells [see e.g., U.S. Pat. Nos. 7,696,222, 8,546,422, 8,637,541, and 8,546,422].

However, despite recent success in treating atopic dermatitis, none of the current therapies employed result in a rapid onset of anti-pruritic action concomitant with a significant effect on the skin inflammation with an improvement in skin barrier function. Therefore, there is a need to design better therapies that can address these three symptoms of atopic dermatitis at once.

The citation of any reference herein should not be construed as an admission that such reference is available as "prior art" to the instant application.

SUMMARY OF THE INVENTION

The present invention relates to bispecific antibodies and compositions comprising bispecific antibodies for treating atopic dermatitis in canines. In certain embodiments, the composition for treating atopic dermatitis in canines comprises an anti-pruritic antibody, an anti-proliferative antibody, and an anti-inflammatory antibody. In particular embodiments of this type, one, two, or all of the antibodies is a chimeric rodent (i.e., mouse or rat)-canine antibody. In yet other particular embodiments of this type, one, two, or all of the antibodies is a caninized antibody. In still other particular embodiments of this type, one, two, or all of the antibodies is a canine antibody. In specific embodiments, the anti-pruritic antibody is part of a bispecific antibody that further comprises an anti-proliferative antibody or an anti-inflammatory antibody. In still more specific embodiments, the bispecific antibody comprises a monomer of a caninized IL-31 antibody and a monomer of a caninized IL-22 antibody. In alternative embodiments, the bispecific antibody comprises a monomer of a caninized IL-31RA antibody and a monomer of a caninized IL-4R alpha antibody.

Accordingly, in certain embodiments, the composition for treating atopic dermatitis in canines comprises a caninized anti-pruritic antibody, a caninized anti-proliferative antibody, and a caninized anti-inflammatory antibody. In more specific embodiments of this type, the caninized anti-pruritic antibody is part of a bispecific antibody that further comprises the caninized anti-proliferative antibody or the caninized anti-inflammatory antibody.

In certain embodiments, the composition comprises a caninized anti-inflammatory antibody and a bispecific antibody that comprises a monomer of the caninized anti-pruritic antibody comprising a heavy chain and a light chain, and a monomer of the caninized anti-proliferative antibody comprising a heavy chain and a light chain. In particular embodiments of this type, the caninized anti-pruritic antibody is a caninized interleukin-31 (IL-31) antibody. In more particular embodiments of this type, the caninized IL-31 antibody comprises a light chain comprising the amino acid sequence of SEQ ID NO: 12 and a heavy chain comprising the amino acid sequence of SEQ ID NO: 16. In alternative embodiments of this type, the caninized IL-31 antibody comprises a light chain comprising the amino acid sequence of SEQ ID NO: 11 and a heavy chain comprising the amino acid sequence of SEQ ID NO: 15. In specific embodiments, the light chain of the caninized IL-31 antibody has been modified to comprise a heavy chain constant region 1 (CH1) from the heavy chain of the caninized IL-31 antibody in place of a constant light domain (CL) and the heavy chain of the caninized IL-31 antibody has been modified to comprise the constant light domain (CL) from the light chain of the caninized IL-31 antibody in place of the CH1. In certain embodiments, the caninized anti-proliferative antibody of the bispecific antibody is a monomer of a caninized interleukin-22 (IL-22) antibody. In more particular embodiments of this type, the caninized IL-22 antibody comprises a light chain comprising the amino acid sequence of SEQ ID NO: 24 and a heavy chain comprising the amino acid sequence of SEQ ID NO: 17. In still more particular embodiments, the caninized anti-inflammatory antibody is a caninized interleukin-4 receptor alpha (IL-4R alpha) antibody. In certain embodiments, the caninized IL-4R alpha antibody comprises a light chain comprising the amino acid sequence of SEQ ID NO: 4 and a heavy chain comprising the amino acid sequence of SEQ ID NO: 5. In alternative embodiments, the caninized IL-4R alpha antibody comprises a light chain comprising the amino acid sequence of SEQ ID NO: 6 and a heavy chain comprising the amino acid sequence of SEQ ID NO: 7.

In alternative embodiments, the composition comprises a caninized anti-proliferative antibody and a bispecific antibody that comprises a monomer of the caninized anti-pruritic antibody comprising a heavy chain and a light chain and a monomer of the caninized anti-inflammatory antibody comprising a heavy chain and a light chain. In particular embodiments of this type, the caninized anti-pruritic antibody is a caninized interleukin-31 receptor alpha (IL-31RA) antibody. In related embodiments, the caninized anti-inflammatory antibody is a caninized interleukin-4 receptor alpha (IL-4R alpha) antibody. In more particular embodiments, the caninized anti-pruritic antibody is a caninized IL-31RA antibody and the caninized anti-inflammatory antibody is a caninized IL-4R alpha antibody. In even more particular embodiments, the caninized IL-4R alpha antibody comprises a light chain comprising the amino acid sequence of SEQ ID NO: 4 and a heavy chain comprising the amino acid sequence of SEQ ID NO: 18. In alternative embodiments of this type, the caninized IL-4R alpha antibody comprises a light chain comprising the amino acid sequence of SEQ ID NO: 6 and a heavy chain comprising the amino acid sequence of SEQ ID NO: 19. In specific embodiments, the light chain of the caninized IL-4R alpha antibody has been modified to comprise a heavy chain constant region 1 (CH1) from the heavy chain of the caninized IL-4R alpha antibody in place of a constant light domain (CL) and the heavy chain of the caninized IL-4R alpha antibody has been modified to comprise the constant light domain (CL) from the light chain of the caninized IL-4R alpha antibody in place of the CH1. In more specific embodiments, the caninized IL-31RA antibody comprises a light chain comprising the amino acid sequence of SEQ ID NO: 43 and a heavy chain comprising the amino acid sequence of SEQ ID NO: 44. In still more particular embodiments, the caninized anti-proliferative antibody is a caninized interleukin-22 (IL-22) antibody. In certain embodiments, the caninized IL-22 antibody comprises a light chain comprising the amino acid sequence of SEQ ID NO: 20 and a heavy chain comprising the amino acid sequence of SEQ ID NO: 22. In alternative embodiments, the caninized IL-22 antibody comprises a light chain comprising the amino acid sequence of SEQ ID NO: 22 and a heavy chain comprising the amino acid sequence of SEQ ID NO: 23. In other alternative embodiments, the caninized IL-22 antibody comprises a light chain comprising the amino acid sequence of SEQ ID NO: 24 and a heavy chain comprising the amino acid sequence of SEQ ID NO: 25.

The present invention further provides the bispecific antibodies of the present invention. In certain embodiments, the anti-pruritic antibody is part of a bispecific antibody that further comprises an anti-proliferative antibody or an anti-inflammatory antibody. In particular embodiments, the bispecific antibody comprises a monomer of the caninized anti-pruritic antibody comprising a heavy chain and a light chain, and a monomer of the caninized anti-proliferative antibody comprising a heavy chain and a light chain. In more particular embodiments of this type, the caninized anti-pruritic antibody is a caninized interleukin-31 (IL-31) antibody. In even more particular embodiments of this type, the caninized IL-31 antibody comprises a light chain comprising the amino acid sequence of SEQ ID NO: 12 and a heavy chain comprising the amino acid sequence of SEQ ID NO: 16. In alternative embodiments of this type, the caninized IL-31 antibody comprises a light chain comprising the amino acid sequence of SEQ ID NO: 11 and a heavy chain comprising the amino acid sequence of SEQ ID NO: 15. In specific embodiments, the light chain of the caninized IL-31 antibody has been modified to comprise a heavy chain constant region 1 (CH1) from the heavy chain of the caninized IL-31 antibody in place of a constant light domain (CL) and the heavy chain of the caninized IL-31 antibody has been modified to comprise the constant light domain (CL) from the light chain of the caninized IL-31 antibody in place of the CH1. In certain embodiments, the caninized anti-proliferative antibody of the bispecific antibody is a monomer of a caninized interleukin-22 (IL-22) antibody. In more particular embodiments of this type, the caninized IL-22 antibody comprises a light chain comprising the amino acid sequence of SEQ ID NO: 24 and a heavy chain comprising the amino acid sequence of SEQ ID NO: 17.

In alternative embodiments, the present invention provides bispecific antibodies comprising a monomer of the caninized anti-pruritic antibody comprising a heavy chain and a light chain, and a monomer of the caninized anti-inflammatory antibody comprising a heavy chain and a light chain. In specific embodiments, the caninized anti-pruritic antibody is a caninized interleukin-31 receptor alpha (IL-31RA) antibody. In related embodiments, the caninized anti-inflammatory antibody is a caninized interleukin-4 receptor alpha (IL-4R alpha) antibody. In more particular embodiments of the bispecific antibodies, the caninized anti-pruritic antibody is a caninized IL-31RA antibody and the caninized anti-inflammatory antibody is a caninized IL-4R alpha antibody. In even more particular embodiments, the caninized IL-4R alpha antibody comprises a light chain comprising the amino acid sequence of SEQ ID NO: 4 and a heavy chain comprising the amino acid sequence of SEQ ID NO: 18. In alternative embodiments of this type, the caninized IL-4R alpha antibody comprises a light chain comprising the amino acid sequence of SEQ ID NO: 6 and a heavy chain comprising the amino acid sequence of SEQ ID NO: 19. In specific embodiments, the light chain of the caninized IL-4R alpha antibody has been modified to comprise a heavy chain constant region 1 (CH1) from the heavy chain of the caninized IL-4R alpha antibody in place of a constant light domain (CL) and the heavy chain of the caninized IL-4R alpha antibody has been modified to comprise the constant light domain (CL) from the light chain of the caninized IL-4R alpha antibody in place of the CH1. In more specific embodiments, the caninized IL-31RA antibody comprises a light chain comprising the amino acid sequence of SEQ ID NO: 43 and a heavy chain comprising the amino acid sequence of SEQ ID NO: 44.

In still other embodiments, compositions comprising the bispecific antibodies and/or the antibodies of the present invention can further comprise one or more additional therapeutic components. In one such embodiment, the therapeutic component is a Janus kinase (JAK) inhibitor. In a particular embodiment of this type the JAK inhibitor is oclacitinib and pharmaceutically acceptable salts thereof. In an alternative embodiment the JAK inhibitor, is: 1-[(3R,4S)-4-cyanotetrahydropyran-3-yl]-3-[(2-fluoro-6-methoxy-4-pyridyl)amino]pyrazole-4-carboxamide, and pharmaceutically acceptable salts thereof. In another embodiment, the therapeutic component is a spleen tyrosine kinase (SYK) inhibitor. In a particular embodiment of this type the SYK inhibitor is (1S,4R)-4-hydroxy-2,2-dimethyl-4-{5-[3-methyl-5-(4-methyl-pyrimidin-2-ylamino)-phenyl]-1,3-thiazol-2-yl}-cyclohexanecarboxylic acid or pharmaceutically acceptable salts thereof. In yet another embodiment, the therapeutic component is an antagonist to a chemoattractant receptor-homologous molecule expressed on TH2 cells.

The present invention further provides methods of treating atopic dermatitis comprising administering one of the aforesaid compositions and/or bispecific antibodies to a canine that has atopic dermatitis.

These and other aspects of the present invention will be better appreciated by reference to the following Brief Description of the Drawings and the Detailed Description.

BRIEF DESCRIPTION OF THE DRAWINGS

FIG. 1 is a graph showing the binding of canine IL-22 to anti-IL-22 antibody.

FIG. 2 is a graph showing the inhibition of IL-4-mediated STAT-6 phosphorylation by IL-4R alpha (IL-4$R_\alpha$) antibodies. Three different caninized monoclonal anti-canine IL-4$R_\alpha$ antibodies designated c4H3, c146E2-H3L3, and c152H11-H3L3 were evaluated for their ability to inhibit αSTAT-6 phosphorylation. The data show that all three antibodies result in a dose-dependent inhibition of STAT-6 phosphorylation in the presence of IL-4. The IL-4 control in the absence of IL-4R alpha (IL-4$R_\alpha$) antibodies is shown in the upper left hand portion of the graph.

FIG. 3 is a graph showing the inhibition of IL-13-mediated STAT-6 phosphorylation by IL-4R alpha antibodies. Three different caninized monoclonal anti-canine IL-4$R_\alpha$ antibodies designated c4H3, c146E2-H3L3, and c152H11-H3L3 were evaluated for their ability to inhibit STAT-6 phosphorylation. The data shows that all three antibodies result in a dose dependent inhibition of STAT-6 phosphorylation in the presence of IL-13. The IL-13 control in the absence of IL-4R alpha (IL-4$R_\alpha$) antibodies is shown in the upper left-hand portion of the graph.

FIG. 4 is a graph showing the binding of IL-31 to the extracellular domain of IL-31R (IL-31RA). The extracellular domain (ECD) of canine IL-31RA was tested for its ability to bind to canine IL-31. The results show that IL-31RA ECD binds in a dose-dependent manner to biotinylated canine IL-31 with an EC50 of 0.3679 μg/ml.

DETAILED DESCRIPTION OF THE INVENTION

In response to need for better therapies for atopic dermatitis, the present invention provides formulations and methodology that can achieve the simultaneous modulation of IL-4, IL-31, and IL-22, and produce a rapid onset of anti-pruritic action concomitant with a significant effect on the skin inflammation and an improvement in skin barrier function.

Abbreviations

Throughout the detailed description and examples of the invention the following abbreviations will be used:

ADCC Antibody-dependent cellular cytotoxicity

CDC Complement-dependent cytotoxicity
CDR Complementarity determining region in the immunoglobulin variable regions, defined using the Kabat numbering system
CHO Chinese hamster ovary
CL Constant Light Domain
EC50 concentration resulting in 50% efficacy or binding
ELISA Enzyme-linked immunosorbant assay
FR Antibody framework region: the immunoglobulin variable regions excluding the CDR regions.
HRP Horseradish peroxidase
IFN interferon
IC50 concentration resulting in 50% inhibition
IgG Immunoglobulin G
Kabat An immunoglobulin alignment and numbering system pioneered by Elvin A. Kabat [Sequences of Proteins of Immunological Interest, 5th Ed. Public Health Service, National Institutes of Health, Bethesda, Md. (1991)]
mAb Monoclonal antibody (also Mab or MAb)
MES 2-(N-morpholino) ethanesulfonic acid
MOA Mechanism of action
NHS Normal human serum
PCR Polymerase chain reaction
PK Pharmacokinetics
SEB *Staphylococcus* Enterotoxin B
TT Tetanus toxoid
VH Immunoglobulin heavy chain variable region
VL Immunoglobulin light chain variable region
VK Immunoglobulin kappa light chain variable region Definitions So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Activation" as it applies to cells or to receptors refers to the activation or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Activity" may refer to modulation of components of the innate or the adaptive immune systems.

"Administration" and "treatment", as it applies to an animal, e.g., a canine subject, cell, tissue, organ, or biological fluid, refers to contact of an exogenous pharmaceutical, therapeutic, diagnostic agent, or composition to the animal e.g., a canine subject, cell, tissue, organ, or biological fluid. Treatment of a cell encompasses contact of a reagent to the cell, as well as contact of a reagent to a fluid, where the fluid is in contact with the cell.

"Administration" and "treatment" also mean in vitro and ex vivo treatments, e.g., of a cell, by a reagent, diagnostic, binding compound, or by another cell. The term "subject" includes any organism, preferably an animal, more preferably a mammal (e.g., canine, feline, or human) and most preferably a canine.

"Treat" or "treating" means to administer a therapeutic agent, such as a composition containing any of the antibodies and/or the bispecific antibodies of the present invention, internally or externally to e.g., a canine subject or patient having one or more symptoms, or being suspected of having a condition, for which the agent has therapeutic activity.

Typically, the agent is administered in an amount effective to alleviate and/or ameliorate one or more disease/condition symptoms in the treated subject or population, whether by inducing the regression of or inhibiting the progression of such symptom(s) by any clinically measurable degree. The amount of a therapeutic agent that is effective to alleviate any particular disease/condition symptom (also referred to as the "therapeutically effective amount") may vary according to factors such as the disease state, age, and weight of the patient (e.g., canine), and the ability of the pharmaceutical composition to elicit a desired response in the subject. Whether a disease/condition symptom has been alleviated or ameliorated can be assessed by any clinical measurement typically used by veterinarians or other skilled healthcare providers to assess the severity or progression status of that symptom. While an embodiment of the present invention (e.g., a treatment method or article of manufacture) may not be effective in alleviating the target disease/condition symptom(s) in every subject, it should alleviate the target disease/condition symptom(s) in a statistically significant number of subjects as determined by any statistical test known in the art such as the Student's t-test, the chi2-test, the U-test according to Mann and Whitney, the Kruskal-Wallis test (H-test), Jonckheere-Terpstra-test and the Wilcoxon-test.

"Treatment," as it applies to a human, veterinary (e.g., canine), or research subject, refers to therapeutic treatment, as well as research and diagnostic applications. "Treatment" as it applies to a human, veterinary (e.g., canine), or research subject, or cell, tissue, or organ, encompasses contact of the antibodies and/or the bispecific antibodies of the present invention to e.g., a canine or other animal subject, a cell, tissue, physiological compartment, or physiological fluid.

As used herein, the term "canine" includes all domestic dogs, *Canis lupus familiaris* or *Canis familiaris*, unless otherwise indicated.

As used herein, the term "feline" refers to any member of the Felidae family. Members of this family include wild, zoo, and domestic members, including domestic cats, purebred and/or mongrel companion cats, show cats, laboratory cats, cloned cats, and wild or feral cats.

As used herein the term "canine frame" refers to the amino acid sequence of the heavy chain and light chain of a canine antibody other than the hypervariable region residues defined herein as CDR residues. With regard to a caninized antibody, in the majority of embodiments the amino acid sequences of the native canine CDRs are replaced with the corresponding foreign CDRs (e.g., those from a mouse or rat antibody) in both chains. Optionally the heavy and/or light chains of the canine antibody may contain some foreign non-CDR residues, e.g., so as to preserve the conformation of the foreign CDRs within the canine antibody, and/or to modify the Fc function, as exemplified below and/or disclosed in U.S. Pat. No. 10,106,607 B2, hereby incorporated by reference herein in its entirety.

Canine antibodies (also referred to as immunoglobulin G or IgG) are large tetrameric proteins of about 150 Kd. Each IgG protein is composed of two identical light chains of about 25 Kd each, and two identical heavy chains of about 50 Kd each. There are four known IgG heavy chain subclasses of canine IgG and they are referred to as IgGA, IgGB, IgGC, and IgGD. There are two types of light chains; kappa or lambda chains. Each of the kappa or lambda light chains is composed of one variable domain (VL) and one constant domain (CL). Each of the two heavy chains consists of one variable domain (VH) and three constant domains referred to as heavy chain constant region 1 (CH1 or CH-1), heavy chain constant region 2 (CH2 or CH-2), and heavy chain constant region 3 (CH3 or CH-3). The CH1 domain is connected to the CH2 domain via an amino acid sequence referred to as the "hinge" or alternatively as the "hinge region". In the present invention, the amino acid sequence for each of the four canine IgG Fc fragments is based on the identified boundary of the CH1 and the CH2 domains as determined by Tang et al. [*Vet. Immunol. Immunopathol.* 80:259-270 (2001)]. In humans, IgG exists in one of four subclasses referred to as IgG1, IgG2, IgG3, and IgG4. The subclass of IgG is determined largely by the sequence of the hinge region, which differs among the four subclasses of IgG. The two heavy chains are linked to each other by disulfide bonds and each heavy chain also is linked to one of the light chains through a disulfide bond.

Digestion of IgG antibodies with the enzyme papain breaks an antibody molecule in the hinge region and results in the formation of three fragments. Two of these fragments are identical and each consists of the light chain held together with the VH and CH1 domains of the heavy chain. These fragments are called the "Fab" fragments and they contain the antigen binding sites of the antibody. A Fab fragment is a VL-CL chain appended to a VH-CH1 chain by a disulfide bridge. The third fragment that results from digestion with papain is called the "Fc" and it contains the remainder of the two heavy chains held together by disulfide bonds. The Fc thus contains a dimer consisting of the CH2 and CH3 domain of each of the two heavy chains. While the Fab enables the antibody to bind to its cognate epitope, the Fc enables the antibody to mediate immune effector functions such as antibody dependent cellular cytotoxicity (ADCC), antibody-dependent phagocytosis (ADCP) and complement dependent cytotoxicity (CDC). A "Fab fragment" is comprised of one light chain (VL domain and CL domain) and the CH1 and variable regions (VH) of one heavy chain. The heavy chain of a Fab molecule cannot form a disulfide bond with another heavy chain molecule.

The "Fragment crystallizable region" abbreviated as "Fc" corresponds to the CH3-CH2 portion of an antibody that interacts with cell surface receptors called Fc receptors. The canine fragment crystallizable region (cFc) of each of the four canine IgGs were first described by Tang et al. [*Vet. Immunol. Immunopathol.* 80:259-270 (2001); see also, Bergeron et al., *Vet. Immunol. Immunopathol.* 157:31-41 (2014) and U.S. Pat. No. 10,106,607 B2].

As used herein the canine Fc (cFc) "IgG-Bm" is canine IgG-B Fc comprising two (2) amino acid residue substitutions, D31A and N63A in the amino acid sequence of SEQ ID NO: 14 of IgG-B (see below). Both the aspartic acid residue (D) at position 31 of SEQ ID NO: 14 and the asparagine residue (N) at position 63 of SEQ ID NO: 14, are substituted by an alanine residue (A) in IgG-Bm. These two amino acid residue substitutions serve to significantly diminish the antibody-dependent cytotoxicity (ADCC) and complement-dependent cytotoxicity (CDC) of the naturally occurring canine IgG-B [see, U.S. Pat. No. 10,106,607 B2, the contents of which are hereby incorporated by reference in their entirety]. Further amino acid substitutions to the IgG-Bm are also envisioned, which parallel those which can be made in IgG-B and may include amino acid substitutions to favor heterodimer formation in bispecific antibodies.

As used herein, a "substitution of an amino acid residue" with another amino acid residue in an amino acid sequence of an antibody for example, is equivalent to "replacing an amino acid residue" with another amino acid residue and denotes that a particular amino acid residue at a specific position in the amino acid sequence has been replaced by (or substituted for) by a different amino acid residue. Such substitutions can be particularly designed i.e., purposefully replacing an alanine with a serine at a specific position in the amino acid sequence by e.g., recombinant DNA technology. Alternatively, a particular amino acid residue or string of amino acid residues of an antibody can be replaced by one or more amino acid residues through more natural selection processes e.g., based on the ability of the antibody produced by a cell to bind to a given region on that antigen, e.g., one containing an epitope or a portion thereof, and/or for the antibody to comprise a particular CDR that retains the same canonical structure as the CDR it is replacing. Such substitutions/replacements can lead to "variant" CDRs and/or variant antibodies. As used herein, the term "antibody" refers to any form of antibody that exhibits the desired biological activity. An antibody can be a monomer, dimer, or larger multimer. Thus, it is used in the broadest sense and specifically covers, but is not limited to, monoclonal antibodies (including full length monoclonal antibodies), polyclonal antibodies, multispecific antibodies (e.g., bispecific antibodies), caninized antibodies, fully canine antibodies, chimeric antibodies and camelized single domain antibodies. "Parental antibodies" are antibodies obtained by exposure of an immune system to an antigen prior to modification of the antibodies for an intended use, such as caninization of an antibody for use as a canine therapeutic antibody.

As used herein, antibodies and/or the bispecific antibodies of the present invention that "block" or is "blocking" or is "blocking the binding" of e.g., a canine receptor to its binding partner (ligand), is an antibody and/or the bispecific antibody that blocks (partially or fully) the binding of the canine receptor to its canine ligand and vice versa, as determined in standard binding assays (e.g., BIACore®, ELISA, or flow cytometry).

A "bivalent antibody" comprises two antigen binding sites. In some instances, the two binding sites have the same antigen specificities.

As used herein, a "bispecific antibody" is an artificial protein that can target two different antigens at the same time. One preferred type of bispecific antibody is an IgG-like antibody that consists of four different polypeptide chains. Accordingly, a bispecific antibody can be a heterodimer comprising two monomers that each comprise a heavy and light chain. The first monomer can be from an antibody to one particular antigen, while the second monomer can be from an antibody to a different antigen. For example, certain bispecific antibodies of the present invention can target IL-31 and IL-22 at the same time. Such antibodies are formed by association of one heavy chain and one light chain with specificity for the IL-31 with a heavy chain and light chain with specificity for the IL-22. Furthermore, each of the heavy and light chains can be modified with specific mutations of their amino acid sequence so as to favor the association of the heavy chain and the light chain of the IL-22 antibody with each other and the heavy chain and the light chain of IL-31 antibody with each other, but simultaneously favor the association of the heavy chain from IL-22 antibody with the heavy chain of the IL-31 antibody over the association of a IL-22 heavy chain with another IL-22 heavy chain or a IL-31 heavy chain with another IL-31 heavy chain.

Within the context of a bispecific antibody, a "monomer" of an antibody consists of one heavy chain and one light chain of that antibody.

As used herein, an "artificial protein" and an "artificial protein molecule" are used interchangeably and denote a protein (or multimer of proteins, such as dimers, heterodimers, tetramers, and heterotetramers, etc.) that does not naturally exist in nature, such as a man-made fusion protein or a heterodimer of monomers from two different antibodies.

Typically, an antibody or antigen binding fragment of the invention retains at least 10% of its canine antigen binding activity (when compared to the parental antibody) when that activity is expressed on a molar basis. Preferably, an antibody or antigen binding fragment of the invention retains at least 20%, 50%, 70%, 80%, 90%, 95% or 100% or more of the canine antigen binding affinity as the parental antibody. It is also intended that an antibody or antigen binding fragment of the invention can include conservative or non-conservative amino acid substitutions (referred to as "conservative variants" or "function conserved variants" of the antibody) that do not substantially alter its biologic activity.

"Isolated antibody" refers to the purification status and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

As used herein, a "chimeric antibody" is an antibody having the variable domain from a first antibody and the constant domain from a second antibody, where the first and second antibodies are from different species. [U.S. Pat. No. 4,816,567; and Morrison et al., Proc. Natl. Acad. Sci. USA 81:6851-6855 (1984)]. Typically the variable domains are obtained from an antibody from an experimental animal (the "parental antibody"), such as a rodent, and the constant domain sequences are obtained from the animal subject antibodies, e.g., human or canine so that the resulting chimeric antibody will be less likely to elicit an adverse immune response in a human or canine subject respectively, than the parental (e.g., rodent) antibody.

As used herein, the term "caninized antibody" refers to forms of antibodies that contain sequences from both canine and non-canine (e.g., murine or rat) antibodies. In general, the caninized antibody will comprise substantially all of at least one or more typically, two variable domains in which all or substantially all of the hypervariable loops correspond to those of a non-canine immunoglobulin (e.g., comprising 6 CDRs as exemplified below), and all or substantially all of the framework (FR) regions (and typically all or substantially all of the remaining frame) are those of a canine immunoglobulin sequence. As exemplified herein, a caninized antibody comprises both the three heavy chain CDRs and the three light chain CDRS from a murine or rat anti-canine antigen antibody together with a canine frame or a modified canine frame. A modified canine frame comprises one or more amino acids changes as exemplified herein that further optimize the effectiveness of the caninized antibody, e.g., to increase its binding to its canine antigen and/or its ability to block the binding of that canine antigen to the canine antigen's natural binding partner.

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; $5^{th}$ ed.; NIH Publ. No. 91-3242 (1991); *Kabat, Adv. Prot. Chem.* 32:1-75 (1978); Kabat, et al., *J. Biol. Chem.* 252:6609-6616 (1977); Chothia, et al., *J. Mol. Biol.* 196:901-917 (1987) or Chothia, et al., *Nature* 342:878-883 (1989)].

As used herein, the term "hypervariable region" refers to the amino acid residues of an antibody that are responsible for antigen-binding. The hypervariable region comprises amino acid residues from a "complementarity determining region" or "CDR" [i.e. CDRL1 (or LCDR1), CDRL2 (or LCDR2), and CDRL3 (or LCDR3) in the light chain variable domain and CDRH1 (or HCDR1), CDRH2 (or HCDR2), and CDRH3 (or HCDR3) in the heavy chain variable domain]. [See Kabat et al. *Sequences of Proteins of Immunological Interest,* 5th Ed. Public Health Service, National Institutes of Health, Bethesda, Md. (1991), defining the CDR regions of an antibody by sequence; see also Chothia and Lesk, *J. Mol. Biol.* 196:901-917 (1987) defining the CDR regions of an antibody by structure]. As used herein, the term "framework" or "FR" residues refers to those variable domain residues other than the hypervariable region residues defined herein as CDR residues.

There are four known IgG heavy chain subtypes of dog IgG and they are referred to as IgG-A, IgG-B, IgG-C, and IgG-D. The two known light chain subtypes are referred to as lambda and kappa. In specific embodiments of the invention, besides binding and activating of canine immune cells, a canine or caninized antibody against its antigen of the present invention optimally has two attributes:

1. Lack of effector functions such as antibody-dependent cytotoxicity (ADCC) and complement-dependent cytotoxicity (CDC), and
2. be readily purified on a large scale using industry standard technologies such as that based on protein A chromatography.

None of the naturally occurring canine IgG isotypes satisfy both criteria. For example, IgG-B can be purified using protein A, but has high level of ADCC activity. On the other hand, IgG-A binds weakly to protein A, but also displays ADCC activity. Moreover, neither IgG-C nor IgG-D can be purified on protein A columns, although IgG-D displays no ADCC activity. (IgG-C has considerable ADCC activity). One way the present invention addresses these issues is by providing modified canine IgG-B antibodies and/or bispecific antibodies of the present invention specific to an antigen of the present invention that lack the effector functions such as ADCC and can be easily purified using industry standard protein A chromatography.

In alternative embodiments of the present invention, the canine IgG-B or IgG-C antibodies and/or bispecific antibodies of the present invention specific to an antigen of the present invention are purposely not modified to remove/substantially diminish the effector functions such as ADCC, and therefore retain the effector functions such as ADCC.

As used herein an "anti-pruritic agent" or "antipruritic agent" is a compound, macromolecule, and/or formulation that tends to inhibit, relieve, and/or prevent itching. Anti-pruritic agents are colloquially referred to as anti-itch drugs.

As used herein an "anti-pruritic antibody" or "antipruritic antibody" is an antibody that can act as an anti-pruritic agent in an animal, including a mammal such as a human, a canine, and/or a feline, particularly with respect to atopic dermatitis. In particular embodiments, the anti-pruritic antibody binds to specific proteins in the IL-31 signaling pathway, such as IL-31 or its receptor IL-31RA. The binding of the anti-pruritic antibody to its corresponding antigen (e.g., IL-31 or IL-31RA) inhibits the binding of e.g., IL-31 with IL-31RA, and interferes with and/or prevents the successful signaling of this pathway, and thereby inhibits, relieves, and/or prevents the itching that is otherwise caused by the IL-31 signaling pathway.

As used herein an "anti-inflammatory agent" is a compound, macromolecule, and/or formulation that that reduces inflammation by blocking the interaction of certain substances in the body that cause inflammation.

As used herein an "anti-inflammatory antibody" is an antibody that can act as an anti-inflammatory agent in an animal, including a mammal such as a human, a canine, and/or a feline, particularly with respect to atopic dermatitis. In particular embodiments, the anti-inflammatory antibody binds to specific proteins in the IL-4/IL-13 signaling pathway, such as IL-4 or the receptor IL-$4R_{\alpha}$. The binding of the anti-inflammatory antibody to its corresponding antigen (e.g., IL-4 or IL-$4R_{\alpha}$) inhibits the binding of e.g., IL-4 with IL-$4R_{\alpha}$, and interferes with and/or prevents the signaling of this pathway, thereby interfering with or preventing the chronic inflammation associated with atopic dermatitis.

As used herein an "anti-proliferative agent" is a compound, macromolecule, and/or formulation that that counteracts the induction of epithelial cell proliferation, and in particular the induction of keratinocyte cell proliferation, particularly with respect to atopic dermatitis. The interleukin-22 binding protein (IL-22BP) is one example of a naturally occurring anti-proliferative agent.

As used herein an "anti-proliferative antibody" is an antibody that can act as an anti-proliferative agent in an animal, including a mammal such as a human, a canine, and/or a feline, particularly with respect to atopic dermatitis. In particular embodiments, the anti-proliferative antibody binds to specific proteins in the IL-22 signaling pathway, such as IL-22 or the receptor IL-22 receptor (IL-22R). The binding of the anti-proliferative antibody to its corresponding antigen (e.g., IL-22 or IL-22R) inhibits the binding of e.g., IL-22 with IL-22R, and interferes with and/or prevents the signaling of this pathway, thereby interfering with or preventing the keratinocyte cell proliferation associated with atopic dermatitis.

"Homology" refers to sequence similarity between two polynucleotide sequences or between two polypeptide sequences when they are optimally aligned. When a position in both of the two compared sequences is occupied by the same base or amino acid monomer subunit, e.g., if a position in each of two DNA molecules is occupied by adenine, then the molecules are homologous at that position. The percent of homology is the number of homologous positions shared by the two sequences divided by the total number of positions compared ×100. For example, if 6 of 10 of the positions in two sequences are matched or homologous when the sequences are optimally aligned then the two sequences are 60% homologous. Generally, the comparison is made when two sequences are aligned to give maximum percent homology.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

The present invention provides isolated caninized antibodies and/or bispecific antibodies of the present invention, methods of use of the antibodies and/or bispecific antibodies in the treatment of a condition e.g., the treatment of atopic dermatitis in canines. In canine, there are four IgG heavy chains referred to as A, B, C, and D. These heavy chains represent four different subclasses of dog IgG, which are referred to as IgG-A (or IgGA), IgG-B (or IgGB), IgG-C (or IgGC) and IgG-D (or IgGD). Each of the two heavy chains consists of one variable domain (VH) and three constant domains referred to as CH-1, CH-2, and CH-3. The CH-1 domain is connected to the CH-2 domain via an amino acid sequence referred to as the "hinge" or alternatively as the "hinge region".

The DNA and amino acid sequences of these four heavy chains were first identified by Tang et al. [*Vet. Immunol. Immunopathol.* 80:259-270 (2001)]. The amino acid and DNA sequences for these heavy chains are also available from the GenBank data bases. For example, the amino acid sequence of IgGA heavy chain has accession number AAL35301.1, IgGB has accession number AAL35302.1, IgGC has accession number AAL35303.1, and IgGD has accession number (AAL35304.1). Canine antibodies also contain two types of light chains, kappa and lambda. The DNA and amino acid sequence of these light chains can be obtained from GenBank Databases. For example the kappa light chain amino acid sequence has accession number ABY 57289.1 and the lambda light chain has accession number ABY 55569.1.

Caninized murine or rat anti-canine antibodies that bind canine IL-31, IL-31RA, IL-22, or IL-4$R_\alpha$ include, but are not limited to: antibodies and/or bispecific antibodies of the present invention that comprise canine IgG-A, IgG-B, IgG-C, and IgG-D heavy chains and/or canine kappa or lambda light chains together with murine or rat anti-canine antigen CDRs. Accordingly, the present invention provides isolated caninized murine or rat anti-canine antibodies and/or bispecific antibodies of the present invention that bind to their corresponding canine antigens and block the binding of that canine antigen to their natural binding partner.

Accordingly, the present invention further provides caninized murine or rat antibodies and methods of use of the antibodies and/or bispecific antibodies of the present invention in the treatment of a condition e.g., the treatment of atopic dermatitis in canines.

The present invention further provides full length canine heavy chains that can be matched with corresponding light chains to make a caninized antibody. Accordingly, the present invention further provides caninized murine or rat anti-canine antigen antibodies (including isolated caninized murine or rat anti-canine antibodies) and/or bispecific antibodies comprising the caninized antibodies of the present invention and methods of use of the antibodies and/or bispecific antibodies of the present invention in the treatment of a condition e.g., the treatment of atopic dermatitis in canines.

The present invention also provides antibodies and/or bispecific antibodies of the present invention that comprise a canine fragment crystallizable region (cFc region) in which the cFc has been genetically modified to augment, decrease, or eliminate one or more effector functions. In one aspect of the present invention, the genetically modified cFc decreases or eliminates one or more effector functions. In another aspect of the invention the genetically modified cFc augments one or more effector function. In certain embodiments, the genetically modified cFc region is a genetically modified canine IgGB Fc region. In another such embodiment, the genetically modified cFc region is a genetically modified canine IgGC Fc region. In a particular embodiment the effector function is antibody-dependent cytotoxicity (ADCC) that is augmented, decreased, or eliminated. In another embodiment the effector function is complement-dependent cytotoxicity (CDC) that is augmented, decreased, or eliminated. In yet another embodiment, the cFc region has been genetically modified to augment, decrease, or eliminate both the ADCC and the CDC.

In order to generate variants of canine IgG that lack effector functions, a number of mutant canine IgGB heavy chains were generated. These variants may include one or more of the following single or combined substitutions in the Fc portion of the heavy chain amino acid sequence: P4A, D31A, N63A, G64P, T65A, A93G, and P95A. Variant heavy chains (i.e., containing such amino acid substitutions) were cloned into expression plasmids and transfected into HEK 293 cells along with a plasmid containing the gene encoding a light chain. Intact antibodies expressed and purified from HEK 293 cells were evaluated for binding to $Fc_\gamma R1$ and C1q to assess their potential for mediation of immune effector functions. [See, U.S. Pat. No. 10,106,607 B2, the contents of which are hereby incorporated by reference in its entirety.]

The present invention also provides modified canine IgGDs which in place of its natural IgGD hinge region they comprise a hinge region from:

IgG-A: SEQ ID NO: 26
FNECRCTDTPPCPVPEP

IgG-B: SEQ ID NO: 27
PKRENGRVPRPPDCPKCPAPEM; or

IgG-C: SEQ ID NO: 28
AKECECKCNCNNCPCPGCGL.

Alternatively, the IgG-D hinge region can be genetically modified by replacing a serine residue with a proline residue, i.e., PKESTCKCIPPCPVPES, SEQ ID NO: 29 (with the proline residue (P) underlined and in bold substituting for the naturally occurring serine residue). Such modifications can lead to a canine IgGD lacking fab arm exchange. The modified canine IgGDs can be constructed using standard methods of recombinant DNA technology [e.g., Maniatis et al., *Molecular Cloning, A Laboratory Manual* (1982)]. In order to construct these variants, the nucleic acids encoding the amino acid sequence of canine IgGD can be modified so that it encodes the modified IgGDs. The modified nucleic acid sequences are then cloned into expression plasmids for protein expression.

Sequence identity refers to the degree to which the amino acids of two polypeptides are the same at equivalent positions when the two sequences are optimally aligned. As used herein one amino acid sequence is 100% "identical" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In particular embodiments, selected deletions or insertions that could otherwise alter the correspondence between the two amino acid sequences are taken into account.

Sequence similarity includes identical residues and non-identical, biochemically related amino acids. Biochemically related amino acids that share similar properties and may be interchangeable are discussed "Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity [see, e.g., Watson et al., Molecular Biology of the Gene, *The Benjamin/Cummings Pub. Co*., p. 224 (4th Ed.; 1987)]. In addition, substitutions of structurally or functionally similar amino acids are less likely to disrupt biological activity. Exemplary conservative substitutions are set forth in Table A directly below.

TABLE A

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala; Gly |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the antibodies of the invention are also contemplated by the present invention. "Function-conservative variants," as used herein, refers to antibodies or fragments in which one or more amino acid residues have been changed without altering a desired property, such an antigen affinity and/or specificity. Such variants include, but are not limited to, replacement of an amino acid with one having similar properties, such as the conservative amino acid substitutions of Table A above.

Nucleic Acids

The present invention further comprises the nucleic acids encoding the antibodies and/or the bispecific antibodies of the present invention (see e.g., Examples below).

Also included in the present invention are nucleic acids that encode immunoglobulin polypeptides comprising amino acid sequences that are at least about 70% identical, preferably at least about 80% identical, more preferably at least about 90% identical and most preferably at least about 95% identical (e.g., 95%, 96%, 97%, 98%, 99%, 100%) to the amino acid sequences of the caninized antibodies provided herein when the comparison is performed by a BLAST algorithm wherein the parameters of the algorithm are selected to give the largest match between the respective sequences over the entire length of the respective reference sequences. The present invention further provides nucleic acids that encode immunoglobulin polypeptides comprising amino acid sequences that are at least about 70% similar, preferably at least about 80% similar, more preferably at least about 90% similar and most preferably at least about 95% similar (e.g., 95%, 96%, 97%, 98%, 99%, 100%) to any of the reference amino acid sequences when the comparison is performed with a BLAST algorithm, wherein the parameters of the algorithm are selected to give the largest match between the respective sequences over the entire length of the respective reference sequences, are also included in the present invention.

As used herein, nucleotide and amino acid sequence percent identity can be determined using C, Mac Vector (MacVector, Inc. Cary, NC 27519), Vector NTI (Informax, Inc. MD), Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wisconsin) pileup program using the default parameters.

The following references relate to BLAST algorithms often used for sequence analysis: BLAST ALGORITHMS: Altschul, S. F., et al., *J. Mol. Biol.* 215:403-410 (1990); Gish, W., et al., *Nature Genet.* 3:266-272 (1993); Madden, T. L., et al., *Meth. Enzymol.* 266:131-141 (1996); Altschul, S. F., et al., *Nucleic Acids Res.* 25:3389-3402 (1997); Zhang, J., et al., *Genome Res.* 7:649-656 (1997); Wootton, J. C., et al., *Comput. Chem.* 17:149-163 (1993); Hancock, J. M. et al., *Comput. Appl. Biosci.* 10:67-70 (1994); ALIGNMENT SCORING SYSTEMS: Dayhoff, M. O., et al., "A model of evolutionary change in proteins." in *Atlas of Protein Sequence and Structure*, vol. 5, suppl. 3. M. O. Dayhoff (ed.), pp. 345-352, (1978); Natl. *Biomed. Res.* Found., Washington, DC; Schwartz, R. M., et al., "Matrices for detecting distant relationships." in *Atlas of Protein Sequence and Structure*, vol. 5, suppl. 3." (1978), M. O. Dayhoff (ed.), pp. 353-358 (1978), Natl. *Biomed. Res.* Found., Washington, *DC; Altschul, S. F., J. Mol. Biol.* 219:555-565 (1991); States, D. J., et al., *Methods* 3:66-70 (1991); Henikoff, S., et al., *Proc. Natl. Acad. Sci. USA* 89:10915-10919 (1992); Altschul, S. F., et al., *J. Mol. Evol.* 36:290-300 (1993); ALIGNMENT STATISTICS: Karlin, S., et al., *Proc. Natl. Acad. Sci. USA* 87:2264-2268 (1990); Karlin, S., et al., *Proc. Natl. Acad. Sci. USA* 90:5873-5877 (1993); Dembo, A., et al., *Ann. Prob.* 22:2022-2039 (1994); and Altschul, S. F. "Evaluating the statistical significance of multiple distinct local alignments." in *Theoretical and Computational Methods in Genome Research* (S. Suhai, ed.), pp. 1-14, Plenum, New York (1997).

Antibodies and/or the bispecific antibodies of the present invention can be produced recombinantly by methods that are known in the field. Mammalian cell lines available as hosts for expression of the antibodies or fragments disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells.

When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application Ser. No. 89/303,964.4.

In general, glycoproteins produced in a particular cell line or transgenic animal will have a glycosylation pattern that is characteristic for glycoproteins produced in the cell line or transgenic animal. Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, comprise the instant invention, independent of the glycosylation pattern that the antibodies may have. Similarly, in particular embodiments, antibodies with a glycosylation pattern comprising only non-fucosylated N-glycans may be advantageous, because these antibodies have been shown to typically exhibit more potent efficacy than their fucosylated counterparts both in vitro and in vivo [See for example, Shinkawa et al., *J. Biol. Chem.* 278:3466-3473 (2003); U.S. Pat. Nos. 6,946,292 and 7,214,775].

Antibody Engineering

Antibodies can also comprise a light chain constant region, e.g., a canine light chain constant region, such as a lambda or kappa canine light chain constant region or variant thereof. By way of example, and not limitation, the canine heavy chain constant region can be from IgG-B or a modified cFc, such as the IgG-Bm used herein [see, U.S. Pat. No. 10,106,607 B2, hereby incorporated by reference in its entirety] and the canine light chain constant region can be from a kappa light chain.

The antibodies and/or the bispecific antibodies of the present invention can be engineered to include modifications to the canine framework and/or the canine frame residues within the variable domains of a parental (i.e., mouse or rat) monoclonal antibody, e.g. to improve the properties of the antibody.

Pharmaceutical Compositions and Administration

To prepare pharmaceutical or sterile compositions comprising the antibodies and/or the bispecific antibodies of the present invention, these antibodies and/or the bispecific antibodies can be admixed with a pharmaceutically acceptable carrier or excipient. [See, e.g., *Remington's Pharmaceutical Sciences and U.S. Pharmacopeia: National Formulary*, Mack Publishing Company, Easton, PA (1984)].

Formulations of therapeutic and diagnostic agents may be prepared by mixing with acceptable carriers, excipients, or stabilizers in the form of, e.g., lyophilized powders, slurries, aqueous solutions or suspensions [see, e.g., Hardman, et al. (2001) *Goodman and Gilman's The Pharmacological Basis of Therapeutics*, McGraw-Hill, New York, NY; Gennaro (2000) *Remington: The Science and Practice of Pharmacy*, Lippincott, Williams, and Wilkins, New York, NY; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, NY]. In one embodiment, the antibodies and/or the bispecific antibodies of the present invention are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antibody compositions, administered alone or in combination with another agent, can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index (LD50/ED50). In particular aspects, antibodies exhibiting high therapeutic indices are desirable. The data obtained from these cell culture assays and animal studies can be used in formulating a range of dosage for use in canines. The dosage of such compounds lies preferably within a range of circulating concentrations that include the ED50 with little or no toxicity. The dosage may vary within this range depending upon the dosage form employed and the route of administration.

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial. In particular embodiments, the antibodies and/or the bispecific antibodies of the present invention can be administered by an invasive route such as by injection. In further embodiments of the invention, the antibodies and/or the bispecific antibodies of the present invention, or pharmaceutical composition thereof, is administered intravenously, subcutaneously, intramuscularly, intraarterially, or by inhalation, aerosol delivery. Administration by non-invasive routes (e.g., orally; for example, in a pill, capsule or tablet) is also within the scope of the present invention.

Compositions can be administered with medical devices known in the art. For example, a pharmaceutical composition of the invention can be administered by injection with a hypodermic needle, including, e.g., a prefilled syringe or autoinjector. The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

The pharmaceutical compositions disclosed herein may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternatively, one may administer the antibodies and/or the bispecific antibodies of the present invention in a local rather than systemic manner, often in a depot or sustained release formulation.

The administration regimen depends on several factors, including the serum or tissue turnover rate of the therapeutic the antibodies and/or the bispecific antibodies, the level of symptoms, the immunogenicity of the therapeutic antibodies and/or the bispecific antibodies and the accessibility of the target cells in the biological matrix. Preferably, the administration regimen delivers sufficient therapeutic antibodies and/or the bispecific antibodies to effect improvement in the target disease/condition state, while simultaneously minimizing undesired side effects. Accordingly, the amount of biologic delivered depends in part on the particular therapeutic antibodies and/or the bispecific antibodies and the severity of the condition being treated. Guidance in selecting appropriate doses of therapeutic antibodies is available [see, e.g., Wawrzynczak *Antibody Therapy*, Bios Scientific Pub. Ltd, Oxfordshire, U K (1996); Kresina (ed.) *Monoclonal Antibodies, Cytokines and Arthritis*, Marcel Dekker, New York, NY (1991); Bach (ed.) *Monoclonal Antibodies and Peptide Therapy in Autoimmune Diseases*, Marcel Dekker, New York, NY (1993); Baert, et al. *New Engl. J. Med.* 348:601-608 (2003); Milgrom et al. *New Engl. J. Med.* 341:1966-1973 (1999); Slamon et al. *New Engl. J. Med.* 344:783-792 (2001); Beniaminovitz et al. *New Engl. J. Med.* 342:613-619 (2000); Ghosh et al. *New Engl. J. Med.* 348:24-32 (2003); Lipsky et al. *New Engl. J. Med.* 343:1594-1602 (2000)].

Determination of the appropriate dose is made by the veterinarian, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of the symptoms.

Antibodies and/or the bispecific antibodies provided herein may be provided by continuous infusion, or by doses administered, e.g., daily, 1-7 times per week, weekly, biweekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 μg/kg body weight, more generally at least 0.2 μg/kg, 0.5 μg/kg, 1 μg/kg, 10 μg/kg, 100 μg/kg, 0.25 mg/kg, 1.0 mg/kg, 2.0 mg/kg, 5.0 mg/ml, 10 mg/kg, 25 mg/kg, 50 mg/kg or more [see, e.g., Yang, et al. *New Engl. J. Med.* 349:427-434 (2003); Herold, et al. *New Engl. J. Med.* 346:1692-1698 (2002); Liu, et al. *J. Neurol. Neurosurg. Psych.* 67:451-456 (1999); Portielji, et al. *Cancer Immunol. Immunother.* 52:133-144 (2003)]. Doses may also be provided to achieve a pre-determined target concentration of antibodies and/or the bispecific antibodies of the present invention in the canine's serum, such as 0.1, 0.3, 1, 3, 10, 30, 100, 300 μg/ml or more. In other embodiments, antibodies and/or the bispecific antibodies of the present invention is administered subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject (e.g., a canine) with a disorder, condition and/or symptom, or with the potential to develop such a disorder, disease or symptom.

As used herein, the terms "therapeutically effective amount", "therapeutically effective dose" and "effective amount" refer to an amount of antibodies and/or the bispecific antibodies of the present invention that, when administered alone or in combination with an additional therapeutic agent to a cell, tissue, or subject, e.g., canine, is effective to cause a measurable improvement in one or more symptoms of a disease or condition or the progression of such disease or condition. A therapeutically effective dose further refers to that amount of the antibodies and/or the bispecific antibodies sufficient to result in at least partial amelioration of symptoms, e.g., treatment, healing, prevention or amelioration of the relevant medical condition, or an increase in rate of treatment, healing, prevention or amelioration of such conditions. When applied to a combination, a therapeutically effective dose refers to combined amounts of the active ingredients that result in the therapeutic effect, whether administered in combination, serially, or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess severity of the condition.

Other Combination Therapies

The compositions comprising the antibodies and/or the bispecific antibodies of the present invention, can comprise one or more additional therapeutic components. One such family of therapeutic components are Janus kinase (JAK) inhibitors. In a particular embodiment of this type the JAK inhibitor comprises the chemical formula of:

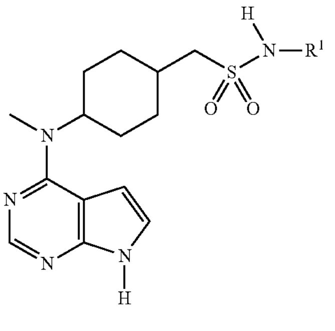

where $R^1$ is C1-4 alkyl optionally substituted with hydroxy, and pharmaceutically acceptable salts thereof [U.S. Pat. Nos. 8,133,899; 8,987,283]. More particularly the JAK inhibitor is oclacitinib and even more particularly, oclacitinib maleate. An alternative JAK inhibitor, which preferentially inhibits JAK1 relative to JAK3 is: 1-[(3R,4S)-4-cyanotetrahydropyran-3-yl]-3-[(2-fluoro-6-methoxy-4-pyridyl)amino]pyrazole-4-carboxamide, which comprises the chemical formula of:

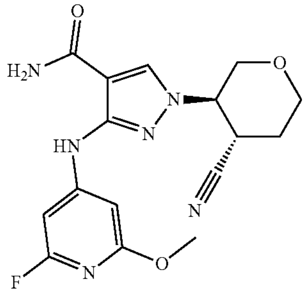 [SMILES: COc1cc(Nc2nn([C@H]3COCC[C@@H]3C#N)cc2C(N)=O)cc(F)n1]

and pharmaceutically acceptable salts thereof [see, WO 2018/108969].

Another therapeutic component that can be added to a composition of the present invention can be a spleen tyrosine kinase (SYK) inhibitor. One such SYK inhibitor is (1S,4R)-4-hydroxy-2,2-dimethyl-4-{5-[3-methyl-5-(4-methyl-pyrimidin-2-ylamino)-phenyl]-1,3-thiazol-2-yl}-cyclohexanecarboxylic acid or pharmaceutically acceptable salts thereof [see e.g., U.S. Pat. No. 8,759,366].

In addition, yet another therapeutic component that can be added to a composition of the present invention can an antagonist to a chemoattractant receptor-homologous molecule expressed on TH2 cells comprising the chemical formula of:

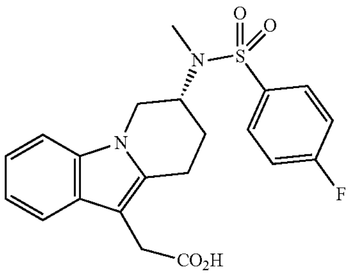 [SMILES: CN([C@@H]1CCc2c(CC(=O)O)c3ccccc3n2C1)S(=O)(=O)c1ccc(F)cc1]

and pharmaceutically acceptable salts thereof [see also, U.S. Pat. Nos. 7,696,222, 8,546,422, 8,637,541, WO 2010/099039; WO 2010/031183; and U.S. Pat. No. 8,546,422].

These additional therapeutic components can be administered to the canine subject prior to, in conjunction with, or following the administration of the composition comprising the antibodies and/or the bispecific antibodies of the present invention.

EXAMPLES

General Material and Methods: In all of the examples below, the recombinant proteins were obtained by providing the amino acid sequence for a selected protein to a commercial manufacturer (ATUM, Newark, California), who in turn chose an appropriate nucleotide sequence that encoded this amino acid sequence. The nucleotide sequences can also be obtained from publicly available DNA databases, such as GenBank®. The commercial manufacturer then chemically synthesized the nucleic acid, which next was cloned by ATUM into an expression plasmid (pD2610-v10; available from AU™) for producing the corresponding recombinant protein. The plasmid was placed into either HEK-293 cells or CHO cells to express the recombinant protein, which was then isolated by conventional methods.

Example 1

Canine IL-22 and Anti-Canine IL-22 Antibodies

A nucleic acid encoding canine IL-22 with a C-terminal HIS tag was chemically synthesized and cloned into an expression plasmid that is suitable for production of the canine IL-22-HIS protein in eukaryotic cells, either HEK-293 or CHO cells. The resulting canine protein comprises the amino acid sequence of SEQ ID NO: 1

```
cIL-22-HIS: [SEQ ID NO: 1]
LPISSHCRLDKSNFQQPYITNRTFMLAKEASLADNNTDVRLIGEKLFHGV

NMGERCYLMKEVLNFTLEEVLLPQSDRFQPYMQEVVPFLARLSNKLSQCH

IENDDQHIQRNVQKLKDTVQKLGENGEIKAIGELDLLEMALRNACVHHHH

HH
```

In addition, a nucleic acid encoding the heavy chain and the light chain of a human monoclonal antibody [Fezakinumab; disclosed in WHO Drug Information, Vol. 24, No. 1, 2010)] that binds canine IL-22 were chemically synthesized and cloned separately into an expression plasmid that is produced the anti-canine IL-22 antibody in eukaryotic cells, (in either HEK-293 or CHO cells). The heavy chain comprising the amino acid sequence of SEQ ID NO: 2 and the light chain comprising the amino acid sequence of SEQ ID NO: 3 of Fezakinumab are reproduced below:

```
Human Fezakinumab Heavy chain:
[SEQ ID NO: 2] PRIOR ART
QVQLVQSGAEVKKPGASVKVSCKASGYTFTNYYMHWVRQAPGQGLEWVG

WINPYTGSAFYAQKFRGRVTMTRDTSISTAYMELSRLRSDDTAVYYCAR

EPEKFDSDDSDVWGRGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKENWYVDGVEVHNAKTK

PREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPE

NNYKTTPPVLDSDGSFFLSKLTVDKSRWQQGNVFSCSVMHEALHNHYTQ

KSLSLSPG

Human Fezakinumab Light chain:
[SEQ ID NO: 3] PRIOR ART
QAVLTQPPSVSGAPGQRVTISCTGSSSNIGAGYGVHWYQQLPGTAPKLL

IYGDSNRPSGVPDRFSGSKSGTSASLAITGLQAEDEADYYCQSYDNSLS

GYVFGGGTQLTVLGQPKAAPSVTLFPPSSEELQANKATLVCLISDFYPG

AVTVAWKADSSPVKAGVETTTPSKQSNNKYAASSYLSLTPEQWKSHRSY

SCQVTHEGSTVEKTVAPTECS
```

Complementarity determining regions (CDRs) useful for the construction of caninized antibodies that bind to canine IL-22 are exemplified by LC CDRs and HC CDRs of the antibody Fezakinumab in Table 1A and 1B.

TABLE 1A

AMINO ACID SEQUENCES OF PRIOR ART FEZAKINUMAB CDRs

| CDRs | AMINO ACID SEQUENCE OF IL-22 ANTIBODY FEZAKINUMAB LC AND HC CDRS | SEQ ID NO: |
|---|---|---|
| HCDR-1 | AsnTyrTyrMetHis | 30 |
| HCDR-2 | TrpIleAsnProTyrThrGlySerAlaPheTyrAlaGlnLysPheArgGly | 34 |
| HCDR-3 | GluProGluLys PheAspSerAspAspSerAspVal | 38 |
| LCDR-1 | ThrGlySerSerSerAsnIleGlyAlaGlyTyrGlyValHis | 32 |
| LCDR-2 | GlyAspSerAsnArgProSer | 36 |
| LCDR-3 | GlnSerTyrAspAsnSerLeuSerGlyTyrVal | 40 |

TABLE 1B

NUCLEOTIDE SEQUENCES OF PRIOR ART FEZAKINUMAB CDRs

| CDRs | NUCLEI ACID SEQUENCE OF IL-22 ANTIBODY FEZAKINUMAB LC AND HC CDRs | SEQ ID NO: |
|---|---|---|
| HCDR-1 | aactattatatgcat | 31 |
| HCDR-2 | tggattaacccgtataccggcagcgcgttttatgcgcagaaatttcgcggc | 35 |
| HCDR-3 | gaaccggaaaaatttgatagcgatgatagcgatgtg | 39 |
| LCDR-1 | accggcagcagcagcaacattggcgcgggctatggcgtgcat | 33 |
| LCDR-2 | ggcgatagcaaccgcccgagc | 37 |
| LCDR-3 | cagagctatgataacagcctgagcggctatgtg | 41 |

Anti-canine IL-22 antibodies useful for the present inventions are also exemplified by the caninized antibodies that are produced from combination of the pairs of heavy chains and light chains listed below. The amino acid sequences of each of the paired light and heavy chain of the caninized antibodies, i.e., SEQ ID NOs: 20 with 21, 22 with 23, and 24 with 25, provided below contain the respective CDRs of the antibody Fezakinumab. The heavy chains comprise a modified Fc, IgG-Bm, which is defined above.

```
cFezaVL1-cLC:
                                          [SEQ ID NO: 20]
QAVLTQPPSVSAVLGQRVTISCTGSSSNIGAGYGVHWYQQLPGKSPKTI
IYGDSNRPSGVPDRESGSKSGSTASLTITGLQAEDEADYYCQSYDNSLS
GYVFGSGTQLTVLGQPKASPSVTLFPPSSEELGANKATLVCLISDFYPS
GVTVAWKADGSPVTQGVETTKPSKQSNNKYAASSYLSLTPDKWKSHSSF
SCLVTHEGSTVEKKVAPAECS

cFeza VH1-cIgG-Bm:
                                          [SEQ ID NO: 21]
EVQLVQSGAEVKKPGASVKVSCKTSGYTFTNYYMHWVRQAPGAGLDWMG
WINPYTGSAFYAQKERGRVTLTADTSTSTAYMELSSLRAGDIAVYYCAR
EPEKFDSDDSDVWGQGTLVTVSSASTTAPSVFPLAPSCGSTSGSTVALA
CLVSGYFPEPVTVSWNSGSLTSGVHTFPSVLQSSGLYSLSSMVTVPSSR
WPSETFTCNVAHPASKTKVDKPVPKRENGRVPRPPDCPKCPAPEMLGGP
SVFIFPPKPKDTLLIARTPEVTCVVVALDPEDPEVQISWFVDGKQMQTA
KTQPREEQFAGTYRVVSVLPIGHQDWLKGKQFTCKVNNKALPSPIERTI
SKARGQAHQPSVYVLPPSREELSKNTVSLTCLIKDEFPPDIDVEWQSNG
QQEPESKYRTTPPQLDEDGSYFLYSKLSVDKSRWQRGDTFICAVMHEAL
HNHYTQESLSHSPG
```

-continued

```
cFeza VL2-cLC:
                                          [SEQ ID NO: 22]
QAVLTQPPSVSAVLGQRVTISCTGSSSNIGAGYGVHWYQQLPGKSPKLL
IYGDSNRPSGVPDRESGSKSGSTASLTITGLQAEDEADYYCQSYDNSLS
GYVFGGGTHLTVLGQPKASPSVTLFPPSSEELGANKATLVCLISDFYPS
GVTVAWKADGSPVTQGVETTKPSKQSNNKYAASSYLSLTPDKWKSHSSF
SCLVTHEGSTVEKKVAPAECS

cFeza VH2-cIgG-Bm:
                                          [SEQ ID NO: 23]
EVQLVQSGAEVKKPGASVKVSCKASGYTFTNYYMHWVRQAPGAGLDWVG
WINPYTGSAFYAQKERGRVTLTRDTSTSTAYMELSSLRAGDIAVYYCAR
EPEKFDSDDSDVWGQGTLVTVSSASTTAPSVEPLAPSCGSTSGSTVALA
CLVSGYFPEPVTVSWNSGSLTSGVHTFPSVLQSSGLYSLSSMVTVPSSR
WPSETFTCNVAHPASKTKVDKPVPKRENGRVPRPPDCPKCPAPEMLGGP
SVFIFPPKPKDTLLIARTPEVTCVVVALDPEDPEVQISWFVDGKQMQTA
KTQPREEQFAGTYRVVSVLPIGHQDWLKGKQFTCKVNNKALPSPIERTI
SKARGQAHQPSVYVLPPSREELSKNTVSLTCLIKDFFPPDIDVEWQSNG
QQEPESKYRTTPPQLDEDGSYFLYSKLSVDKSRWQRGDTFICAVMHEAL
HNHYTQESLSHSPG

cFeza VL3-cLC:
                                          [SEQ ID NO: 24]
QSVLTQPPSVSGFLGQRVTISCTGSSSNIGAGYGVHWYQQLPGTGPRLL
IYGDSNRPSGVPDRESGSRSGSTATLTISGLQAEDEADYYCQSYDNSLS
GYVFGGGTHLTVLGQPKASPSVTLFPPSSEELGANKATLVCLISDFYPS
GVTVAWKADGSPVTQGVETTKPSKQSNNKYAASSYLSLTPDKWKSHSSF
SCLVTHEGSTVEKKVAPAECS

cFeza VH3-cIgG-Bm: [SEQ ID NO: 25]
EVQLVQSGAEVKKPGASVKVSCKASGYTFTNYYMHWVRQAPGAGLDWVG
WINPYTGSAFYAQKERGRVTMTRDTSTSTAYMELSSLRAGDIAVYYCAR
EPEKFDSDDSDVWGQGTLVTVSSASTTAPSVFPLAPSCGSTSGSTVALA
CLVSGYFPEPVTVSWNSGSLTSGVHTFPSVLQSSGLYSLSSMVTVPSSR
WPSETFTCNVAHPASKTKVDKPVPKRENGRVPRPPDCPKCPAPEMLGGP
SVFIFPPKPKDTLLIARTPEVTCVVVALDPEDPEVQISWFVDGKQMQTA
KTQPREEQFAGTYRVVSVLPIGHQDWLKGKQFTCKVNNKALPSPIERTI
```

-continued

SKARGQAHQPSVYVLPPSREELSKNTVSLTCLIKDFFPPDIDVEWQSNG

QQEPESKYRTTPPQLDEDGSYFLYSKLSVDKSRWQRGDTFICAVMHEAL

HNHYTQESLSHSPG

The binding of canine IL-22 HIS to the anti-IL-22 antibody Fezakinumab was determined by ELISA as follows:

Materials:

1. Coating Antigen: cIL-22-His,
2. Fezakinumab-mAb,
3. Mouse Anti-human IgG, Fc Peroxidase Conjugate, Calbiochem 411550, Lot D00167423,
4. 1-Step™ Ultra TMB-ELISA, Thermo Scientific 34028, Lot UF2782982,
5. NVSL PBST Lot: 5011318-0206
6. 1.5M Phosphoric Acid, MAH Lot 5011318-0219, Method:

1. Dilute cIL-22-His to 1 μg/mL in PBS and add 100 μL/well to ELISA plate. Incubate at 2-7° C. overnight.
2. Wash coated plate(s) 3 times, 200 μL/well/wash with NVSL-PBST using automatic plate washer.
3. Block ELISA plate with 200 μL of 5% NFDM in NVSL-PBST, seal and incubate at 37° C. for at least 60 minutes.
4. Wash blocked ELISA plate 3 times, 200 μL/well/wash with NVSL-PBST using automatic plate washer.
5. Pre-dilute Feza-mAb to 5 μg/mL and 3-fold serially dilute across a dilution plate. Transfer 50 μL of the diluted Feza-mAb to the ELISA plate, seal and incubate at 37° C. with rotation for 30-60 minutes.
6. Wash plate 3 times, 200 μL/well/wash with NVSL-PBST using automatic plate washer.
7. Add 100 μl/well 1:2500 diluted anti-human IgG, Fc peroxidase conjugate, seal and incubate at 37° C. for 60 minutes.
8. Add 100 μl/well of 1-Step™ Ultra TMB-ELISA. Incubate at 25° C. for 10 minutes.
9. Stop with 100 μl/well 1.5M Phosphoric acid.
10. Measure A450-A540 on spectrophotometer.

The plot of the binding study is shown in FIG. 1. The results indicate that the anti-IL-22 antibody binds to canine IL-22 in a dose-dependent manner.

Example 2

Antibodies to IL-4 Receptor Alpha

Particularly preferred anti-IL-4 receptor alpha antibodies useful in compositions of the present invention are exemplified by the antibody c152H11VL3-cCLk-s/c152H11VH3-cIgG-Bm and antibody c146E2VL3-cCLk-s/c146E2VH3-clgG-Bm. The individual light chains (LC) and heavy chains (HC) sequences for these antibodies are provided below.

c152H11VL3-cCLk-s (light chain):
[SEQ ID NO: 4]

EIVMTQSPASLSLSQEEKVTITCKASQNVGTNVAWYQQKPGQAPKLLIY

SASYRYSGLPDRESGSGSGTDFSFTISSLEPEDVAEFFCQQYNSYPYTF

GQGTKLEIKRNDAQPAVYLFQPSPDQLHTGSASVVCLLNSFYPKDINVK

-continued

WKVDGVIQDTGIQESVTEQDKDSTYSLSSTLTMSSTEYLSHELYSCEIT

HKSLPSTLIKSFQRSECQRVD c152H11VH3-cIgG-Bm (heavy chain):
[SEQ ID NO: 5]

EVQLVESGGDLVKPGGSLRLSCAASGFTFSSYGMSWVRQAPDKRLQWVA

TISRGGDYTYYPDSVKGRFTISRDNAKNTLYLQMNSLRAEDTAMYYCAR

GTLNNRGFASWGQGTLVTVSSASTTAPSVEPLAPSCGSTSGSTVALACL

VSGYFPEPVTVSWNSGSLTSGVHTFPSVLQSSGLYSLSSMVTVPSSRWP

SETFTCNVAHPASKTKVDKPVPKRENGRVPRPPDCPKCPAPEMLGGPSV

FIFPPKPKDTLLIARTPEVTCVVVALDPEDPEVQISWFVDGKQMQTAKT

QPREEQFAGTYRVVSVLPIGHQDWLKGKQFTCKVNNKALPSPIERTISK

ARGQAHQPSVYVLPPSREELSKNTVSLTCLIKDFFPPDIDVEWQSNGQQ

EPESKYRTTPPQLDEDGSYFLYSKLSVDKSRWQRGDTFICAVMHEALHN

HYTQESLSHSPG c146E2VL3-cCLk-s (light chain):
[SEQ ID NO: 6]

DIVLTQTPLSLSVSPGETASIYCRASESVDSYGNSELNWYQQKPGQPPK

LLIYRASNLASEIPDRESGSGSRTEFTLKISRVEADDAGVYYCQQNYEN

PRTFGQGTKLEIKRNDAQPAVYLFQPSPDQLHTGSASVVCLLNSFYPKD

INVKWKVDGVIQDTGIQESVTEQDKDSTYSLSSTLTMSSTEYLSHELYS

CEITHKSLPSTLIKSFQRSECQRVD c146E2VH3-cIgG-Bm (heavy chain):
[SEQ ID NO: 7]

EVQLVQSGAEVKKPGASVKVSCKASGYTFARYWMHWMKQAPGAGLDWIG

MIHPDSGNINYNERFKTKATLTVDKSTSTAYMELSSLRAGDIAVYYCAR

QLRNAMDYWGQGTLVTVSSASTTAPSVEPLAPSCGSTSGSTVALACLVS

GYFPEPVTVSWNSGSLTSGVHTFPSVLQSSGLYSLSSMVTVPSSRWPSE

TFTCNVAHPASKTKVDKPVPKRENGRVPRPPDCPKCPAPEMLGGPSVFI

FPPKPKDTLLIARTPEVTCVVVALDPEDPEVQISWFVDGKQMQTAKTQP

REEQFAGTYRVVSVLPIGHQDWLKGKQFTCKVNNKALPSPIERTISKAR

GQAHQPSVYVLPPSREELSKNTVSLTCLIKDFFPPDIDVEWQSNGQQEP

ESKYRTTPPQLDEDGSYFLYSKLSVDKSRWQRGDTFICAVMHEALHNHY

TQESLSHSPG

Antibodies against canine IL-4 receptor alpha were tested for their ability to inhibit STAT-6 phosphorylation in DH82 Cell as follows:

Materials

1. Actively growing DH82 cells
2. DH82 Cell Growth Media (ATCC® 302003™, Eagle's Minimum Essential Medium supplied with heat-inactivated fetal bovine serum to a final concentration of 15% w/v)
3. AlphaLISA p-STAT6 (Tyr641) Assay Kit: Perkin Elmer Catalog: ALSU-PST6-A-HV
4. Recombinant canine IL-4: R&D Systems, Catalog: 752-CL/CF
5. Recombinant canine IL-13: R&D Systems, Catalog: 5894-CL/CF 6. Perkin Elmer Envision
   a. Caninized anti-canine IL-$4R_{\alpha}$ monoclonal antibodies
   b. c146E2-H3L3
   c. c152H11-H3L3
   d. c4H3

Methods

1. Two tissue culture plates were seeded with $8\times10^4$ DH82 cells per well (200 µL with the density of $4\times10^5$ cells/mL) and incubated at 37° C. overnight.
2. The test antibodies were pre-diluted to 500 µg/mL and then 3-fold serially diluted in DH82 Cell Growth Media. The media was removed from the cell culture plates and 50 µL/well of the serially diluted test sample were transferred to each plate.
3. Canine IL-4 was diluted to 5 ng/ml in DH82 Cell Growth Media and 50 µL was added to each well of one plate. Canine IL-13 was diluted to 10 ng/ml in DH82 Cell Growth Media and 50 µL was added to each well of the second plate. The plates were incubated for 15 min at 37° C.
4. The media was removed from the plates and 100 µL per well of freshly prepared 1× lysis buffer from the AlphaLISA p-STAT-6 Assay Kit was added to the plate. The plate was agitated on a plate shaker with 350 rpm for 10 minutes at room temperature.
5. The Acceptor Mix was prepared from the AlphaLISA p-STAT6 Assay Kit and 15 µL per well was added to 30 µL of the cell lysate in 96-well 1/2 Area Plates. The plates were sealed, agitated for 2 minutes at 350 rpm, and then incubated for 2 hours at room temperature.
6. The Donor Mix was prepared from the AlphaLISA p-STAT6 Assay kit under subdued laboratory lighting and 15 µL per well was added to each plate. The plates were sealed, covered with foil, agitated for 2 minutes at 350 rpm, and then incubated for 2 hours at room temperature.
7. The plates were read using the AlphaScreen settings on the Perkin Elmer En Vison.

Three different caninized monoclonal anti-canine IL-$4R_{\alpha}$ antibodies designated c4H3 [WO2016/156588], c146E2-H3L3, and c152H11-H3L3 were evaluated for their ability to inhibit αSTAT-6 phosphorylation by blocking the binding of either canine IL-4 or canine IL-13 to canine IL-$4R_{\alpha}$. The data shown in FIG. 2 indicate that all three antibodies result in a dose-dependent inhibition of STAT-6 phosphorylation in the presence of IL-4, with c146E2-H3L3, and c152H11-H3L both binding tighter than the prior art anti-canine IL-4 receptor alpha antibody c4H3 [WO2016/156588]. The IL-4 control in the absence of IL-4R alpha (IL-$4R_{\alpha}$) antibodies is shown in the upper left hand portion of the graph. The data shown in FIG. 3 indicate that that all three antibodies result in a dose dependent inhibition of STAT-6 phosphorylation in the presence of IL-13, with c146E2-H3L3, and c152H11-H3L both binding tighter than the prior art anti-canine IL-4 receptor alpha antibody c4H3. The IL-13 control in the absence of IL-4R alpha (IL-$4R_{\alpha}$) antibodies is shown in the upper left-hand portion of the graph.

Example 3

Canine IL-31 Receptor Alpha and Antibodies to IL-31 Receptor Alpha

Nucleotide Sequence

The nucleotide sequence of SEQ ID NO: 8 encodes the extracellular domain of the canine IL-31 receptor alpha (IL-31RA) fused to a HIS tag comprises. Canine IL-31RA ECD HIS-tagged-protein comprises the amino acid sequence of SEQ ID NO: 9. The nucleotide sequence was prepared by chemical synthesis and then cloned into expression plasmids that are suitable for production of the corresponding proteins in eukaryotic cells, either HEK-293 or CHO cells.

```
Canine IL-31RA ECD-10His:
                                           [SEQ ID NO: 8]
gtgctgcccgccaagcccgagaacatcagctgcatcttctactacgagg

agaacttcacctgcacctggagccccgagaaggaggccagctacacctg

gtacaaggtgaagagaacctacagctacggctacaagagcgacatctgc

agcaccgacaacagcaccagaggcaaccacgccagctgcagcttcctgc

cccccaccatcaccaaccccgacaactacaccatccaggtggaggccca

gaacgccgacggcatcatgaagagcgacatcacctactggaacctggac

gccatcatgaagatcgagcccccgagatcttcagcgtgaagagcgtgc

tgggcatcaagagaatgctgcagatcaagtggatcagacccgtgctggc

cccccacagcagcaccctgaagtacaccctgagattcagaaccatcaac

agcgcctactggatggaggtgaacttcaccaaggaggacatcgacagag

acgagacctacaacctgaccgagctgcaggccttcaccgagtacgtgat

gaccctgagatgcgcccccgccgagagcatgttctggagcggctggagc

caggagaaggtgggcaccaccgaggaggaggcccccctacggcctggacc

tgtggagagtgctgaagcccgccatggtggacggcagaagacccgtgca

gctgatgtggaagaaggccaccggcgcccccgtgctggagaaggccctg

ggctacaacatctggtacttccccgagaacaacaccaacctgaccgaga

ccgtgaacaccaccaaccagacccacgagctgtacctgggcggcaagac

ctactgggtgtacgtggtgagctacaacagcctgggcgagagccccgtg

gccaccctgagaatccccgccctgaacgagaagaccttccagtgcatcg

aggccatgcaggcctgcctgacccaggaccagctggtggtggagtggca

gagcagcgcccccgaggtggacacctggatggtggagtggttccccgac

gtggacagcgagcccagcagcttcagctgggagagcgtgagccaggcca

gaaactggaccatccagaaggacgagctgaagcccctgtggtgctacaa

catcagcgtgtaccccgtgctgagagacagagtgggccagccctacagc

acccaggcctacgtgcaggagggcatccccagcgccggccccgtgaccc

aggccgacagcatcggcgtgaagaccgtgaccatcacctggaaggagat

ccccaagagcaagagaaacggcttcatcaagaactacaccatcttctac

caggccgaggacggcaaggagttcagcaagaccgtgaacagcaacatcc

tgcagtacagactggagagcctgaccagaagaaccagctacagcctgca

ggtgatggccagcaccaacgccggcggcaccaacggcaccaagatcaac

ttcaagaccctgagcatcagccaccaccaccaccaccaccaccaccacc

ac
```

Expression and Purification of IL-31 Receptor Alpha ECD

Plasmids comprising the nucleotide sequence of SEQ ID NO: 8 were transfected into HEK-293 or CHO cells using electroporation via the MaxCyte instrument as per the manufacturer's recommendation. Several days following transfection, the supernatants of transfected cells and un-transfected controls were harvested and spun down to remove cellular debris. IL-31RA with the histidine tag were purified from cell culture fluids by passing the clarified harvested fluid from transfected cells over nickel columns as per the manufacturer's recommendation. Purified proteins were quantified by measuring their absorbance of ultraviolet light at 280 nm.

```
canine IL-31RA ECD-10His:
                                        [SEQ ID NO: 9]
VLPAKPENISCIFYYEENFTCTWSPEKEASYTWYKVKRTYSYGYKSDIC

STDNSTRGNHASCSELPPTITNPDNYTIQVEAQNADGIMKSDITYWNLD

AIMKIEPPEIFSVKSVLGIKRMLQIKWIRPVLAPHSSTLKYTLRFRTIN

SAYWMEVNFTKEDIDRDETYNLTELQAFTEYVMTLRCAPAESMEWSGWS

QEKVGTTEEEAPYGLDLWRVLKPAMVDGRRPVQLMWKKATGAPVLEKAL

GYNIWYFPENNTNLTETVNTTNQTHELYLGGKTYWVYVVSYNSLGESPV

ATLRIPALNEKTFQCIEAMQACLTQDQLVVEWQSSAPEVDTWMVEWFPD

VDSEPSSFSWESVSQARNWTIQKDELKPLWCYNISVYPVLRDRVGQPYS

TQAYVQEGIPSAGPVTQADSIGVKTVTITWKEIPKSKRNGFIKNYTIFY

QAEDGKEFSKTVNSNILQYRLESLTRRTSYSLQVMASTNAGGINGTKIN

FKTLSISHHHHHHHHHH
```

Binding of Canine IL-31RA to Biotinylated Canine IL-31:

1. Coat immunoplate(s) with IL-31RA proteins by diluting to 10 μg/mL in PBS. Add 100 μL/well. Incubate the plate(s) at 2-7° C. overnight.
2. Wash the plates 3 times with 275 μL/well of PBST.
3. Block the plates with 200 μL/well of blocking buffer (1% Dry Milk in PBST) for 30-45 minutes at 36±2° C. with gentle shaking (120±20 RPM).
4. Wash the plates 3 times with 275 μL/well of PBST.
5. Dilute biotinylated IL-31 to 10 μg/mL in 1% NFDM in PBST.
6. 3-fold dilute biotinylated IL-31 (at 10 μg/mL) in 1% NFDM in PBST and transfer 100 μL/well to the immunoplate(s). Incubate for 30-45 minutes at 36±2° C. with gentle shaking (120±20 RPM).
7. Wash the plates 3 times with 275 μL/well of PBST.
8. Dilute HRP-Streptavidin to a final dilution of 1:1000 in 1% NFDM in PBST.
9. Add 100 μL/well of HRP-Streptavidin to the immunoplate(s) and incubate for 30-45 minutes at 36±2° C. with gentle shaking (120±20 RPM).
10. Wash the plates 3 times with 275 μL/well of PBST.
11. Combine equal volumes of pre-warmed TMB 2-Component substrate immediately before use.
12. Add 100 μL/well of prepared TMB substrate to the immunoplate(s) and incubate in the dark for 10 to 15 minutes at 36±2° C. with gentle shaking (120±20 RPM).
13. Stop the reaction by addition of 100 μL/well of 1 M H3PO4.
14. Read the plates using a microplate reader at a wavelength of 450 nm with a reference wavelength of 540 nm.

Monoclonal Antibodies Against Canine IL-31 Receptor Alpha

Monoclonal antibodies against canine IL-31RA were produced by the immunization of 2 Lewis rats multiple times with canine IL-31RA ECD (using 10 μg or 25 μg of antigen/rat each time) over a 3 to 4 weeks period. Following immunization, sera was collected from each rat and tested against canine IL-31RA by ELISA. The lymph node cells of the rat with the highest IL-31RA ECD reactivity were fused with the myeloma SP2/0 cell line to produce hybridomas. Approximately 10 days after the fusion, supernatants from growing hybridomas were screened on IL-31RA ECD protein coated plates by ELISA using the protocol described below. There were approximately 263 clones selected that showed potential binding to IL-31RA in this ELISA, with the majority of clones having an OD>1.

The Procedure for the ELISA:

1. Coat 96-well half area plates with IL-31RA (1 μg/mL in PBS buffer), 25 μL/well. Incubate the plates at 4° C. overnight.
2. Wash the plates 3 times with PBST (PBS+0.05% Tween 20)
3. Block the plates with blocking buffer (PBS with 5% FBS), 25 ul/well for 30 minutes at room temperature.
4. Transfer 25 ul/well hybridoma supernatant to the 96-well plates, incubate 60 minutes at room temperature.
5. Wash the plates 3 times by PBST.
6. Add 25 ul/well anti-rat HRP, 1:4000 dilution in blocking buffer, to the plates and incubate 60 minutes at room temperature.
7. Wash the plates 5 times by PBST.
8. Add TMB based reagent to the plates for colorimetric reaction for 2-3 minutes.
9. Stop the reactions with 0.16M sulfuric acid.
10. Read the plates by plate reader.

Blocking Activity of Anti-IL-31 Receptor Alpha Antibodies

The ability of anti-canine IL-31RA hybridoma supernatants to block binding of IL-31 to IL-31RA were evaluated in the blocking ELISA described below. Out of 263 clones that showed binding to IL-31RA, approximately 24 clones showed potential blocking of IL-31 binding to IL-31RA.

1. Coat 96-well half area plates with IL-31RA (1 μg/mL in PBS buffer), 25 μL/well. Incubate the plates at 4° C. overnight.
2. Wash the plates 3 times by PBST (PBS+0.05% Tween 20)
3. Block the plates with blocking buffer (PBS with 5% FBS), 25 ul/well, for 30 minutes at room temperature.
4. Transfer 25 ul/well hybridoma supernatant to the 96-well plates, incubate 60 minutes at room temperature.
5. Wash the plates 3 times with PBST.
6. Transfer 25 L/well of biotinylated IL31 (0.5 μg/mL in blocking buffer,) incubate 60 minutes at room temperature.
7. Wash the plates 3 times with PBST.
8. Add 25 μl/well Streptavidin-HRP, 1:5000 dilution in blocking buffer, to the plates and incubate 60 minutes at room temperature.

Wash the plates five (5) times with PBST.

Add TMB based reagent to the plates for colorimetric reaction for 2-3 minutes.

Stop the reactions with 0.16M sulfuric acid.

Read the plates by plate reader.

Biological Activity of Anti-IL-31RA Antibodies:

The ability of the anti-IL-31RA antibodies to inhibit the activation of STAT-3 is assessed using Baf3 cell lines that are transfected with the nucleotide sequences of the full-length canine IL-31RA chain and the full-length canine oncostatin M receptor (OSMR) chain. This cell line is also transfected with a luciferase reporter gene. The nucleotide sequences of these receptors were prepared by chemical synthesis and then cloned into expression plasmids that are suitable for expression of the corresponding proteins in Baf3 cells.

The ability of the anti-IL-31 receptor alpha antibodies to inhibit the activation of STAT-3 in Baf3 cells is assessed as follows:

1. Prepare a cell suspension with a viable cell density of $5\times10^5$ cells/mL and add 200 μL to each well of a 96-well tissue culture plate ($1\times10^5$ cells/well). Incubate plates in a humidified 37° C. incubator for 22-24 hours.
2. Remove media from the plates and add 200 μL Eagle's Minimum Essential Media (EMEM) to each well of the cell plate. Return the plate to the 37° C. incubator for 2 hours.
3. Remove media from the cell plate and add 50 μL/well supernatant from an anti-IL-31RA hybridoma grown in PBS. Incubate the plates at 37° C. for 1 hour. Add 50 μL/well of 80 ng/mL cIL-31 diluted in PBS and incubate the plate for 5 min at 37° C.
4. Remove media from the plate and add 100 μL/well of freshly prepared 1× lysis buffer to all wells. Agitate plate on a plate shaker at 350 rpm for 10 min at room temperature.

At this point, the cell lysates may be stored frozen at −20° C.

5. pSTAT-3 AlphaLISA:
   Prepare reagents from AlphaLISA® SureFire® Ultra™ p-STAT3 Assay Kit as per kit instructions.
   Transfer 30 μL of the cell lysate to a 96-well half area plate and add 15 μL/well Acceptor Mix to the cell lysate. Seal plate and incubate for 1 hour at room temperature.
   Add 15 μL/well of Donor Mix to the cell plate. Seal the plate, cover with foil and incubate for one hour or overnight at room temperature. Note-donor mix is light sensitive.
   Read plate on Perkin Elmer EnVison using Alpha Screen Assay settings.

```
Caninized Antibodies to canine IL-31 Receptor
alpha (IL-31RA)
IL-31 receptor alpha C10A12VH1-CIGGBM
                                   [SEQ ID NO: 42]
EVQLVESGGDLVKPGGSLRLSCVASGFTFSNYYMAWVRQAPGKGLQWVA

SISTGGGNTYYRDSVKGRFTISRDNAKNTLYLQMNSLRAEDTAMYYCAK

HGTLYFDYWGQGTLVTVSSASTTAPSVEPLAPSCGSTSGSTVALACLVS

GYFPEPVTVSWNSGSLTSGVHTFPSVLQSSGLYSLSSMVTVPSSRWPSE

TFTCNVAHPASKTKVDKPVPKRENGRVPRPPDCPKCPAPEMLGGPSVFI

FPPKPKDTLLIARTPEVTCVVVALDPEDPEVQISWFVDGKQMQTAKTQP

REEQFAGTYRVVSVLPIGHQDWLKGKQFTCKVNNKALPSPIERTISKAR

GQAHQPSVYVLPPSREELSKNTVSLTCLIKDFFPPDIDVEWQSNGQQEP

ESKYRTTPPQLDEDGSYFLYSKLSVDKSRWQRGDTFICAVMHEALHNHY

TQESLSHSPGK

IL-31 receptor alpha C10A12VL5-CCL
                                   [SEQ ID NO: 43]
QPVLTQPPSLSASLGTTARLTCERSSGDIGDSYVSWYQQKPGSPPRDLL

YVDDQRPSGVSKSFSGSKDTSANAGLLLISGLQPEDEADYYCQSYDSNI

DGPVFGGGTHLTVLGQPKASPSVTLFPPSSEELGANKATLVCLISDFYP
```

-continued

```
SGVTVAWKADGSPVTQGVETTKPSKQSNNKYAASSYLSLTPDKWKSHSS

FSCLVTHEGSTVEKKVAPAECS
```

FIG. 4 provides a graph showing the binding of IL-31 to the extracellular domain of IL-31R (IL-31RA). The extracellular domain (ECD) of canine IL-31RA was tested for its ability to bind to canine IL-31. The results indicate that IL-31RA ECD binds in a dose-dependent manner to biotinylated canine IL-31 with an EC50 of 0.3679 μg/ml.

Example 4

Antibodies to Canine IL-31

Antibodies that may be useful in the current invention are those described in U.S. Pat. No. 9,206,253B2 and U.S. Pat. No. 10,150,810B2. Preferably these antibodies have the following Light chain and Heavy chain sequences:

```
Caninized heavy chain sequence from mouse
antibody clone M14 and canine IgG-B:
                                   [SEQ ID NO: 10]
EVQLVESGPSLVKPGGSLRLTCSVTGDSITSGYWNWIRKFPGNKLEYMG

YISYSGITDYNPSLKSRITISRDTSKNQYYLQLNSVTTEDTATYYCARY

GNYGYAMDYWGQGTLVTVSSASTTAPSVFPLAPSCGSTSGSTVALACLV

SGYFPEPVTVSWNSGSLTSGVHTFPSVLQSSGLYSLSSMVTVPSSRWPS

ETFTCNVAHPASKTKVDKPVPKRENGRVPRPPDCPKCPAPEMLGGPSVF

IFPPKPKDTLLIARTPEVTCVWDLDPEDPEVQISWFVDGKQMQTAKTQP

REEQFAGTYRWSVLPIGHQDWLKGKQFTCKVNNKALPSPIERTISKARG

QAHQPSVYVLPPSREELSKNTVSLTCLIKDFFPPDIDVEWQSNGQQEPE

SKYRTTPPQLDEDGSYFLYSKLSVDKSRWQRGDTFICAVMHEALHNHYT

QESLSHSPGK

Caninized light chain sequence from mouse
antibody clone M14 and canine light chain
constant region:
                                   [SEQ ID NO: 11]
DIVMTQSPASLSVSLGQRATISCRASESVDTYGNSFMHWYQQKPGQSPK

LLIYRASNLESGIPAREGGSGSGTDFTLTIDPVQADDVATYYCQQSYED

PWTFGGGTKLEIKRNDAQPAVYLFQPSPDQLHTGSASWCLLNSFYPKDI

NVKWKVDGVIQDTGIQESVTEQDKDSTYSLSSTLTMSSTEYLSHELYSC

EITHKSLPSTLIKSFORSECQRVD

Zoe-LC: Caninized light chain sequence:
                                   [SEQ ID NO: 12]
EIVMTQSPASLSLSQEEKVTITCKASQSVSFAGTGLMHWYQQKPGQAPK

LLIYRASNLEAGVPSRESGSGSGTDESFTISSLEPEDVAVYYCQQSREY

PWTFGQGTKLEIKRNDAQPAVYLFQPSPDQLHTGSASVVCLLNSFYPKD

INVKWKVDGVIQDTGIQESVTEQDKDSTYSLSSTLTMSSTEYLSHELYS

CEITHKSLPSTLIKSFQRSEC

Zoe-HC: Caninized heavy chain sequence:
                                   [SEQ ID NO: 13]
EVQLVESGGDLVKPGGSLRLSCVASGFTFSNYGMSWVRQAPGKGLQWVA

TISYGGSYTYYPDNIKGRFTISRDNAKNTLYLQMNSLRAEDTAMYYCVR

GYGYDTMDYWGQGTLVTVSSASTTAPSVEPLAPSCGSTSGSTVALACLV
```

-continued

```
SGYFPEPVTVSWNSGSLTSGVHTFPSVLQSSGLYSLSSMVTVPSSRWPS

ETFTCNVAHPASKTKVDKPVPKRENGRVPRPPDCPKCPAPEMLGGPSVF

IFPPKPKDTLLIARTPEVTCVVVDLDPEDPEVQISWFVDGKQMQTAKTQ

PREEQFNGTYRVVSVLPIGHQDWLKGKQFTCKVNNKALPSPIERTISKA

RGQAHQPSVYVLPPSREELSKNTVSLTCLIKDFFPPDIDVEWQSNGQQE

PESKYRTTPPQLDEDGSYFLYSKLSVDKSRWQRGDTFICAVMHEALHNH

YTQESLSHSPG
```

Example 5

Bispecific Antibodies

Bispecific antibodies are artificial molecules that can target two different antigens at the same time. One preferred type of bispecific antibody is an IgG-like antibody that consists of four different polypeptide chains. Examples of bispecific antibodies of the present invention include antibody molecules that target both IL-31RA and IL-4R at the same time. Such antibodies are formed by association of one HC and one LC chain with specificity for the IL-4R$_{\alpha}$ and one HC and one LC with specificity for the IL-31RA. Each of the heavy and light chains are modified with specific substitutions/mutations of their amino acid sequence so as to favor the association of the HC and LC of IL-4R$_{\alpha}$ antibody with each other and the HC and LC of IL-31RA antibody with each other, and simultaneously favor the association of the HC from IL-4R$_{\alpha}$ antibody with the HC of the IL-31RA antibody over the association of each HC with itself.

Canine IgG-B Fc was first defined by Tang et al. [*Vet Immunology & Immunopathology,* 80:259-270 (2001)], as comprising the amino acid sequence of SEQ ID NO: 14, provided below.

```
1                                                 50
LGGPSVFIFP PKPKDTLLIA RTPEVTCVVV DLDPEDPEVQ ISWFVDGKQM
└→ CH2

51                                               100
QTAKTQPREE QFNGTYRVVS VLPIGHQDWL KGKQFTCKVN NKALPSPIER

101                                              150
TISKARGQAH QPSVYVLPPS REELSKNTVS LTCLIKDFFP PDIDVEWQSN
└→ CH3

151                                              200
GQQEPESKYR TTPPQLDEDG SYFLYSKLSV DKSRWORGDT FICAVMHEAL

201          215
HNHYTQKSLS HSPGK
```

Canine IgG-Bm differs from the naturally occurring canine IgG-B by comprising two (2) amino acid residue substitutions, D31A and N63A in the amino acid sequence of SEQ ID NO: 14 of IgG-B, i.e., the aspartic acid residue (D) at position 31 and the asparagine residue (N) at position 63 of SEQ ID NO: 14, are substituted by an alanine residue (A). The location of these residues in the amino acid sequence are indicated in bold and are underlined. These two amino acid residue substitutions serve to significantly diminish the antibody-dependent cytotoxicity (ADCC) and complement-dependent cytotoxicity (CDC) of the naturally occurring canine IgG-B [see, U.S. Pat. No. 10,106,607 B2, the contents of which are hereby incorporated by reference in their entirety]. A list of amino acid substitutions in antibody HC for favoring HC heterodimer formation are listed in the Table 2A. These substitutions either favor a knobs-into-holes approach to heterodimerization of the heavy chains or favor an electrostatic attraction between different heavy chains also to allow for heterodimerization [for a comprehensive discussion of these amino acid substitutions see, Moore et al., *Methods,* 154:38-50 (2019) and Brinkmann & Kontermann, MABS, 9:182-212 (2017)]. Within the context of the amino acid substitutions listed in Table 2A below, in some embodiments, chain 1 refers to the anti-IL-31RA heavy chain (HC) and chain 2 refers to the anti-IL-4R. HC. In other embodiments, chain 1 refers to the anti-IL-4R$_{\alpha}$ HC and chain 2 refers to the anti-IL-31RA HC. In still other embodiments, chain 1 refers to the IL-22 HC and chain 2 refers to the anti-IL-31 HC. In yet other embodiments, chain 1 refers to the anti-IL-31 HC and chain 2 refers to the IL-22 HC.

TABLE 2A

AMINO ACID REPLACEMENTS OF CANINE IgG-B Fc (SEQ ID NO: 14)

| Number | Chain 1 | Chain 2 |
|---|---|---|
| 1 | T132W | T132S/L134A/Y175V |
| 2 | T132W/S120C | T132S/L134A/Y175V/Y115C |
| 3 | K177D/R160D | D167K/E122K |
| 4 | S130H/F173A | Y115T/T162F |
| 5 | F173L | K177R |
| 6 | T132L/R160L/T162W | L117Y/F173A/Y175V |
| 7 | K126E/K177W | S113R/D167V/F173T |
| 8 | K126E/K177W/Y115C | S113R/D167V/F173T/S120C |
| 9 | K136E/K177W | E123N/D167V/F173T |
| 10 | K126D/D167M/Y175A | Q111R/S113R/T132V/K177V |
| 11 | Y115S/K136Y/T132M/K177V | E122G/E123D/S130Q/Y175A |
| 12 | L117D/L134E | L117K/T132K |
| 13 | L134D/K136S | E122Q/S130K |

TABLE 2B

KAPPA AND LAMBDA CROSSOVER SEQUENCES DOMAIN SWAB of CL and CH1

| CHAIN | JUNCTION SEQUENCE | SEQ ID NO. |
|---|---|---|
| VL$_{kappa}$-CH1 (Modified Light Chain) | FGQGTKVEIK**SS***ASTTAPSV* | 45 |
| VH-CL (Modified Heavy Chain) | WGOGTTLTVSS**AS***DAQPAV* | 46 |
| VL$_{kappa}$-CH1 (Modified Light Chain) | FGQGTKVESK**SS***ASTTAPSV* | 47 |
| VH-CL (Modified Heavy Chain) | WGOGTTLTV**SS***RNDAQPAV* | 48 |

TABLE 2B-continued

| KAPPA AND LAMBDA CROSSOVER SEQUENCES DOMAIN SWAB of CL and CH1 | | |
|---|---|---|
| CHAIN | JUNCTION SEQUENCE | SEQ ID NO. |
| $VL_{lamda}$-CH1 (Modified Light Chain) | FGGGTHLTVL**SS***ASTTAPSV* | 49 |
| VH-CL (Modified Heavy Chain) | WGOGTTLTV**SS***GQPKASP* | 50 |

FW4 (FR4) of the variable region of VH or VL in slightly enlarged font; a piece of "elbow" sequence that may contain a couple of added amino acids (in Bold); the entire "elbow" sequence is underlined; the N-terminal of the CHI or CL region are in Italics [see, Klein et al., MABS 8:1010-1020 (2016) and Schaefer, et al., Proc.Nat'l.Acad.Sci., 108:11187-11192 (2011)].

The light chains (such as the ones listed above) which are candidates for inclusion into bispecific antibodies can be made suitable for this purpose by incorporating them for example, into antibody domain arrangement that swab the position of the CL domain with the position of the CH1 domain in one of the antibody pairs while leaving the light chain in the other antibody pair of the bispecific un-altered. Other options are also possible such as a swab of the CL-VL domains with CH1-VH domains or a swab of the VL and VH domains in one of the antibody pairs.

Thus, a Variable Light (VL) domain may be exchanged for the Variable Heavy (VH) domain in a domain swab, i.e., an exchange of one of the various domains for another within the fab fragment of the antibody. In other examples, the CH1 domain may be exchanged for the (Constant Light) CL domain, resulting in a VL-CH1 and a VH-CL1. Table 2B provides examples of: (i) amino acid sequences at the juncture of the VH-CL domains and (ii) amino acid sequences at the juncture of the VL-CH1 domains following such a domain swab. In another instance the entire fab fragment could be exchanged such that VH-CH1 domains are exchanged for VL-CL domains.

Accordingly, to optimally provide IgG-like bispecific antibodies, two types of modification can be made: a) modify the Fc of the antibodies to favor heterodimerization over homodimerization of the heavy chains, and b) modify the light chains so as to favor the association of each of the two the light chains with its cognate heavy chain. The amino acid substitutions described in Table 2A can be used in the context of chain 1 and chain 2 to modify the Fc. To make the light chains suitable for inclusion in bispecific antibodies, a method that is referred to as cross-mab can be employed [Klein et al., Methods: 154: 21-23 (2019); Klein et al., MABS, 8:1010-1020 (2016); Schaefer et al., *Proc. Nat'l Acad. Sci.* 108:11187-11192 (2011)]. Using the cross-mab technology, the light chains (such as the ones of the present invention) which are candidates for inclusion into bispecific antibodies can be made suitable for this purpose by incorporating them for example, into antibody domain arrangement that swab the position of the CL domain with the position of the CH1 domain in one of the antibody pairs while leaving the light chain in the other antibody pair of the bispecific un-altered. Other options are also possible such as a swab of the CL-VL domains with CH1-VH domains or a swab of the VL and VH domains in one of the antibody pairs.

Examples of modified HC of antibodies of the present invention are:

Modified HC amino acid of caninized M14:
[SEQ ID NO: 15]
EVQLVESGPSLVKPGGSLRLTCSVTGDSITSGYWNWIRKFPGNKLEYMG
YISYSGITDYNPSLKSRITISRDTSKNQYYLQLNSVTTEDTATYYCARY -continued GNYGYAMDYWGQGTLVTVSSASTTAPSVEPLAPSCGSTSGSTVALACLV
SGYFPEPVTVSWNSGSLTSGVHTFPSVLQSSGLYSLSSMVTVPSSRWPS
ETFTCNVAHPASKTKVDKPVPKRENGRVPRPPDCPKCPAPEMLGGPSVF
IFPPKPKDTLLIARTPEVTCVWDLDPEDPEVQISWFVDGKQMQTAKTQP
REEQFAGTYRWSVLPIGHQDWLKGKQFTCKVNNKALPSPIERTISKARG
QAHQPSVYVLPPCREELSKNTVSLWCLIKDFFPPDIDVEWQSNGQQEPE
SKYRTTPPQLDEDGSYFLYSKLSVDKSRWQRGDTFICAVMHEALHNHYT
QESLSHSPGK Modified HC of Zoe-HC caninized antibody:
[SEQ ID NO: 16]
EVQLVESGGDLVKPGGSLRLSCVASGFTFSNYGMSWVRQAPGKGLQWVA
TISYGGSYTYYPDNIKGRFTISRDNAKNTLYLQMNSLRAEDTAMYYCVR
GYGYDTMDYWGQGTLVTVSSASTTAPSVEPLAPSCGSTSGSTVALACLV
SGYFPEPVTVSWNSGSLTSGVHTFPSVLQSSGLYSLSSMVTVPSSRWPS
ETFTCNVAHPASKTKVDKPVPKRENGRVPRPPDCPKCPAPEMLGGPSVF
IFPPKPKDTLLIARTPEVTCVVVDLDPEDPEVQISWFVDGKQMQTAKTQ
PREEQFNGTYRVVSVLPIGHQDWLKGKQFTCKVNNKALPSPIERTISKA
RGQAHQPSVYVLPPCREELSKNTVSLWCLIKDFFPPDIDVEWQSNGQQE
PESKYRTTPPQLDEDGSYFLYSKLSVDKSRWQRGDTFICAVMHEALHNH
YTQESLSHSPG Modified cFeza VH3-cIgG-Bm
[SEQ ID NO: 17]
EVQLVQSGAEVKKPGASVKVSCKASGYTFTNYYMHWVRQAPGAGLDWVG
WINPYTGSAFYAQKFRGRVTMTRDTSTSTAYMELSSLRAGDIAVYYCAR
EPEKFDSDDSDVWGQGTLVTVSSASTTAPSVEPLAPSCGSTSGSTVALA
CLVSGYFPEPVTVSWNSGSLTSGVHTFPSVLQSSGLYSLSSMVTVPSSR
WPSETFTCNVAHPASKTKVDKPVPKRENGRVPRPPDCPKCPAPEMLGGP
SVFIFPPKPKDTLLIARTPEVTCVVVALDPEDPEVQISWFVDGKQMQTA
KTQPREEQFAGTYRVVSVLPIGHQDWLKGKQFTCKVNNKALPSPIERTI
SKARGQAHQPSVCVLPPSREELSKNTVSLSCAIKDEFPPDIDVEWQSNG
QQEPESKYRTTPPQLDEDGSYFLVSKLSVDKSRWQRGDTFICAVMHEAL
HNHYTQESLSHSPG Modified IL-4 receptor alpha c152H11VH3-cIgG-Bm (heavy chain):
[SEQ ID NO: 18]
EVQLVESGGDLVKPGGSLRLSCAASGFTFSSYGMSWVRQAPDKRLQWVA
TISRGGDYTYYPDSVKGRFTISRDNAKNTLYLQMNSLRAEDTAMYYCAR
GTLNNRGFASWGQGTLVTVSSASTTAPSVEPLAPSCGSTSGSTVALACL
VSGYFPEPVTVSWNSGSLTSGVHTFPSVLQSSGLYSLSSMVTVPSSRWP
SETFTCNVAHPASKTKVDKPVPKRENGRVPRPPDCPKCPAPEMLGGPSV
FIFPPKPKDTLLIARTPEVTCVVVALDPEDPEVQISWFVDGKQMQTAKT
QPREEQFAGTYRVVSVLPIGHQDWLKGKQFTCKVNNKALPSPIERTISK -continued

ARGQAHQPSVCVLPPSREELSKNTVSLSCAIKDFFPPDIDVEWQSNGQQ

EPESKYRTTPPQLDEDGSYFLVSKLSVDKSRWQRGDTFICAVMHEALHN

HYTQESLSHSPG

Modified IL-4 receptor alpha c146E2VH3-cIgG-Bm: (heavy chain):

[SEQ ID NO: 19]

EVQLVQSGAEVKKPGASVKVSCKASGYTFARYWMHWMKQAPGAGLDWIG

MIHPDSGNINYNERFKTKATLTVDKSTSTAYMELSSLRAGDIAVYYCAR

QLRNAMDYWGQGTLVTVSSASTTAPSVEPLAPSCGSTSGSTVALACLVS

GYFPEPVTVSWNSGSLTSGVHTFPSVLQSSGLYSLSSMVTVPSSRWPSE

TFTCNVAHPASKTKVDKPVPKRENGRVPRPPDCPKCPAPEMLGGPSVFI

FPPKPKDTLLIARTPEVTCVVVALDPEDPEVQISWFVDGKQMQTAKTQP

REEQFAGTYRVVSVLPIGHQDWLKGKQFTCKVNNKALPSPIERTISKAR

GQAHQPSVCVLPPSREELSKNTVSLSCAIKDFFPPDIDVEWQSNGQQEP

-continued

ESKYRTTPPQLDEDGSYFLVSKLSVDKSRWQRGDTFICAVMHEALHNHY

TQESLSHSPG

Modified IL-31 receptor alpha caninized heavy chain 10A12VH1-CIGGBM

[SEQ ID NO: 44]

EVQLVESGGDLVKPGGSLRLSCVASGFTESNYYMAWVRQAPGKGLQWVA

SISTGGGNTYYRDSVKGRFTISRDNAKNTLYLQMNSLRAEDTAMYYCAK

HGTLYFDYWGQGTLVTVSSASTTAPSVEPLAPSCGSTSGSTVALACLVS

GYFPEPVTVSWNSGSLTSGVHTFPSVLQSSGLYSLSSMVTVPSSRWPSE

TFTCNVAHPASKTKVDKPVPKRENGRVPRPPDCPKCPAPEMLGGPSVFI

FPPKPKDTLLIARTPEVTCVVVALDPEDPEVQISWFVDGKQMQTAKTQP

REEQFAGTYRVVSVLPIGHQDWLKGKQFTCKVNNKALPSPIERTISKAR

GQAHQPSVYVLPPCREELSKNTVSLWCLIKDFFPPDIDVEWQSNGQQEP

ESKYRTTPPQLDEDGSYFLYSKLSVDKSRWQRGDTFICAVMHEALHNHY

TQESLSHSPGK

TABLE 3

SEQUENCE LISTING TABLE

| SEQ ID NO | SEQUENCE | A.A. | N.A. |
|---|---|---|---|
| 1 | cIL-22: cIL-22-HIS | √ | |
| 2 | Human IL-22: Fezakinumab Heavy chain | √ | |
| 3 | Human IL-22:Fezakinumab Light chain | √ | |
| 4 | cIL-4$R_\alpha$: c152H11VL3-cCLk-s (LC) | √ | |
| 5 | cIL-4$R_\alpha$: c152H11VH3-cIgG-Bm (HC) | √ | |
| 6 | cIL-4$R_\alpha$: c146E2VL3-cCLk-s (LC) | √ | |
| 7 | cIL-4$R_\alpha$: c146E2VH3-cIgG-Bm (HC) | √ | |
| 8 | cIL-31RA: CIL-31RA ECD-10His | | √ |
| 9 | cIL-31RA: CIL-31RA ECD-10His | | |
| 10 | cIL-31: caninized HC from M14 with cIgG-B | √ | |
| 11 | cIL-31: caninized LC from M14 with cLC constant region | √ | |
| 12 | cIL-31: Zoe-LC: Caninized LC | √ | |
| 13 | cIL-31:Zoe-HC: Caninized HC | √ | |
| 14 | Canine IgG-B | √ | |
| 15 | cIL-31:caninized M14 HC +A.A. substit. to facilitate hetero | √ | |
| 16 | cIL-31:Zoe-HC: cHC + a.a. substit. to facilitate hetero | √ | |
| 17 | cIL-22: Modified cFezaVH3-cIgG-Bm | √ | |
| 18 | cIL-4$R_\alpha$: Modified c152H11VH3-cIgG-Bm (HC) | √ | |
| 19 | cIL-4$R_\alpha$: Modified c146E2VH3-cIgG-Bm | √ | |
| 20 | cIL-22: cFezaVL1--cLC | √ | |
| 21 | cIL-22: cFezaVH1-cIgG-Bm | √ | |
| 22 | cIL-22: cFezaVL2--cLC | √ | |
| 23 | cIL-22: cFezaVH2-cIgG-Bm | √ | |
| 24 | cIL-22: cFezaVL3--cLC | √ | |
| 25 | cIL-22: cFezaVH3-cIgG-Bm | √ | |
| 26 | IgG-A Hinge | √ | |
| 27 | IgG-B Hinge | √ | |
| 28 | IgG-C Hinge | √ | |
| 29 | IgG-D modified Hinge | √ | |
| 30 | IL-22 HCDR-1 | √ | |
| 31 | IL-22 HCDR-1 | | √ |
| 32 | IL-22 LCDR-1 | √ | |
| 33 | IL-22 LCDR-1 | | √ |
| 34 | IL-22 HCDR-2 | √ | |
| 35 | IL-22 HCDR-2 | | √ |
| 36 | IL-22 LCDR-2 | √ | |
| 37 | IL-22 LCDR-2 | | √ |
| 38 | IL-22 HCDR-3 | √ | |
| 39 | IL-22 HCDR-3 | | √ |
| 40 | IL-22 LCDR-3 | √ | |
| 41 | IL-22 LCDR-3 | | √ |
| 42 | cIL-31RA: caninized heavy chain 10A12VH1-CIGGBM | √ | |
| 43 | cIL-31RA: caninized light chain c10A12VL5-CCL | √ | |

TABLE 3-continued

| SEQUENCE LISTING TABLE | | | |
|---|---|---|---|
| SEQ ID NO | SEQUENCE | A.A. | N.A. |
| 44 | cIL-31RA: modified caninized heavy chain 10A12VH1-CIGGBM | √ | |
| 45-50 | Junction Sequences for light chain swabs of CH1 with CL | √ | |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

We claim:

1. A bispecific antibody comprising a monomer of a caninized anti-pruritic antibody and a monomer of a caninized anti-inflammatory antibody;

wherein the caninized anti-pruritic antibody is a caninized interleukin-31 receptor alpha (IL-31RA) antibody and the caninized anti-inflammatory antibody is a caninized interleukin-4 receptor alpha (IL-4R alpha) antibody;

wherein the caninized IL-4R alpha antibody comprises a light chain comprising the amino acid sequence of SEQ ID NO: 4 and a heavy chain comprising the amino acid sequence of SEQ ID NO: 18; and wherein the caninized IL-31RA antibody comprises a light chain comprising the amino acid sequence of SEQ ID NO: 43 and a heavy chain comprising the amino acid sequence of SEQ ID NO: 42 or SEQ ID NO: 44.

2. The bispecific antibody of claim 1, wherein the light chain of the caninized IL-4R alpha antibody comprises a heavy chain constant domain 1 (CH1) in place of a light chain constant domain (CL); and wherein the heavy chain of the caninized IL-4R alpha antibody comprises the CL in place of the CH1.

3. A composition comprising the bispecific antibody of claim 1, wherein the composition further comprises a caninized anti-proliferative antibody.

4. The composition of claim 3, wherein the caninized anti-proliferative antibody is a caninized interleukin-22 (IL-22) antibody; wherein the caninized IL-22 antibody comprises a light chain comprising the amino acid sequence of SEQ ID NO: 24 and a heavy chain comprising the amino acid sequence of SEQ ID NO: 17 or SEQ ID NO: 25.

5. The composition of claim 1, further comprising one or more additional components selected from the group consisting of a Janus kinase (JAK) inhibitor, a spleen tyrosine kinase (SYK) inhibitor, and an antagonist to a chemoattractant receptor-homologous molecule expressed on TH2 cells.

6. The composition of claim 5, wherein the JAK inhibitor is (a) a compound of the formula of:

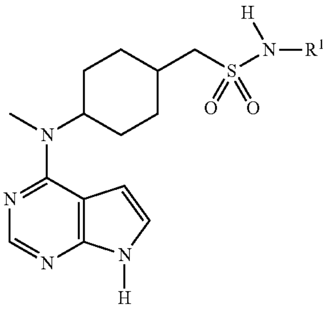

where $R^1$ is $C_{1-4}$ alkyl optionally substituted with hydroxy, or a pharmaceutically acceptable salt thereof; or (b) a compound having the structure of:

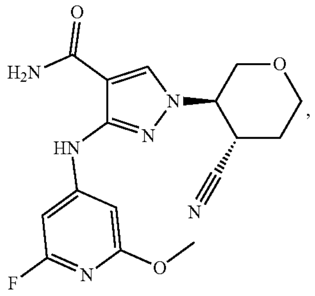 [SMILES: COc1cc(Nc2nn([C@H]3COCC[C@@H]3C#N)cc2C(N)=O)cc(F)n1]

or a pharmaceutically acceptable salt thereof.

* * * * *